(12) United States Patent
Griffin et al.

(10) Patent No.: US 12,226,084 B2
(45) Date of Patent: Feb. 18, 2025

(54) COLLECTION DEVICE AND METHOD

(71) Applicant: IDEXX Laboratories, Inc., Westbrook, ME (US)

(72) Inventors: Justin Griffin, Scarborough, ME (US); John Palme, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 904 days.

(21) Appl. No.: 17/363,279

(22) Filed: Jun. 30, 2021

(65) Prior Publication Data

US 2022/0000456 A1 Jan. 6, 2022

Related U.S. Application Data

(60) Provisional application No. 63/046,742, filed on Jul. 1, 2020.

(51) Int. Cl.
*A61B 10/00* (2006.01)
*B01L 3/00* (2006.01)
*B01L 3/02* (2006.01)

(52) U.S. Cl.
CPC ...... *A61B 10/0038* (2013.01); *A61B 10/0096* (2013.01); *B01L 3/0224* (2013.01); *B01L 3/508* (2013.01)

(58) Field of Classification Search
CPC ............ A61B 10/0038; A61B 10/0096; B01L 3/0224; B01L 3/508; B01L 3/50825;
(Continued)

(56) References Cited

U.S. PATENT DOCUMENTS 5,282,981 A * 2/1994 Adams ................ B01L 3/50215
422/918
5,785,925 A * 7/1998 U'Ren .................. B01L 3/5021
436/178
(Continued)

FOREIGN PATENT DOCUMENTS

| EP | 2435108 A2 | 4/2012 | ............. A61B 10/02 |
| JP | 2016-540494 A | 12/2016 | .............. C12M 1/26 |
| WO | WO2010138895 A2 | 12/2010 | ......... A61B 17/3207 |

OTHER PUBLICATIONS

Notification of Transmittal of the International Search Report and the Written Opinion of the International Searching Authority, or the Declaration, dated Oct. 7, 2021, which was issued by the International Searching Authority of WIPO in Applicant's corresponding international PCT application having Serial No. PCT/US2021/039791, filed on Jun. 30, 2021.
(Continued)

*Primary Examiner* — Michael L Hobbs
(74) *Attorney, Agent, or Firm* — Margot M. Ryan

(57) ABSTRACT

A collection device for examining fecal matter to determine whether a patient is afflicted with parasites includes a particle accumulating plug mounted on an end of a collection tube containing a fecal specimen. The particle accumulating plug includes an inner wall that defines an inverted funnel. A pipetting port is formed through the inner wall at the apex of the inverted funnel allowing the tip of a pipette to enter the port and aspirate the ova or eggs, or other parasite cells, that have separated from the fecal specimen. The conical shape of the inner wall of the plug directs the separated parasite ova or eggs towards the pipetting port and to accumulate within the volume of the funnel of the plug so that a desired volume of fluid containing a concentrated quantity of parasite ova or eggs may be aspirated into the pipette tip through the pipetting port.

39 Claims, 21 Drawing Sheets

(58) Field of Classification Search
CPC ......... B01L 3/50215; B01L 2200/0668; B01L 2200/026; B01L 2300/042; B01L 2300/046
See application file for complete search history.

(56) References Cited

U.S. PATENT DOCUMENTS

| | | | |
|---|---|---|---|
| 5,888,831 | A | 3/1999 | Gautsch ........................ 436/177 |
| 6,030,582 | A | 2/2000 | Levy ............................. 422/570 |
| 7,114,403 | B2 | 10/2006 | Wu et al. ................... 73/864.72 |
| 7,338,634 | B2 | 3/2008 | Chang ........................... 422/408 |
| D681,843 | S | 5/2013 | Nemeth ....................... D24/224 |
| 8,529,469 | B2 | 9/2013 | Greenwald ................... 600/573 |
| 8,540,082 | B2 | 9/2013 | Kelland et al. ............... 210/516 |
| 2010/0168613 | A1 | 7/2010 | Greenwald ................... 600/573 |
| 2017/0074759 | A1 | 3/2017 | Campton et al. | |
| 2018/0353954 | A1 | 12/2018 | Pennie | |

OTHER PUBLICATIONS

Written Opinion of the International Searching Authority, dated Oct. 7, 2021, which was issued by the International Searching Authority of WIPO in Applicant's corresponding international PCT application having Serial No. PCT/US2021/039791, filed on Jun. 30, 2021.
International Search Report, dated Oct. 7, 2021, which was issued by the International Searching Authority of WIPO in Applicant's corresponding international PCT application having Serial No. PCT/US2021/039791, filed on Jun. 30, 2021.
Communication Pursuant to Rule 62 EPC, dated Dec. 6, 2023, issued by the European Patent Office in Applicant's related European Patent Application No. EP21833836.6, filed on Dec. 23, 2022.
Supplementary European Search Report (Dec. 6, 2023—mailed with the Communication Pursuant to Rule 62 EPC), issued by the European Patent Office in Applicant's related European Patent Application No. EP21833836.6, filed on Dec. 23, 2022.
European Search Opinion (Dec. 6, 2023—mailed with the Communication Pursuant to Rule 62 EPC), issued by the European Patent Office in Applicant's related European Patent Application No. EP21833836.6, filed on Dec. 23, 2022.

\* cited by examiner

In house collection device, Pipette Cap, how it works.

Fill with slurry – doesn't need to be exact

Insert cap and push down until fill is even with pipette hole.

SECTION A-A

New collection device, workflow:

Pet owner or clinic tech scoops sample and snaps scoop into tube. Volume not critical.

"click"

Clinic opens flip cap and fills to some point (TBD until we test)

New collection device, workflow:

Vortex to mix

Top off until fill is at pipette hole

New collection device, workflow:

Centrifuge

Pipette out to Sedivue, dispose of consumable.

SECTION A-A

SECTION A-A

SECTION A-A

COLLECTION DEVICE AND METHOD

CROSS-REFERENCE TO RELATED APPLICATIONS

This application is related to U.S. Provisional Patent Application Ser. No. 63/046,742, filed on Jul. 1, 2020, and titled "Collection Device And Method", the disclosure of which is hereby incorporated by reference and on which priority is hereby claimed.

BACKGROUND OF THE INVENTION

Field of the Invention

The present invention generally relates to devices for receiving a sample in solid, semi-solid or liquid form, and separating targeted particles from the sample based on particle density or specific gravity. More specifically, the present invention relates to collection devices used in the analysis of a patient sample to determine the identification, presence or quantity of a constituent of the patient sample. Even more particularly, the present invention relates to a collection or testing device that is adapted to receive fecal matter of a patient and is used in determining whether or not the ova or eggs of parasites are present.

Description of the Related Art

It has long been recognized that analyzing fecal specimens for parasite ova is an effective method for identifying parasites afflicting a patient. This method is routinely used in clinical and veterinary laboratories around the world to identify specific parasites in fecal specimens from animals and humans so that the patient may be properly treated for the affliction. However, the method presents challenges, especially in separating a sufficient quantity of particles from the fecal matter for analysis by microscopy.

FIG. 1 illustrates, in sequence, the steps taken in carrying out a traditionally used method of separating the ova or eggs of parasites from fecal matter for analysis, the method commonly referred to as the centrifuge flotation process. Basically, the examination of fecal matter to determine whether or not the ova or eggs of parasites are present generally includes the step of collecting feces and then adding a solution of the proper specific gravity to the fecal material to provide a fecal emulsion. The ova in the emulsion can then be separated from the emulsion due to their difference in specific gravity. Centrifugation is often used to help separate the lighter ova or eggs from the fecal matter. The separated ova then can be examined to determine the necessary treatment. Examination can be made by placing the separated particles on a slide and examining the particles under a microscope.

More specifically, and with reference to the sequential steps illustrated in FIG. 1 of the drawings, an approximately one gram sample of fecal matter is obtained and added to a mixing cup. An approximately ten milliliter volume of flotation solution is mixed in the cup with the fecal sample to form an emulsion. The fecal emulsion is passed through a strainer into another cup to remove clumps and undigested vegetable matter which may be contained in the fecal specimen and which would otherwise have floated to the surface of the liquid along with the parasite ova. The strained emulsion is then poured into a centrifuge test tube, filled with flotation solution such that the tube is nearly full, and placed in a laboratory fixed angle or swinging bucket centrifuge. Centrifugation of the pre-filtered mixture accelerates the process and provides a sharper separation of ova and fecal debris.

After centrifugation, the tube containing the separated constituents is topped off with further flotation solution to form a meniscus in the tube that is accessible for contact with a coverslip. The lighter, buoyant ova will tend to float towards the meniscus.

A coverslip is placed on the open end of the centrifuge tube in contact with the meniscus of the solution therein. The clinician waits a predetermined period of time, such as about ten minutes, to allow any ova or eggs in the solution to float to the meniscus and adhere to the coverslip in contact therewith before removing the coverslip from the centrifuge tube and placing it on a microscope slide. The clinician or another technician manually inspects the slide using a microscope to determine whether or not any ova or eggs of parasites are present and to identify from the ova or eggs the type of parasite that is afflicting the patient to determine the necessary treatment.

This conventional process has been improved over the years, but still is not optimized and suffers from several limitations including the risk of exposure of laboratory personnel to potentially dangerous pathogens, complexity, unpleasant odor and also a degree of unreliability or inaccuracy. Such a conventional process is manually performed and labor intensive. Furthermore, not all of the separated parasite ova or eggs will float to the level of the meniscus of the solution, nor will all of the ova or eggs adhere to the coverslip placed on the centrifuge tube, which leads to inaccuracies in the number of each type of ova or eggs present in the sample.

Additionally, in the standard method for centrifugal flotation using a fixed angle-type centrifuge device of the kind commonly found in clinics and veterinary laboratories, the tube is restrained at an acute angle with respect to the vertical axis of flotation. Thus, the tube cannot be filled to the top to form the meniscus prior to centrifugation, and consequently a coverslip cannot be placed on the tube before the centrifugation step. The meniscus must be formed by adding fluid to the tube after centrifugation, which may disturb the ova or eggs floating on the surface. The tube must rest for about ten minutes after the fluid addition to allow the ova to ascend to the fluid surface and adhere to the coverslip.

OBJECTS AND SUMMARY OF THE INVENTION

It is an object of the present invention to provide a collection device which separates buoyant particles from a sample of matter and which concentrates the separated particles for subsequent removal from the collection device using a pipette.

It is another object of the present invention to provide a collection device for receiving fecal matter to separate parasite ova and other cells therefrom and to concentrate the separated ova and cells in the collection device for subsequent removal therefrom for automated microscopic analysis.

It is still another object of the present invention to provide a semi-automated system and method for identifying, counting or determining the presence of parasite ova or eggs in a fecal specimen using a collection device that separates and concentrates the ova or eggs in the collection device.

It is a further object of the present invention to provide a collection device for use in fecal parasite testing which minimizes the risk of exposure of laboratory personnel to potentially dangerous pathogens and unpleasant odors.

It is yet a further object of the present invention to provide a self-contained, centrifugable fecal specimen collection tube used for separating parasite ova and eggs from the specimen and which facilitates the accumulation of the separated ova and eggs in a concentrated volume of the collection device.

It is yet another object of the present invention to provide a centrifugable fecal specimen collection tube used for separating parasite ova and eggs from the specimen and which facilitates the accumulation of the separated ova and eggs in a concentrated volume, the collection device further directing solution added to the device after it is centrifuged to below the volume of the accumulated parasite ova and eggs so as not to disturb the accumulated ova and eggs in the collection device.

It is another object of the present invention to provide a collection device for receiving fecal matter and to separate parasite ova and eggs therefrom, and which avoids the need to form a meniscus of solution in the collection tube.

It is yet a further object of the present invention to provide a collection device for receiving fecal matter and to separate parasite cells therefrom, and which avoids the need to use a coverslip for the separated parasite cells to adhere thereto for later analysis.

It is still another object of the present invention to provide a fecal specimen collection device that may be used with a centrifuge to help separate parasite cells from the fecal specimen and which avoids the need for forming a meniscus of solution therein or waiting a predetermined period of time after "topping off" solution has been added to the collection device.

In accordance with a first form of the present invention, a particle accumulating plug is fitted at or near the open end of a centrifugable collection test tube containing a solid, semi-solid or liquid sample. The particles are separated from the sample by centrifugation of the collection tube, and the separated particles are accumulated by the plug for subsequent removal and analysis. In the following example, the collection test tube may receive fecal matter in a process for determining whether or not the patient is afflicted with parasites, and the particles accumulated by the plug are the ova or eggs of the parasites. Preferably, both the plug and the collection tube are formed from a transparent material, such as glass or plastic, so that the relative position of the plug with respect to the collection tube may easily be determined by the clinician or laboratory personnel viewing the plug through the transparent sidewall of the collection tube.

The tube containing the fecal specimen is at least partially filled with a flotation solution having a particular specific gravity, and the plug is added to effectively seal the open end of the collection tube. The tube is then agitated so that the specimen and solution form an emulsion or slurry. Alternatively, the fecal specimen and flotation solution may be mixed or agitated in a mixing cup to form the emulsion or slurry, a volume of which is then transferred to the centrifugable collection tube, after which the tube is sealed with the particle accumulating plug.

The plug has a particular geometry that, during or after centrifugation of the collection tube, directs buoyant particles separated from the fecal emulsion due to their lower density to concentrate in a particular area or zone of the plug. More specifically, the plug includes an inner wall having a conical shape that defines an inverted funnel to direct separated buoyant particles (e.g., the ova or eggs of parasites) towards the apex of the conically-shaped plug wall. At such an apex, where the inner wall converges, a pipetting port is formed which, as will be explained, receives the tip of a pipette for aspirating a volume of solution containing a concentrated quantity of separated particles residing within the funnel defined by the conical inner wall of the plug.

The particle accumulating plug is inserted into the open end of the collection tube to a particular depth where the surface of the slurry or emulsion is level with the pipetting port of the plug. This step may easily be determined by viewing the plug through the transparent sidewall of the collection tube. Now, the collection tube is centrifuged, which aids in the separation of the lighter, more buoyant particles (parasite ova or eggs, for example) from the heavier, denser fecal emulsion. More specifically, centrifugation of the collection tube causes the separated buoyant particles towards the plug. The conical inner wall of the plug directs the separated particles to accumulate and concentrate within this funnel, where the accumulated particles may be easily removed from the plug by the pipette.

The aspirated particles in the pipette tip may be transferred to a microscope slide for manual analysis by laboratory personnel by using a microscope, or may be transferred to an automated instrument, like the Sedivue Dx™ clinical analyzer available from IDEXX Laboratories, Inc. of Westbrook, Maine.

In a second form of the present invention, a disposable, self-contained collection device is provided. The collection device, in this second embodiment, includes a tubular body, or simply referred to herein as a tube, having a sidewall which is preferably transparent and formed of glass or plastic, and opposite first and second open axial ends. A collection scoop assembly having a scoop mounted on a cylindrical handle is used to obtain a specimen of fecal matter. The scoop assembly is inserted into the tube at the first open axial end thereof, with the scoop end carrying the fecal specimen residing within the bore of the tube. The cylindrical handle fluidtightly seals the first open axial end of the tube.

A particle accumulating plug, which is also preferably transparent and formed of glass or plastic, is mounted on the opposite second open axial end of the tube. The plug has an inner wall formed with a generally conical shape that defines an inverted funnel, similar in many respects to the design of the particle accumulating plug of the first embodiment described previously. As with the first embodiment, a pipetting port is formed in the inner conical wall of this second embodiment of the plug near where the conical wall converges to define the apex of the inverted funnel. A fill port is also formed through the particle accumulating plug to allow flotation solution to be added to the tube through the plug. A flip cap is attached to the plug by an extended living hinge to cover the plug and to insure that a fluidtight seal on the second axial end of the tube is provided.

In use, a pet owner or laboratory clinician scoops a fecal sample and snaps the scoop collection assembly into one end of the collection tube (preferably, the scoop collection assembly makes an audible noise when it is properly seated in the first axial end of the collection tube after having been removed therefrom). The technician then opens the flip cap on the other end and fills the bore of the tube with a flotation solution, such as a zinc sulfate solution having a predetermined specific gravity, and reseals the end of the tube with the cap.

The clinician then mixes the fecal specimen and solution by vigorously shaking the collection device or by using an automated agitator to form a fecal emulsion or slurry. The mixing process may also be improved by adding one or more, and potentially different sized and shaped, beads with a density sufficient to break apart the sample when agitated, such as by adding, for example, three steel beads with a diameter of about ⅛th of an inch and one steel bead with a diameter of about ¼ inches and agitated either manually or by using an automated agitator. Balls, beads or spheres may also be added to help in mixing to form the emulsion or slurry. For example, the beads used in mixing the emulsion may be about 1/16 inches to about ¼ inches in diameter, and may be made of either steel or another high density material (metal, plastic, or glass). The beads may be activated when the user vigorously shakes the tube or by an automated mixer such as a Vortexer or, if the beads are ferrous, by magnetic forces. After the contents of the collection device are thoroughly mixed, the cap is reopened and more solution is added to raise the level of the fecal emulsion in the tube such that its surface is at the level of the pipetting port. Since both the tube and the particle accumulating plug are preferably both transparent, this level can easily be determined by viewing the tube through its sidewall.

The flip cap is again placed over the plug, and the collection device is centrifuged to separate the lighter, less dense particles, such as parasite ova and eggs, or other cellular components, from the denser and heavier fecal matter in the emulsion or slurry. The conically-shaped inner wall of the plug acts as a funnel and directs the separated ova or eggs into the space within the funnel shape where the ova or eggs accumulate. The cap is removed, and the tip of a pipette is inserted into the pipetting port of the plug to aspirate into the tip a desired volume of solution with a concentrated quantity of separated particles, such as the parasite ova or eggs, or other particulate matter. The pipette is used to transfer the particle sample to a test slide for manual inspection by a clinician using a microscope, or to an automated clinical analyzer, such as the Sedivue Dx™ analyzer mentioned previously.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Reference should initially be had to FIGS. 2-7 of the drawings, which illustrate one form of a collection device 2 for separating particles from a solid, semi-solid or liquid specimen 4. Although the collection device 2 of the present invention shown in FIGS. 2-7, and the collection device 2 of the present invention shown in FIGS. 8-29, may be used to separate and accumulate various types of particles 6, such as cells or non-cellular matter, based on the density or specific gravity of the particles, from different kinds of matter, what will be described herein, and for illustrative purposes only, is the use of the collection devices 2 of the present invention to separate parasite ova, eggs, cells, oocytes and cytes from fecal matter in a method involving the examination of fecal matter to determine whether or not the ova or eggs, or other cells, of parasites are present, and to identify what kind of parasites are present, or to count the number of parasite ova or eggs to determine the extent of the parasite affliction of the patient. Additionally, the collection devices 2 of the present invention described herein are particularly adapted for use in a centrifuge flotation process, such as described previously and shown in FIG. 1 of the drawings, but may also be used in a passive flotation process (i.e., without centrifugation).

Figure 2:
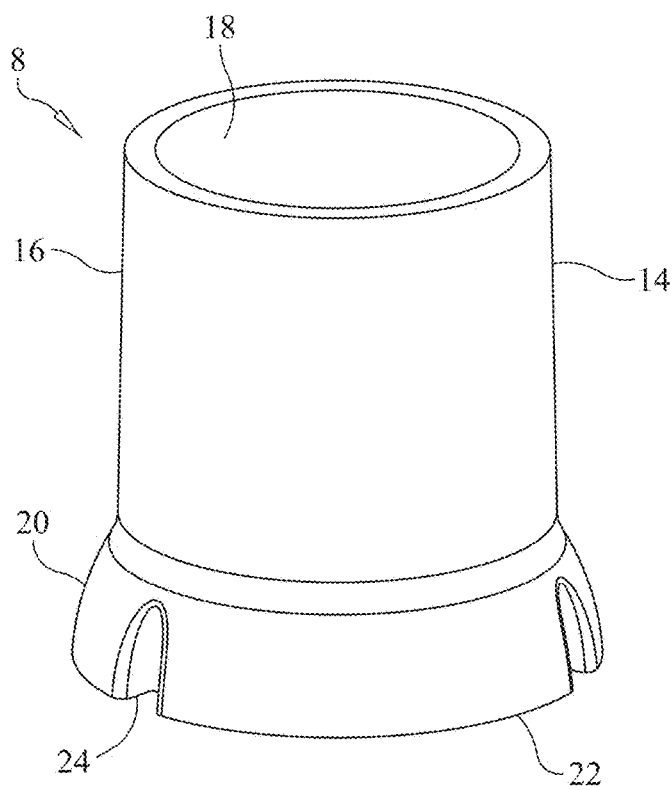
FIG. 2 is a perspective view of a first embodiment of a collection device constructed in accordance with the present invention and used in separating particles, such as parasite ova and eggs, from a specimen, such as fecal matter.
Figure 3:
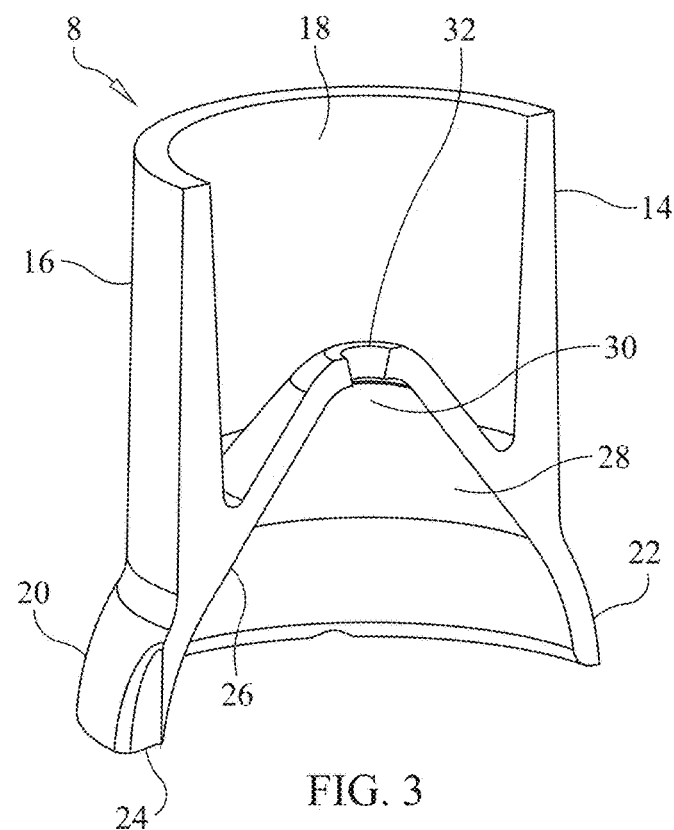
FIG. 3 is a partially cutaway, perspective view of the collection device of the present invention shown in FIG. 2.
Figure 4:
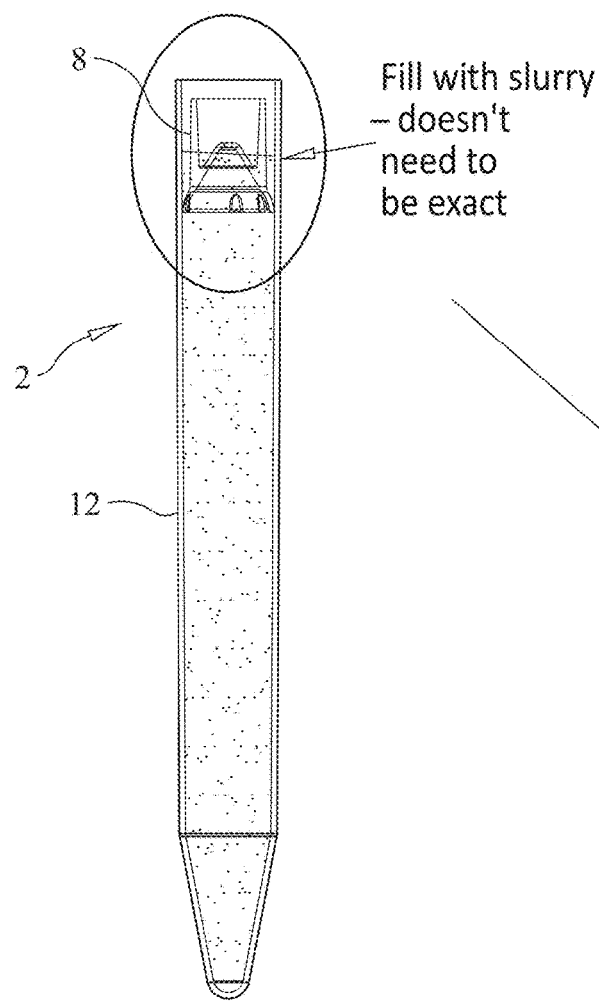
FIG. 4 is a cross-sectional view of the collection device of the present invention mounted on a centrifugable test tube and illustrating a first step in separating and accumulating particles from a specimen.

Referring now to FIGS. 2-7 of the drawings, a collection device 2 formed in accordance with the present invention includes a particle accumulating plug 8 that is insertable into the open top end 10 of a centrifuge (or non-centrifuge) test tube 12. As shown in FIGS. 2 and 3 of the drawings, the plug 8 has a generally cylindrical shape with an upper portion 14 formed with a tubular sidewall 16 defining an internal bore 18 and a lower skirt portion 20 having a resilient, outwardly flared sidewall 16 axially adjacent to the upper portion 14 and formed with a slightly larger diameter than that of the upper portion 14. The flared lower skirt portion 20 of the plug 8 includes a plurality of cutouts 24 spaced apart from each other about the circumference of the lower skirt portion 20, the number of cutouts 24 being preferably three or four, which, as will be described in greater detail, allow fluid to flow therethrough.

An inner wall 26 extends upwardly within the bore 18 of the upper portion 14 of the plug 8 from the lower skirt portion 20 thereof. The inner wall 26 is conically-shaped to define an inverted funnel 28 within the bore 18 of the plug 8. As will also be described in greater detail, this funnel shape helps to accumulate separated particles 6, such as parasite ova and eggs, within the volume or zone of the funnel 28 defined by the conical inner wall 26 during and after the test tube 12 on which the particle accumulating plug 8 is mounted is centrifuged.

The conically-shaped inner wall 26 of the plug 8 converges to an apex 30, and a pipetting port 32 is formed thereat through the thickness of the conically-shaped inner wall 26. The port 32 is dimensioned to receive the tip 34 of a pipette 36 (see, also, FIG. 30) which, as will be further described, is used to aspirate the parasite ova, eggs or cells accumulating within the volume of the funnel 28 by aspirating the separated particles 6 into the pipette tip 34 and transferring the aspirated particles 6 to a microscope slide for manual examination by a clinician using a microscope, or to transfer the separated particles 6 to an automated clinical analyzer 38, such as the Sedivue Dx™ analyzer available from IDEXX Laboratories, Inc.

FIGS. 4-7 of the drawings illustrate how the collection device 2 of the present invention is used in a method for the examination of fecal matter to determine whether a patient is afflicted with parasites. A fecal specimen taken from a patient may be placed in the centrifuge test tube 12 to which a flotation solution having a particular specific gravity is added. The flotation solution may be, but is not limited to, a zinc sulfate solution, magnesium sulfate solution, sodium chloride or another solution, the purpose of which is to raise the specific gravity to a range of about 1.18 to about 1.27 so that the ova or eggs 6 that separate from the fecal matter through centrifugation and that are lighter than the solution will rise to the top of the solution. The specific gravity or density of the flotation solution should be high enough to allow the parasite ova or eggs to float but low enough so as not to cause too much unwanted fecal matter to float. The fecal matter and solution are agitated within the test tube 12 having the plug 8 mounted thereon to form a fecal emulsion or slurry 40 within the tube 12. Alternatively, the fecal specimen and flotation solution may be mixed earlier in a separate mixing cup, and a volume of the fecal emulsion or slurry 40 which is formed is poured into the open end 10 of the test tube 12, and the particle accumulating plug 8 is then mounted thereon.

Figure 5:
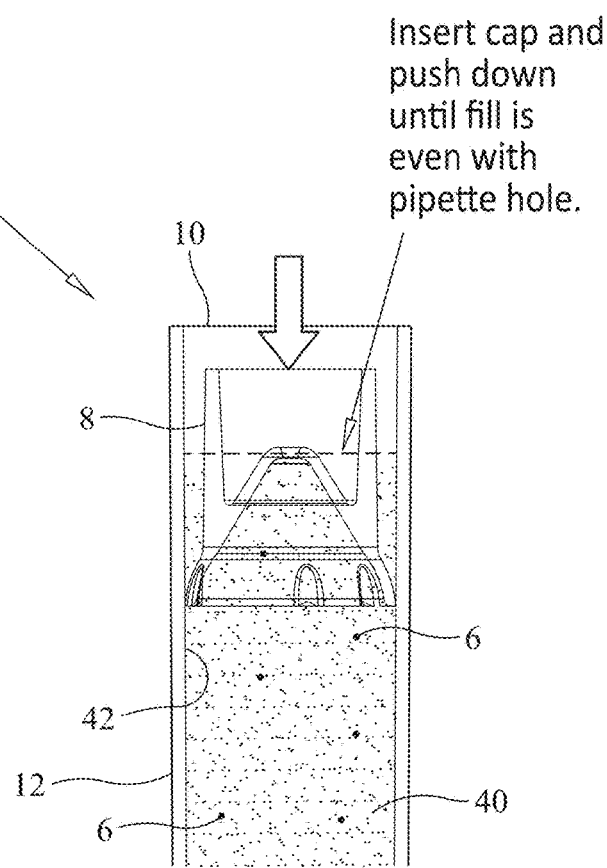
FIG. 5 is a detailed, cross-sectional view of the collection device of the present invention and the top portion of the test tube shown in FIG. 4, and illustrating a second step in a method of separating particles from a specimen contained in the test tube.

The lower skirt portion 20 of the plug 8 having the resilient flared sidewall 22 has a diameter which is the same as or slightly greater than the inner diameter of the test tube 12 in which the plug 8 is received so that the flared sidewall 22 closely engages the inner wall 42 of the test tube 12. The plug 8 is pushed down into the open end 10 of the test tube 12 until the surface of the fecal emulsion or slurry 40 is level with the pipetting port, as illustrated by FIG. 5 of the drawings. The cutouts 24 formed in the flared sidewall 22 of the lower skirt portion 20 permit some emulsion 40 to pass therethrough and into a gap 44 between the inner wall 42 of the test tube 12 and the tubular sidewall 16 of the upper portion 14 of the plug 8 in order to allow the plug 8 to be pushed into the open end 10 of the test tube 12 to a position where the emulsion or slurry 40 is level with the pipetting port 32. A removable cap (not shown) may be placed on the open end 10 of the test tube 12 above the plug 8 to prevent any spillage of fecal emulsion 40 when the test tube 12 is centrifuged.

Figure 6:
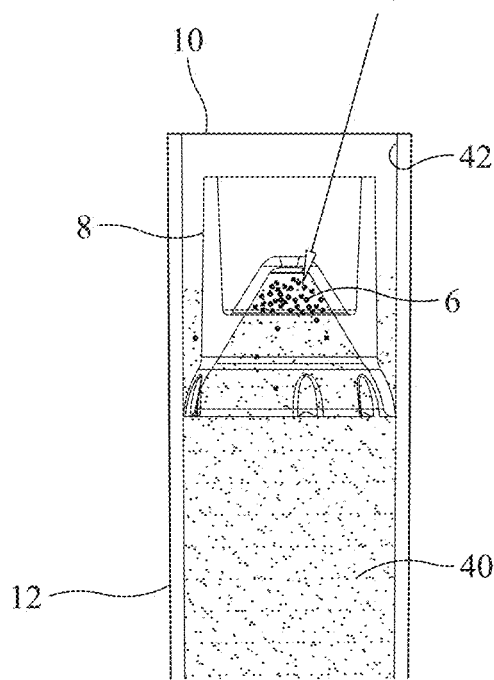
FIG. 6 is a detailed cross-sectional view of the collection device of the present invention and the top portion of the test tube shown in FIG. 4 and illustrating a third step in the method of separating particles from a specimen contained in the test tube.
Figure 7:
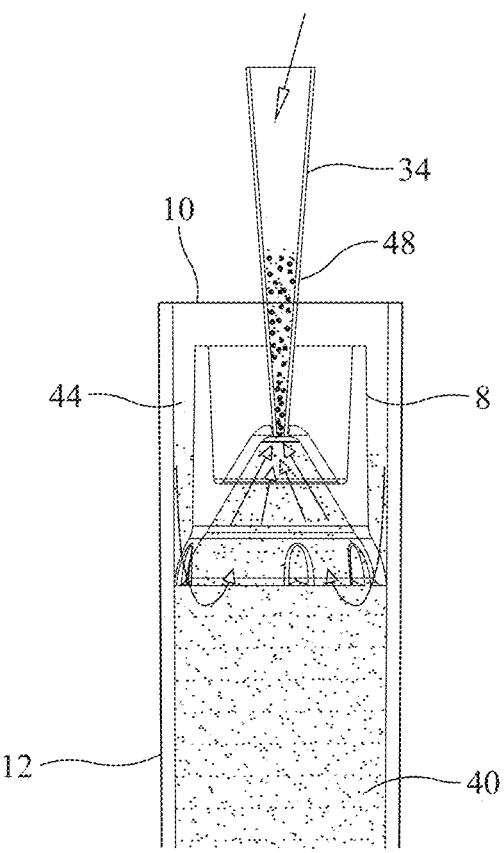
FIG. 7 is a detailed cross-sectional view of the collection device of the present invention and the top portion of the test tube shown in FIG. 4 and illustrating a fourth step in the process of separating particles from a specimen contained in the test tube.

The test tube 12, having the plug 8 mounted thereon, is now inserted into a centrifuge 46 (see FIG. 28), such as a swinging bucket-type laboratory centrifuge device, and spun for an appropriate time during which fecal matter and debris that have a greater density or specific gravity than that of the flotation solution are forced to the bottom of the tube 12, while the buoyant, lighter parasite ova or eggs 6 are forced to the surface of the solution. During and after centrifugation, the parasite ova and eggs 6 are directed by the conical shape of the inner wall 26 of the plug 8 to accumulate at the highest point in the funnel 28 defined by the inner wall 26 of the plug 8, as illustrated by FIG. 6 of the drawings. Then, and as shown in FIG. 7, the tip 34 of a pipette 36 may be inserted into the pipetting port 32 of the plug 8 to remove a predetermined volume of solution containing a concentrated quantity of separated parasite ova or eggs 6 by aspirating such into the pipette tip 34. Since a volume of solution is withdrawn from the test tube 12, the cutouts 24 formed in the flared sidewall 22 of the lower skirt portion 20 of the plug 8 allow the slurry or emulsion 40 in the gap 44 between the outer tubular sidewall 16 of the upper portion 14 of the plug 8 and the inner wall 42 of the test tube 12 to flow therethrough to take up the volume of fluid removed by the pipette 36. This equalizes the pressure of the emulsion 40 under the plug 8 and within the test tube 12 to allow the concentrated ova fluid to be aspirated into the pipette tip 34.

Figure 30:
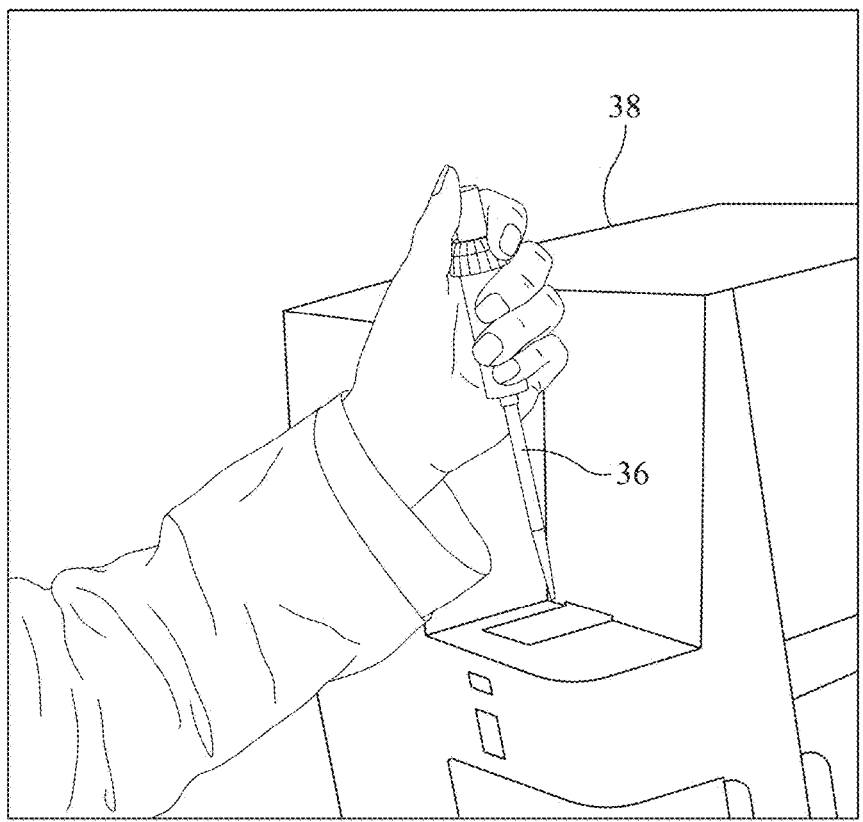
FIG. 30 is a perspective view illustrating a step in analyzing particles separated by the collection device of the present invention shown in either FIG. 2-7 or 8-29 in which the separated particles are transferred from a pipette to an automated clinical analyzer.
Figure 31:
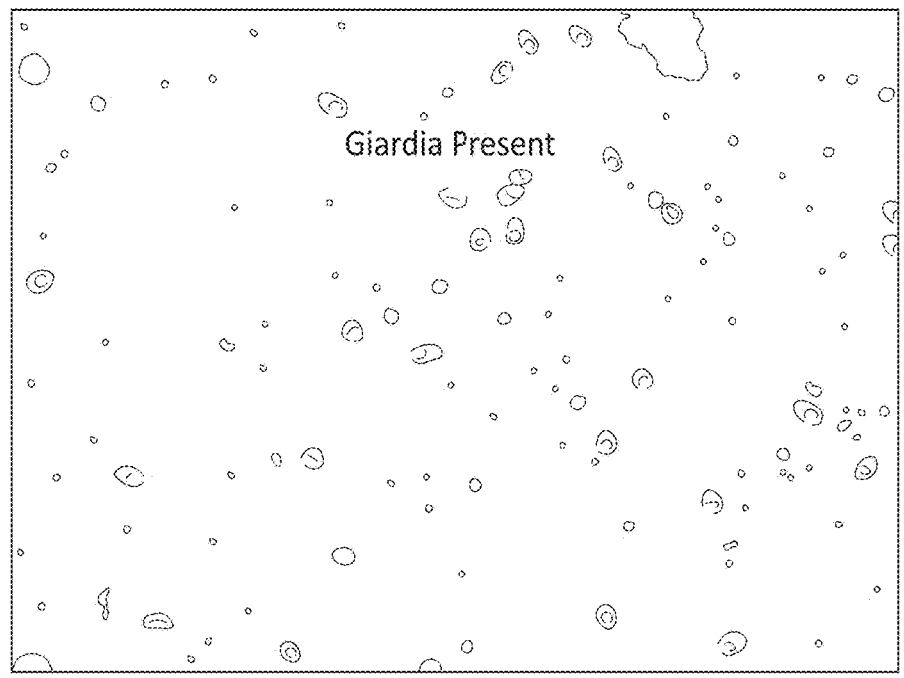
FIG. 31 is an optical photographic or pictorial illustration of a microscope test slide showing the presence of parasite ova or eggs in a fecal specimen.

The fluid 48 within the pipette tip 34, having a concentrated quantity of parasite cells 6, is transferred to a microscope slide and manually examined by a clinician in a laboratory using a microscope to determine whether or not parasite eggs or ova are present. Alternatively, the concentrated parasite cell fluid 48 may be transferred from the pipette tip 34 to an automated clinical analyzer 38, or to a cuvette designed for use in the IDEXX Sedivue Dx™ instrument mentioned previously, which optically determines whether such parasite ova or eggs are present, identify the type of parasite afflicting the patient, and count the quantity of eggs or ova that are detected to determine the severity of the parasite affliction, as illustrated by FIGS. 30 and 31 of the drawings. The aforementioned cuvette used with the IDEXX Sedivue Dx™ analyzer is depicted in U.S. Design Pat. No. D681,843 (Nemeth), the disclosure of which is incorporated herein by reference.

As will be explained in greater detail, the embodiments of the collection device 2 described herein need not be centrifuged but rather may simply be agitated and used in a passive flotation process for separating particles 6 from a specimen 4 in which, over a period of time, buoyant particles 6 will float to the top of the collection device 2 and accumulate in the funnel 28 of the plug 8.

A second embodiment of the collection device 2 of the present invention is shown in FIGS. 8-23 of the drawings, and its use in a centrifuge flotation process is illustrated by FIGS. 24A-31 of the drawings. More specifically, this second embodiment is a disposable, self-contained, centrifugable collection device 2 that simplifies obtaining a fecal specimen 4 by a pet owner and testing the specimen 4 by a laboratory clinician.

As shown in FIGS. 8-23, the collection device 2 includes a tubular body 50, or simply referred to herein as a tube, having opposite first and second axial ends 52, 54 (respectively, the bottom and top ends of the tube 50 shown in the figures), and formed with a generally cylindrical sidewall 56 that defines an interior bore 58 of the tube 50. On the first axial end 52 of the tubular body 50, which is open, is removably mounted a collection scoop assembly 60, and on the opposite second axial end 54 is mounted a particle accumulating plug 8.

Figure 8:
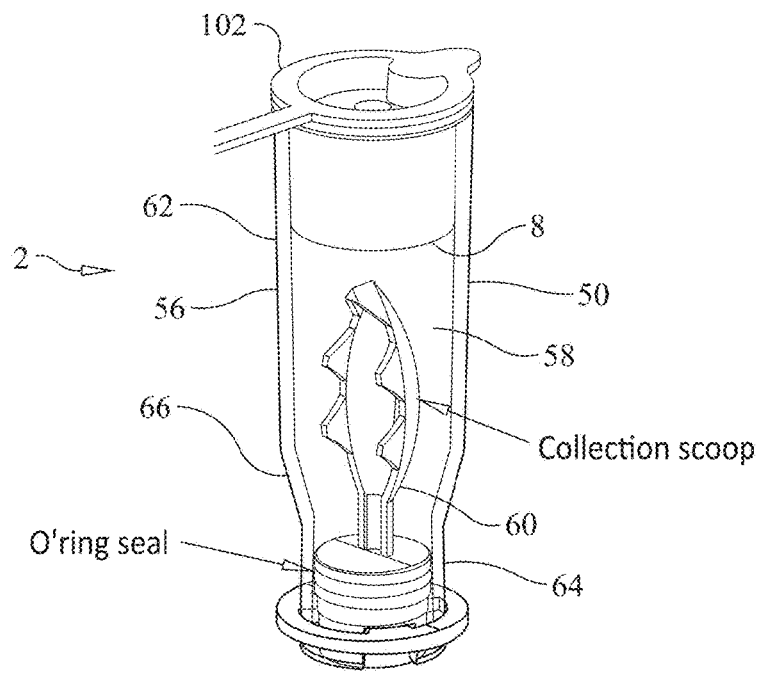
FIG. 8 is a perspective view of a second embodiment of a collection device constructed in accordance with the present invention and used for separating particles from a specimen.
Figure 9:
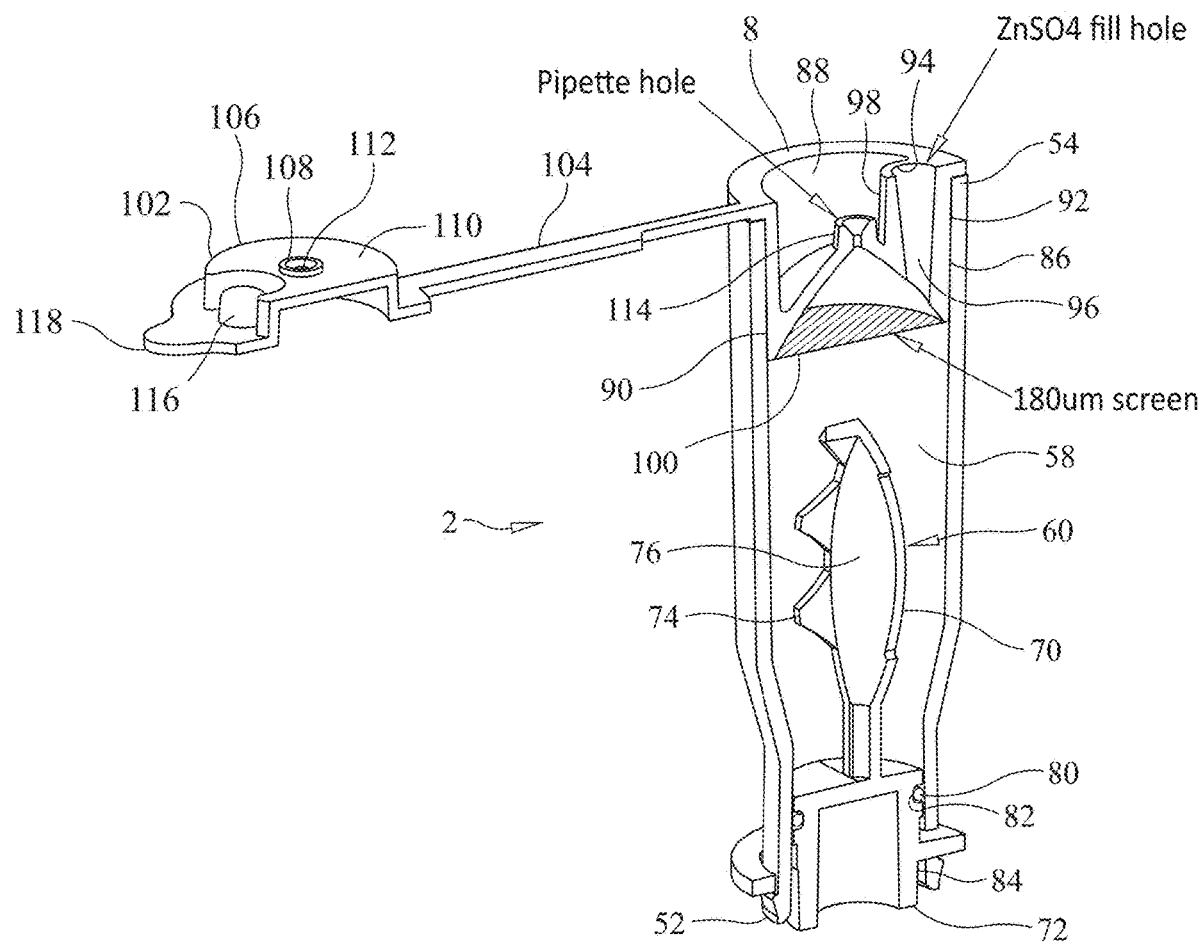
FIG. 9 is a partially cutaway, perspective view of the collection device of the present invention shown in FIG. 8.
Figure 10:
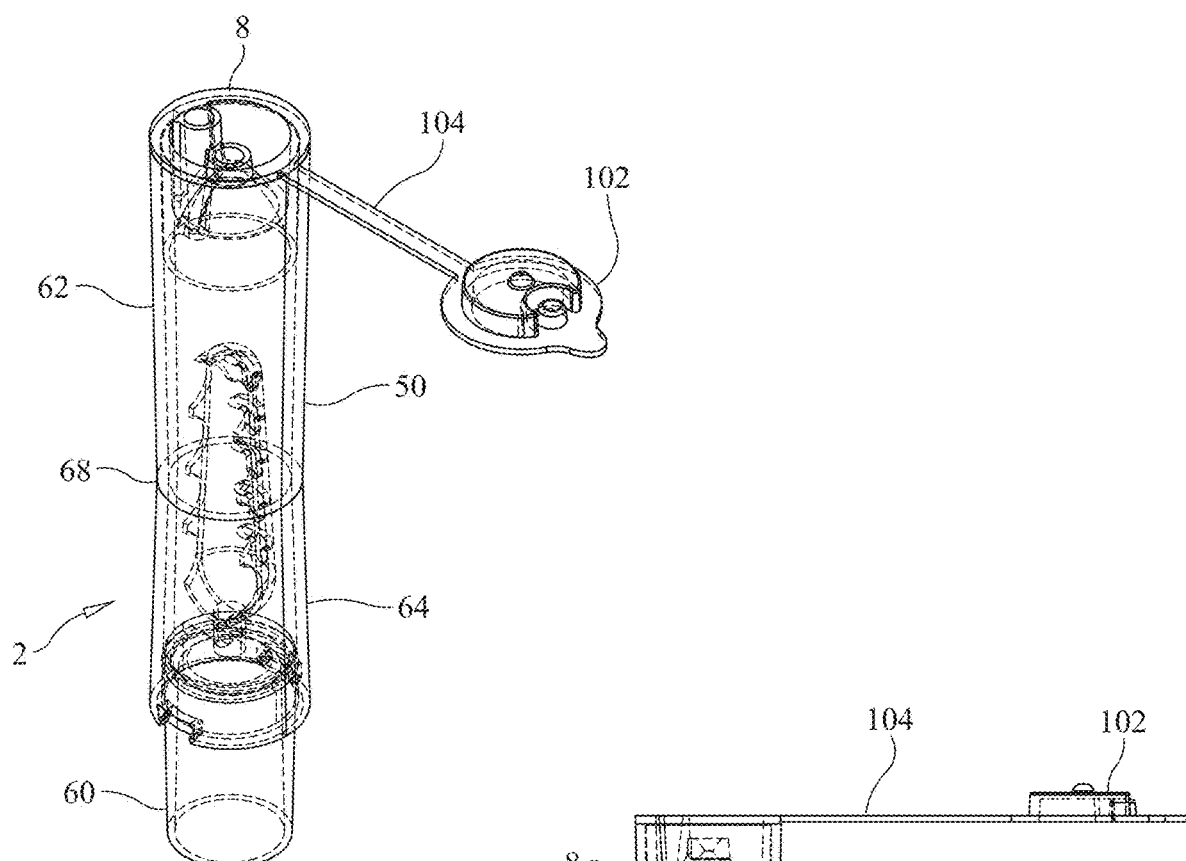
FIG. 10 is a perspective view, in cross-section, of the collection device of the present invention shown in FIGS. 8 and 9.

As shown in FIGS. 8 and 9, the tubular body, or tube 50, in one form of the present invention, includes an upper portion 62 where the particle accumulating plug 8 is mounted, a lower portion 64 in which the collection scoop assembly 60 is removably mounted and an intermediate tapered portion 66 situated between the upper portion 62 and the lower portion 64. More specifically, the sidewall 56 of the tube 50 that defines the upper portion 62, the intermediate portion 66 and the lower portion 64 has a larger diameter at the upper portion 62 than at the lower portion 64, with the intermediate portion 66 of the sidewall 56 converging from the upper portion 62 to the lower portion 64. Alternatively, and as shown in FIGS. 10-13, the tubular body, or tube 50, may be generally cylindrical with substantially the same diameter throughout its axial length, or may be slightly tapered inwardly from both the upper portion 62 and the lower portion 64 toward the mid-portion 68 of the tubular body 50. Preferably, the sidewall 56 of the tubular body 50 is transparent so that the clinician may see through the sidewall 56 into the interior bore 58 of the tube 50 to not only determine the level of the fecal emulsion or slurry 40 therein but also whether the emulsion 40 has been substantially agitated to reduce any clumps of fecal matter into the emulsion or slurry 40, as will be explained in greater detail. Another benefit of the transparent sidewall 56 is to allow the clinician or technician to note the macroscopic appearance and consistency of the sample without opening the tube 50. This is commonly notated in the medical record of the patient.

Figure 11:
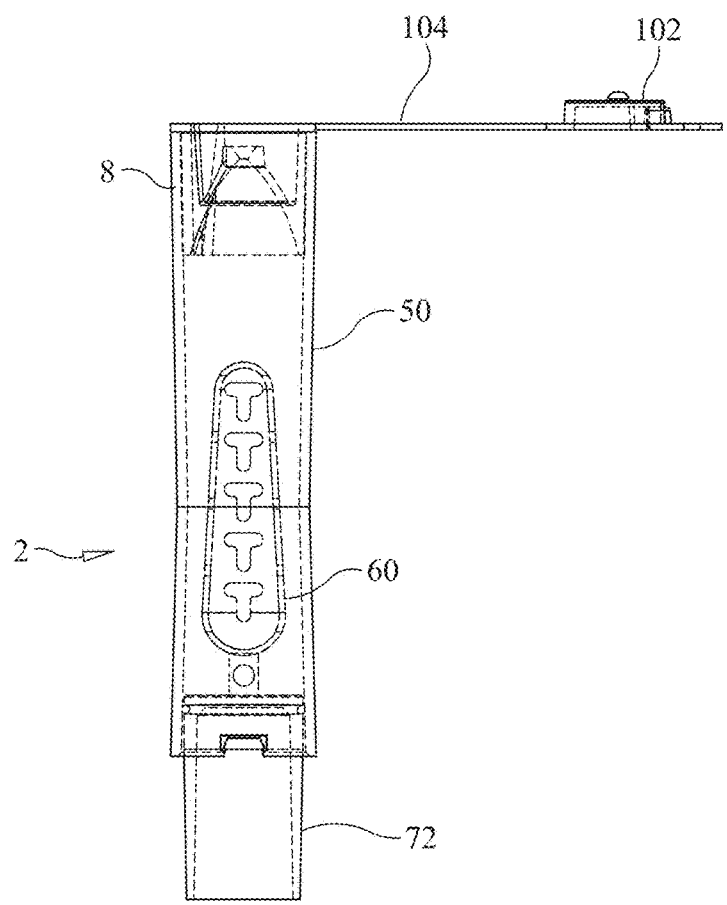
FIG. 11 is a side view, in partial cross-section, of the collection device of the present invention shown in FIGS. 8-10.
Figure 12:
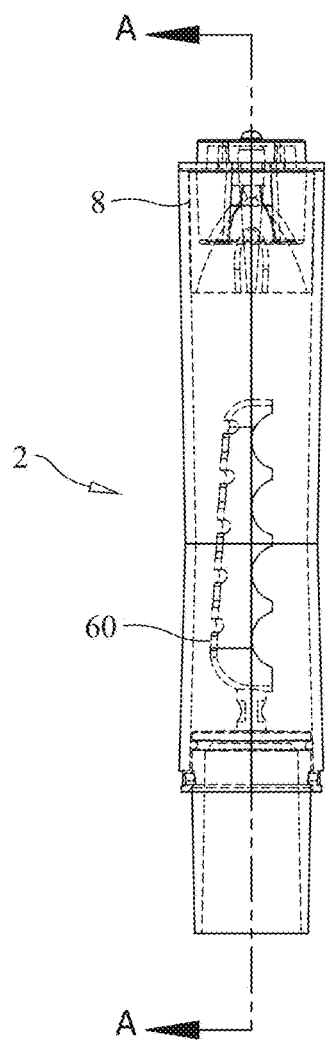
FIG. 12 is a side view, in partial cross-section, of the collection device of the present invention shown in FIGS. 8-11, taken from a different angle from that shown in FIG. 11.
Figure 13:
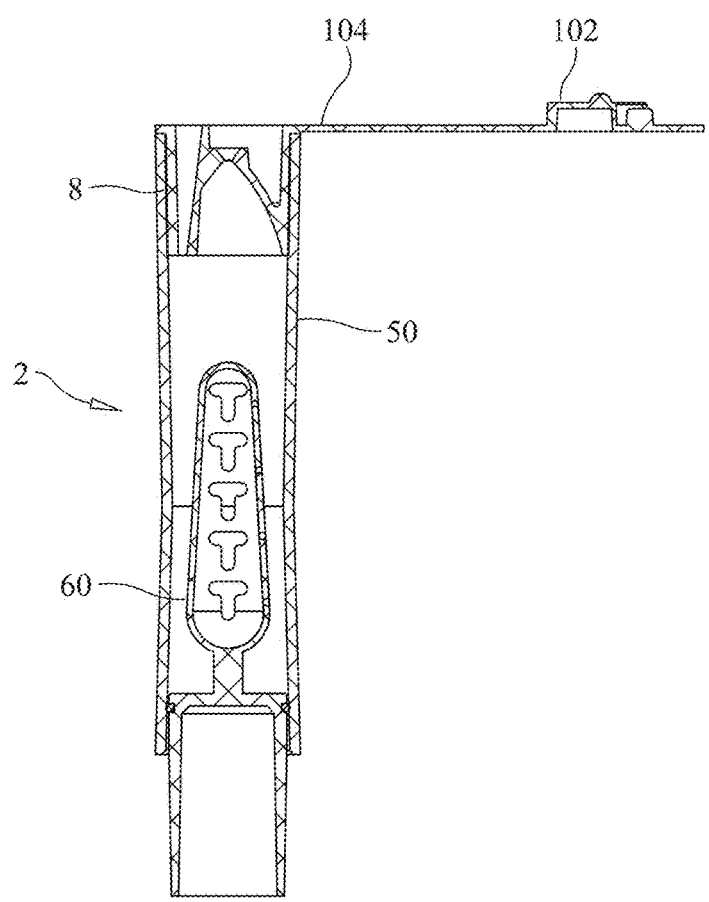
FIG. 13 is a longitudinal cross-sectional view of the collection device of the present invention shown in FIG. 8-12, taken along line A-A of FIG. 12.
Figure 14:
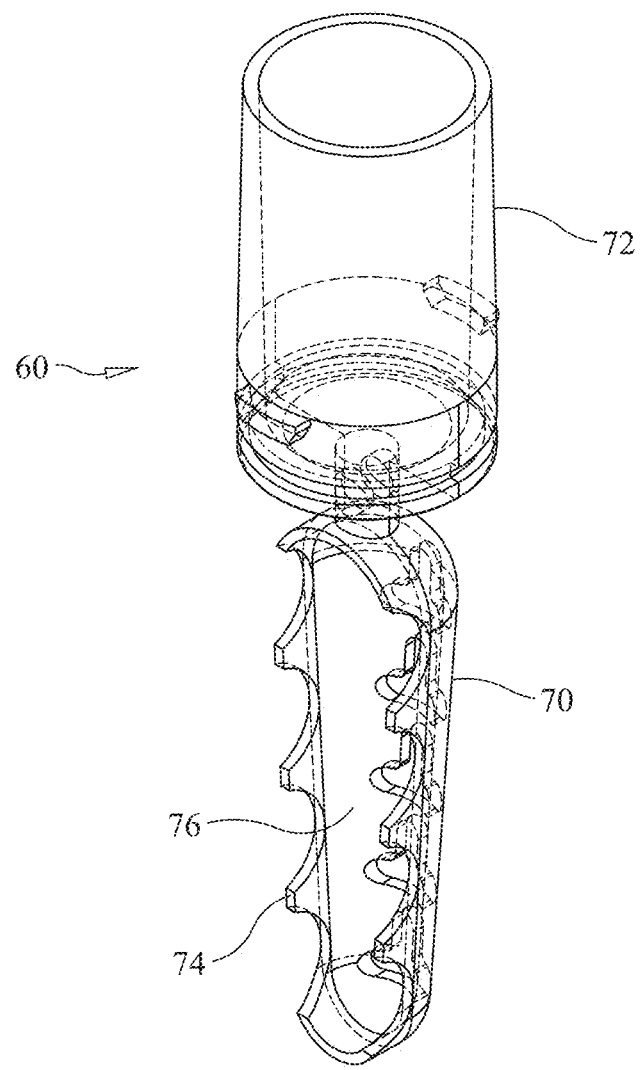
FIG. 14 is a perspective view, in partial cross-section, of the collection scoop assembly forming part of the collection device of the present invention shown in FIGS. 8-13.
Figure 15:
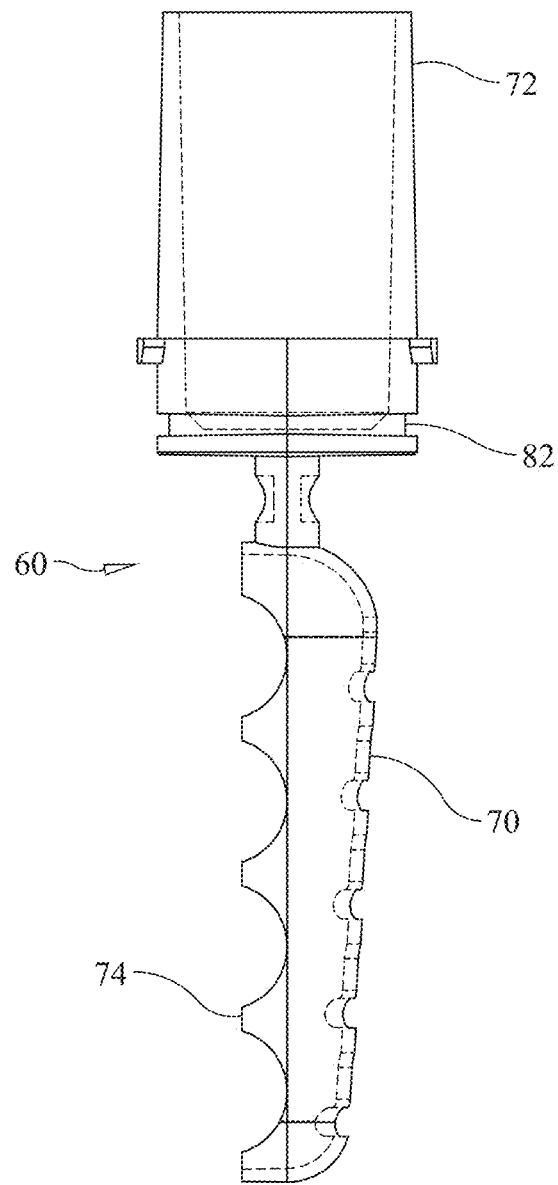
FIG. 15 is a side view, in partial cross-section, of the collection scoop assembly of the present invention shown in FIG. 14.
Figure 16:
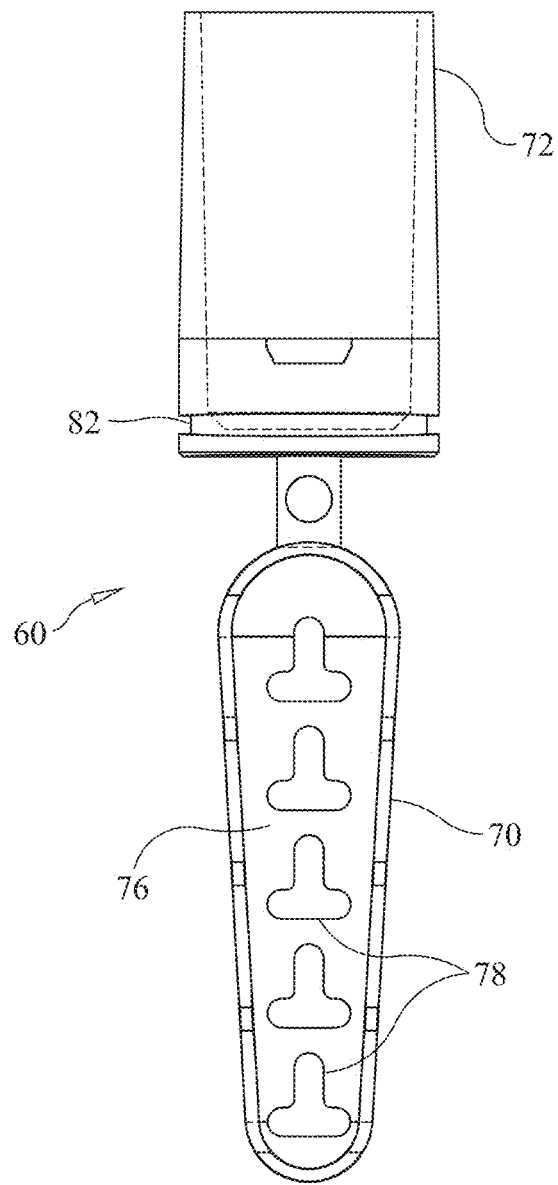
FIG. 16 is another side view, in partial cross-section, of the collection scoop assembly of the present invention shown in FIGS. 14 and 15, taken from a different angle than that of FIG. 15.
Figure 17:
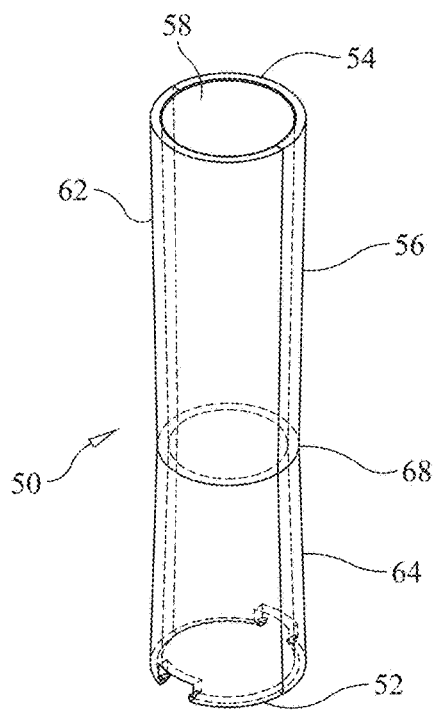
FIG. 17 is a perspective view, in partial cross-section, of the tubular body forming part of the collection device of the present invention shown in FIGS. 8-13.
Figure 18:
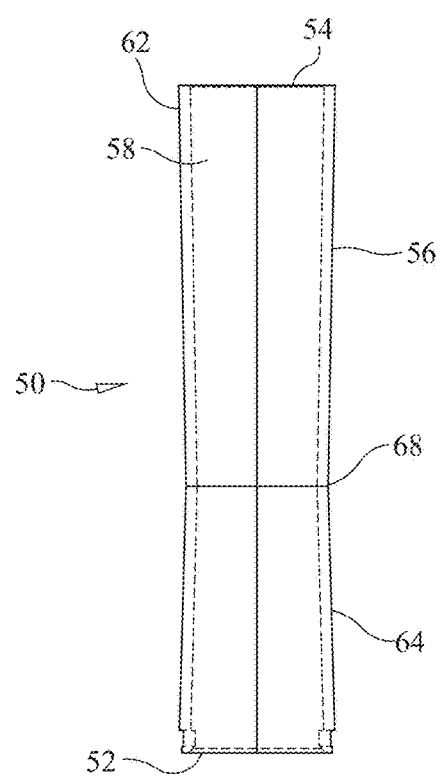
FIG. 18 is a side view, in partial cross-section, of the tubular body of the present invention shown in FIG. 17.
Figure 19:
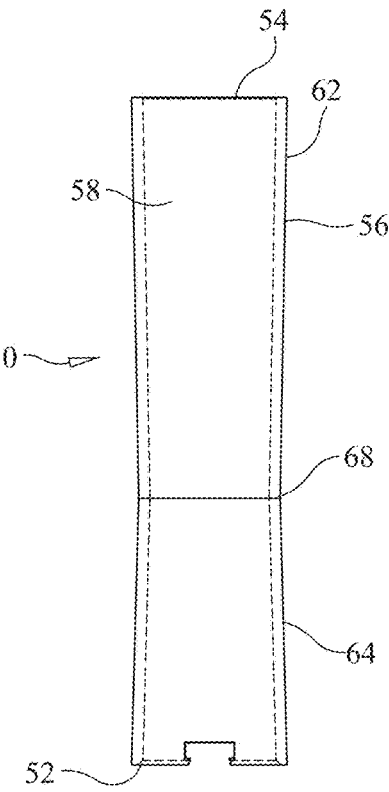
FIG. 19 is another side view, in partial cross-section, of the tubular body of the present invention shown in FIGS. 17 and 18, taken from a different angle than that of FIG. 18.
Figure 20:
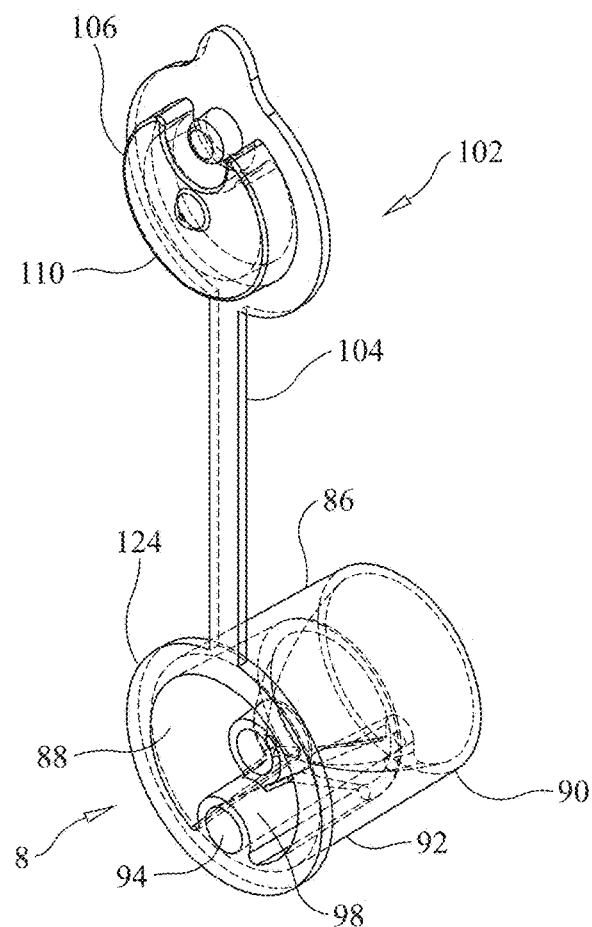
FIG. 20 is a perspective view, in partial cross-section, of the particle accumulating plug and flip cap forming part of the collection device of the present invention shown in FIGS. 8-13.
Figure 21:
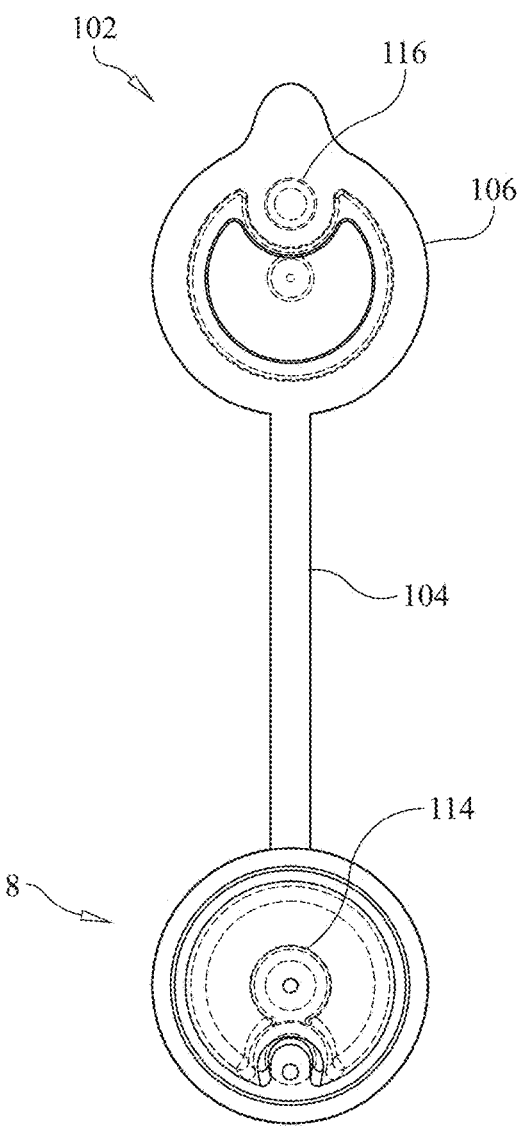
FIG. 21 is a top plan view, in partial cross-section, of the particle accumulating plug and flip cap of the present invention shown in FIG. 20.
Figure 22:
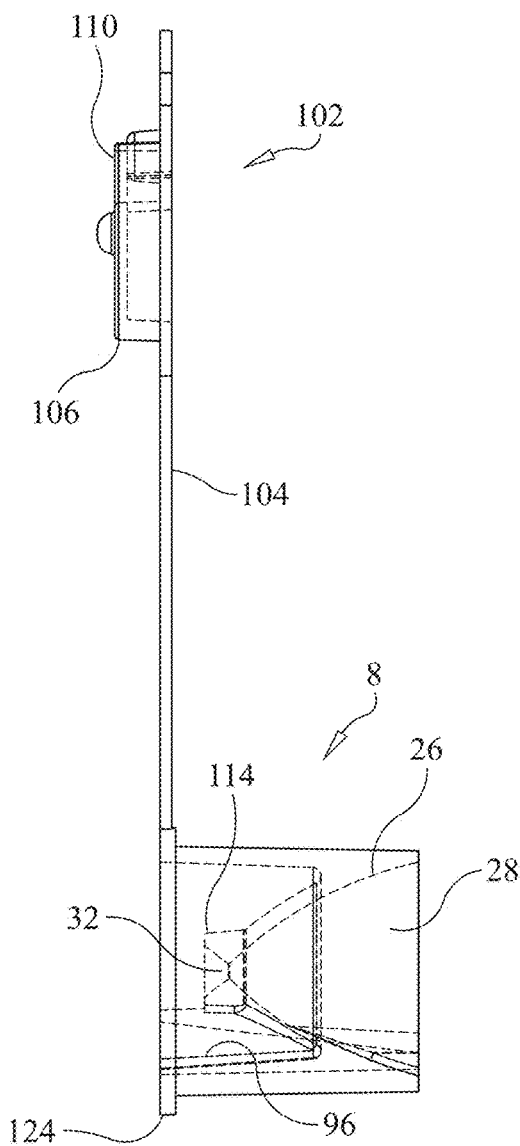
FIG. 22 is a side view, in partial cross-section, of the particle accumulating plug and flip cap of the present invention shown in FIGS. 20 and 21.
Figure 23:
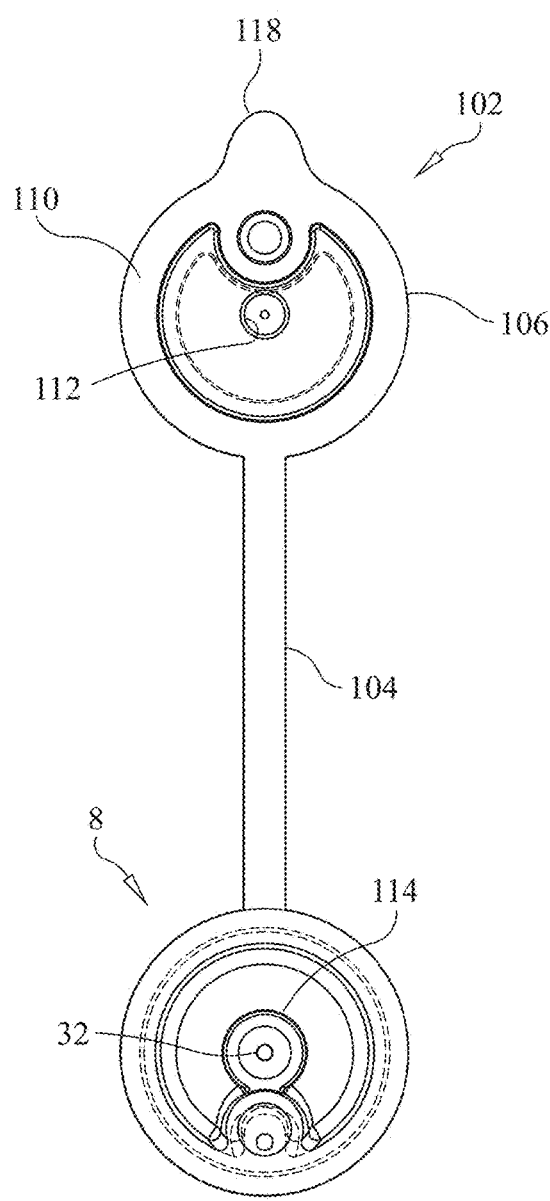
FIG. 23 is a bottom plan view, in partial cross-section, of the particle accumulating plug and flip cap of the present invention shown in FIGS. 20-22.

The collection scoop assembly 60 is particularly shown in FIGS. 8 and 9 in one version, and in FIGS. 14-16 in another version. The collection scoop assembly 40 includes a collection scoop 70, or spoon, that extends outwardly from a cylindrical handle 72. The collection scoop 70 includes spaced apart, peripheral edge teeth 74 surrounding a concave spoon portion 76 that helps retain a fecal specimen 4 in place on the scoop 70. The concave spoon portion 76 may further include a series of T-shaped cutouts 78 formed through the thickness thereof to further help retain the fecal specimen 4 in place on the scoop 70, as shown in FIGS. 11 and 13. The T-shaped cutouts 78 also provide access for the solution to get to the backside of the sample 4 to aid in getting it out of the scoop 70. The handle 72 of the collection scoop assembly 60 may be held by the pet owner or laboratory clinician for safely collecting a specimen 4 from the patient's feces. The outer diameter of the handle 72 is the same as or slightly smaller than the inner diameter of the sidewall 56 at the open first axial end 52 of the collection tube 50 so as to be closely received by the tube 50, with the collection scoop 70 extending axially into the bore 58 of the tube 50. Preferably, an O-ring 80 encircles the cylindrical handle 72 and is seated in a groove 82 formed in the sidewall 84 of the handle 72. The O-ring 80 forms a fluidtight seal with the tube 50 when the collection scoop assembly 60 is inserted into the first axial end 52 of the tube 50, and engagement between the handle of the collection scoop assembly 60 and the tube sidewall 56 at the first axial end 52 thereof produces an audible click that confirms to the user that the scoop assembly 60 is properly seated within the first axial end 52 of the tube 50.

Mounted on the second axial end 54 of the collection tube 50 is the particle accumulating plug 8. As shown in FIGS. 8 and 9 and FIGS. 20-23, the particle accumulating plug 8 includes a cylindrical outer sidewall 86, the diameter of which is chosen so that the outer surface of the sidewall 86 closely engages the inner surface of the tube sidewall 56 at the second axial end 54 thereof to form a fluidtight seal therewith. Alternatively, the diameter of the outer sidewall 86 of the plug 8 may be chosen to be slightly less than the inner diameter of the tube 50 at the second axial end 54 thereof in which the plug 8 is received to define a gap or space between the outer sidewall 86 of the plug 8 and interior surface of the tube 50. This gap or space may be provided to receive "overflow" flotation solution from the interior bore 58 of the tube 50 so that, when flotation solution carrying parasite eggs or ova is withdrawn from the collection tube 50 by the pipette tip 34, the solution withdrawn will be replaced by the "overflow" solution residing in the gap or space between the outer sidewall 86 of the plug 8 and the inner sidewall of the collection tube 50, the overflow solution flowing back into the interior bore 58 of the tube 50 from the gap or space between the plug 8 and tube sidewall. In addition, the plug 8 may be formed with a lip or flange 124 extending radially outwardly from the outer sidewall 86 of the plug 8 at the upper portion 92 thereof, the lip or flange 124 resting on the edge of the tube 50 at the second axial end 54 thereof. This lip or flange 124 acts as a stop to prevent the plug 8 from being over-inserted into the second axial end 54 of the tube 50 when the collection device 2 is being assembled and, in one embodiment, may form a fluidtight seal between the plug 8 and the tube 50.

The outer sidewall 86 of the particle accumulating plug 8 defines an interior bore 88. The particle accumulating plug 8 further includes an inner wall 26 formed with a generally conical shape that defines an inverted funnel 28, similar in many respects to the design of the particle accumulating plug 8 of the first embodiment described previously and shown in FIGS. 2-7 of the drawings. The conically-shaped inner wall 26 extends upwardly into the bore 88 from the lower portion 90 of the plug 8 towards the upper portion 92 of the plug 8. As with the first embodiment, a pipetting port 32 is formed in and through the thickness of the conical inner wall 26 of this second embodiment of the plug 8 near where the conical wall 26 converges to form the apex 30 of the inverted funnel 28. Preferably, the outer sidewall 86 of the plug 8 and the conically-shaped inner wall 26 are transparent, like the sidewall 56 of the tubular body 50, so that a clinician may see through the tubular body sidewall 56 and the outer sidewall 86 and inner wall 26 of the plug 8 to determine the level of the flotation solution or emulsion 40 within the bore 58 of the tubular body 50 and whether that level has reached the height of the pipetting port 32 after additional solution has been added prior to centrifugation, as will described in greater detail.

The particle accumulating plug 8 further includes a fill port 94 formed therein that leads to and communicates with a cylindrical or funnel-shaped fill bore 96 defined by a second, longitudinally extending, inner wall 96 of the plug 8. The fill port 94 and fill bore 96 allow a flotation solution to be added to the bore 58 of the collection tube 50, which solution exits the fill bore 96 below or near the lower extent of the conically-shaped inner wall 26 so as not to disturb any separated particles accumulating within the inverted funnel portion 28 of the plug 8 defined by the conically-shaped inner wall 26. Furthermore, the plug 8 may include a screen or filter medium 100 extending across the diameter of the plug 8 at the lower portion 90 thereof and which may have a multiplicity of pores of about 180 microns in diameter or in general dimensions formed therethrough to allow separated particles 6, such as parasite ova and eggs, to pass freely therethrough and to filter out any fecal clumps and undigested vegetable matter which may be contained in the fecal specimen 4 and which would have otherwise floated to the surface of the liquid 40 contained in the collection tube 50 along with the ova and eggs 6 into the volume defined by the funnel shape of the conical wall 26 of the plug 8.

A removable flip cap 102 is attached to the particle accumulating plug 8 with an extended living hinge 104. The flip cap 102 includes a cylindrical main body 106, and a boss 108 extending outwardly from the lower surface 110 of the main body 106 that surrounds a recess 112 formed therein, the boss 108 and recess 112 receiving a cylindrical protrusion 114 surrounding the pipetting port 32 formed in the conically-shaped inner wall 26 of the plug 8 to seal the pipetting port 32 when the flip cap 102 is mounted on the upper portion 92 of the particle accumulating plug 8. Additionally, the flip cap 102 includes a protrusion 116 extending outwardly from a lower surface 110 of the main body 106 of the cap 102 which is received by and acts as a stopper for the flotation solution fill port 94 formed in the plug 8 when the flip cap 102 is mounted on the plug 8. The flip cap 102 also includes a tab 118 extending radially from the main body 106 thereof which serves as a handle for the clinician to grasp when removing the flip cap 102 from the particle accumulating plug 8. The flip cap 102 fluidically seals the pipetting port 32 and fill port 94 of the plug 8 when properly mounted thereon.

Figures 24A, 24B:
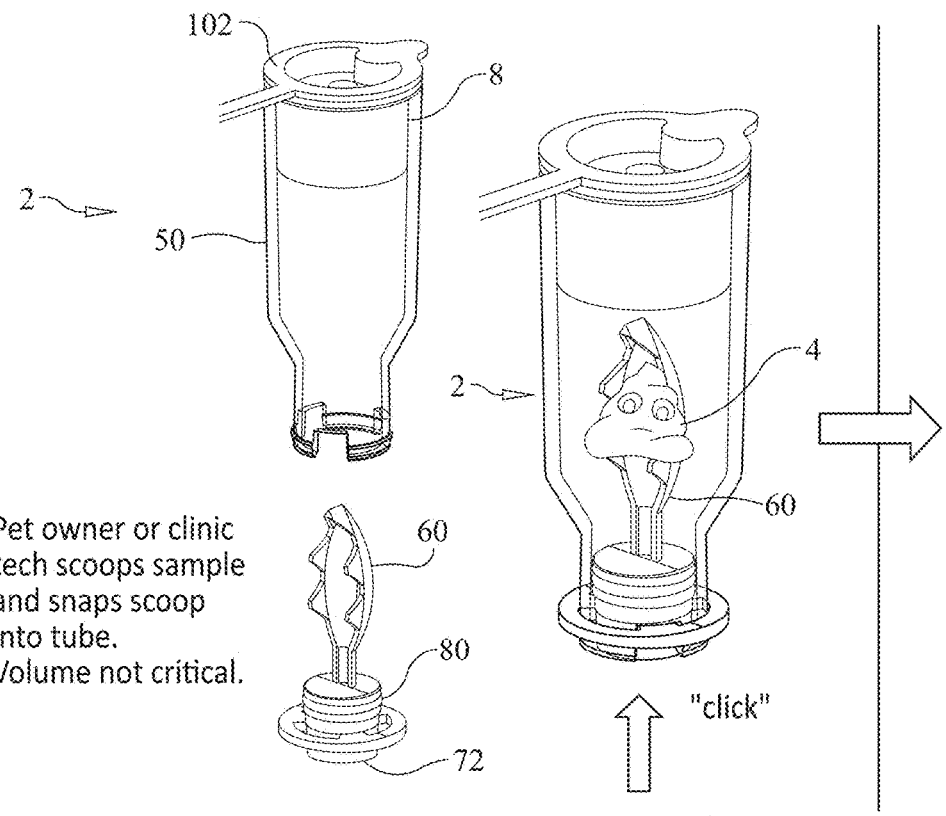
FIG. 24A is a partially exploded, perspective view of the collection device of the present invention shown in FIGS. 8-13, and illustrating a first step in a method for separating particles from a specimen.
FIG. 24B is a perspective view of the collection device of the present invention shown in FIGS. 8-13, and illustrating a second step in a method for separating particles from a specimen.

FIGS. 24A-31 illustrate how this second embodiment of the collection device 2 formed in accordance with the present invention may be used in a centrifuge flotation method for examination of a fecal specimen 4 to determine whether or not a patient is afflicted with parasites. Initially, the pet owner or clinic technician removes the collection scoop assembly 60 from the bottom end 52 of the collection tube 50, as shown in FIG. 24A, and holds the handle 72 of the collection scoop assembly 60 to scoop a fecal specimen 4 from the patient's feces. The peripheral edge teeth 74 and plurality of T-shaped cutouts 78 formed in the scoop 70 hold the specimen 4 in place on the spoon portion 76 of the assembly 60. Then, the pet owner or laboratory clinician replaces the collection scoop assembly 60, with the fecal specimen 4 adhering thereto, back into the open bottom end 52 of the collection tube 50, as shown in FIG. 24B. The O-ring 80 on the handle 72 of the collection scoop assembly 60 forms a fluidtight seal with the collection tube 50 to prevent fluid from leaking therefrom.

Figure 25:
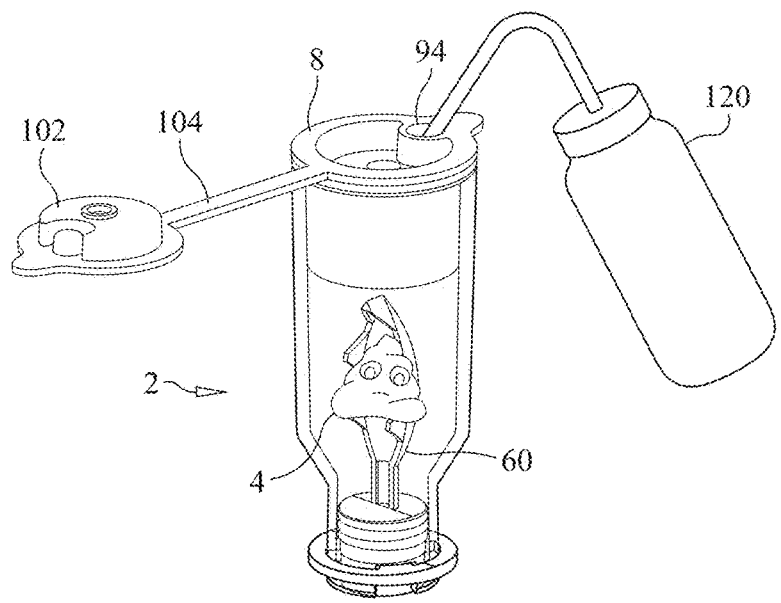
FIG. 25 is a perspective view of the collection device of the present invention shown in FIGS. 8-13, and illustrating a third step in a method for separating particles from a specimen.
Figure 26:
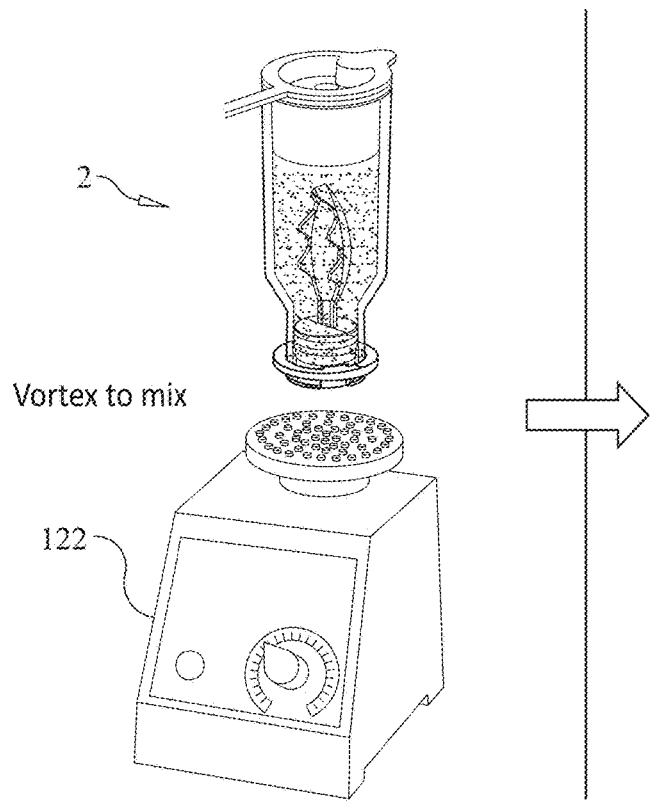
FIG. 26 is a perspective view of the collection device of the present invention shown in FIGS. 8-13, and illustrating a fourth step in a method for separating particles from a specimen.

As shown in FIG. 25, the clinician opens the flip cap 102 and fills the bore 58 of the collection tube 50 with a flotation solution 120, such as a zinc sulfate solution or magnesium sulfate solution, through the fill port 94 formed in the particle accumulating plug 8. The flip cap 102 is then replaced on the particle accumulating plug 8 to seal the pipetting port 32 and fill port 94 and to prevent any leakage therefrom. Then, the clinician mixes the fecal specimen 4 and flotation solution 120 by vigorously shaking the collection device 2, or by using an automated agitator 122, such as shown in FIG. 26, such that a fecal emulsion or slurry 40 is formed within the collection tube 50.

Figure 27:
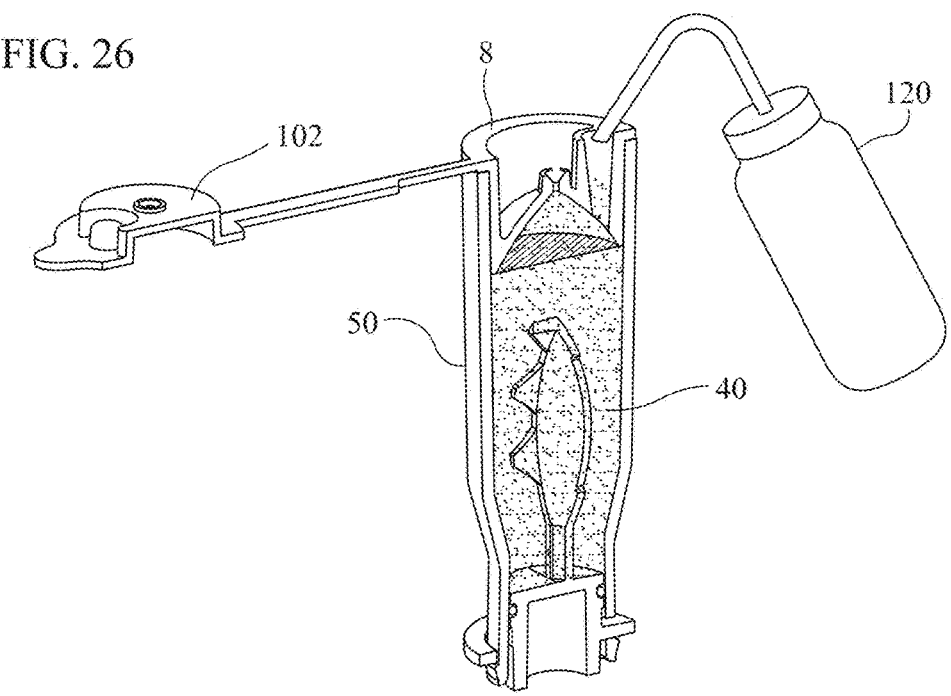
FIG. 27 is a perspective view of the collection device of the present invention shown in FIGS. 8-13, and illustrating a fifth step in a method for separating particles from a specimen.

After the collection device 2 is sufficiently agitated to fully mix the fecal specimen 4 with the flotation solution 120, the flip cap 102 is again removed from the plug 8, and additional flotation solution 120 is added through the fill port 94 until the level of the emulsion or slurry 40 in the tube 50 reaches the pipetting port 32, as shown in FIG. 27. The flip cap 102 is then replaced on the particle accumulating plug 8. It should be note that this "topping off" step of adding additional flotation solution 120 to the collection device 2 to bring the fluid in the collection device 2 up to a desired level may occur after the collection device 2 is centrifuged.

Figure 28:
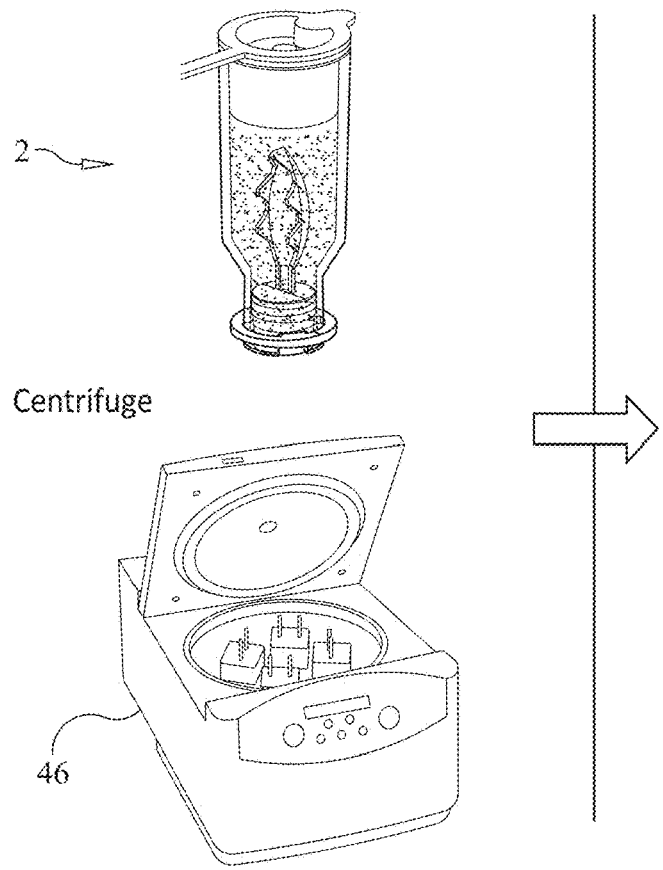
FIG. 28 is a perspective view of the collection device of the present invention shown in FIGS. 8-13, and illustrating a sixth step in a method for separating particles from a specimen.

Next, and as shown in FIG. 28, the collection device 2 is centrifuged preferably using a fixed angle-type centrifuge device, or swinging bucket-type centrifuge device, or other type of centrifuge device 46 commonly used in clinical laboratories. The collection device 2 is spun for an appropriate time, preferably about five minutes, during and after which fecal matter and debris in the emulsion 40 that have a higher density or specific gravity than that of the flotation solution 120 are forced to the bottom 64 of the tube 50, while the lighter, buoyant parasite ova and eggs 6, or other cells, are forced to the surface of the fluid through the screen or filter 100 attached to the bottom of the plug 8. The conically-shaped inner wall 26 of the plug 8 directs the separated ova and eggs 6 towards the pipetting port 32 and the volume within the inverted funnel 28 of the plug 8 defined by the conically-shaped inner wall 26.

Figure 29:
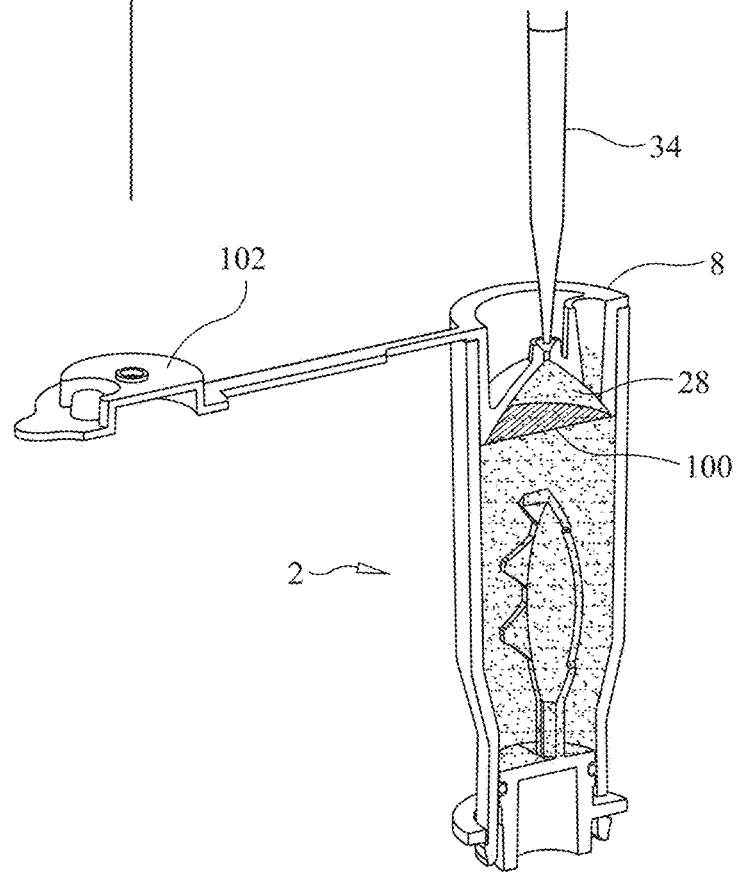
FIG. 29 is a perspective view of the collection device of the present invention shown in FIGS. 8-13, and illustrating a seventh step in a method for separating particles from a specimen.

In the next step of the centrifuge flotation process using the collection device 2 of the present invention, and as shown in FIG. 29 of the drawings, the flip cap 102 is removed from the particle accumulating plug 8 to expose the pipetting port 32, and the tip 34 of the pipette 36 is inserted into the port 32 to aspirate into the pipette tip 34 a desired volume of fluid 48 containing a concentrated quantity of parasite ova and eggs 6, or other cells. After the pipetting step has been completed, the flip cap 102 may be replaced on the plug 8, and the collection device 2 may be safely disposed of in accordance with proper medical protocols.

Figure 1:
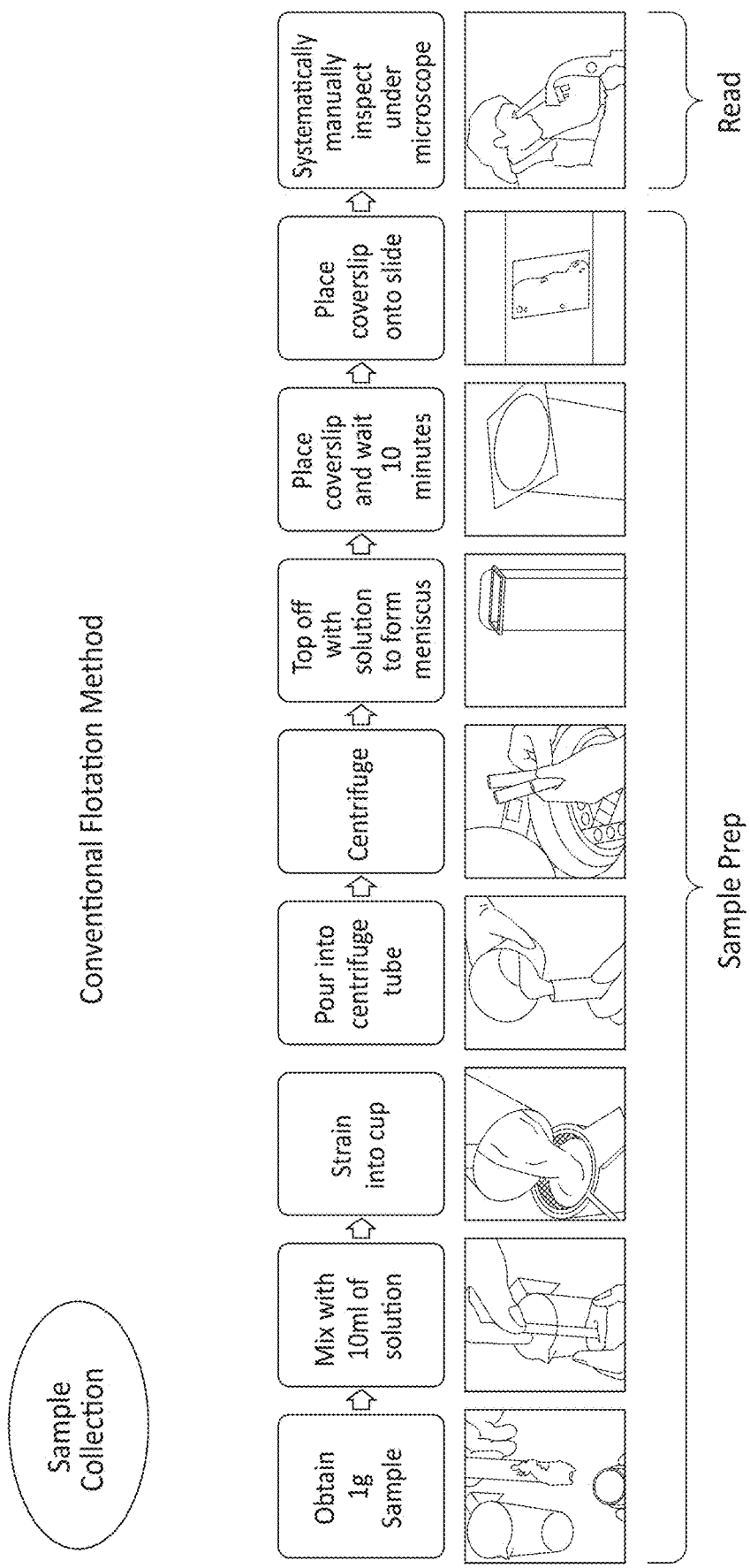
FIG. 1 is a series of illustrations showing a conventional flotation method for determining whether or not a patient is afflicted with parasites.

The fluid 48 in the pipette tip 34, having a concentrated quantity of parasite ova and eggs 6, or other cells, may be transferred to a microscope slide for manual examination by a technician using a microscope, as shown in the last illustration of FIG. 1, or may be deposited in an automated clinical analyzer 38, such as the Sedivue Dx™ analyzer available from IDEXX Laboratories, Inc. mentioned previously, as shown in FIG. 30, to determine whether parasite ova or eggs are present, and to identify the type of parasite afflicting the patient from an examination of the ova or eggs, or to determine the seriousness of the infestation by counting and recording the number of each type of ova or eggs. FIG. 31 is an optical photograph taken by the Sedivue Dx™ analyzer 38 which shows the presence of parasite cells and confirms that the patient is afflicted with parasites.

It should be noted that the collection device 2 of the present invention may be used in a passive flotation process, that is, by allowing the buoyant particles 6 to float to the surface of the emulsion 40 after the sample 4 and the flotation solution are thoroughly mixed but without centrifugation. After agitation of the collection device 2, as illustrated by FIG. 26, the collection device 2 is allowed to rest for a predetermined period of time, for example ten minutes, so that the lighter, buoyant separated particles 6 will float to the surface of the emulsion 40 and be directed by the conically-shaped inner wall 26 of the plug 8 to accumulate within the funnel volume and at the pipetting port 32 for removal therefrom using a pipette 36.

The particle accumulating plug 8 in each of the embodiments of the collection device 2 of the present invention shown in FIGS. 2-7 and 8-29 may be formed from aluminum, or even more preferably, from a plastic material, such as polypropylene or high density polyethylene, but is preferably formed or treated to be hydrophilic. More specifically, the surface of the plug 8 may be treated with polyvinylpyrrolidone (also referred to as "polyvidone" or "povidone") or be subjected to a corona treatment to provide or enhance the plug's surfaces with hydrophilic properties. Or, the surfaces of the plug 8 may be coated with a surfactant or wetting agent. Such surface treatments can improve the ability of the plug 8 to recover and accumulate particles 6 from the sample emulsion or slurry 40.

The collection device 2 of the present invention simplifies the separation and collection of particles 6 in a passive or centrifuge flotation method. With the collection device 2 of the present invention, there is no need to allow the device 2 to rest after topping off the device 2 with flotation solution 120, since the fill bore 96 communicating with the fill port 94 extends below the level of any particles 6 accumulating in the conically-shaped funnel portion of the plug 8. As mentioned previously, with conventional collection tubes that must be filled to the top by adding fluid to the tube after centrifugation to form a meniscus on which a coverslip is placed so that parasite ova and eggs may adhere thereto, the tube must rest for about ten minutes after the fluid addition to allow the ova or eggs disturbed by the addition of fluid to reascend to the fluid surface. Such rest time is not required with the collection device 2 of the present invention, as the addition of solution 120 will not disturb the separated particles 6 accumulating in the plug 8.

Furthermore, the conical shape of the inner wall 26 of the plug 8 directs the separated particles 6 to accumulate in the funnel 28 at the pipetting port 32, and fluid thereat having a concentrated quantity of parasite cells 6 may easily be removed from the funnel volume where the particles 6 accumulate by using a pipette 36. Aspirating the accumulated parasite cells 6 into the pipette tip 34 will result in a greater quantity of parasite cells per unit volume of fluid extracted in this manner, much more than would be obtained with the conventional flotation method using a coverslip to which the buoyant parasite cells at the fluid surface must adhere.

Figure 32:
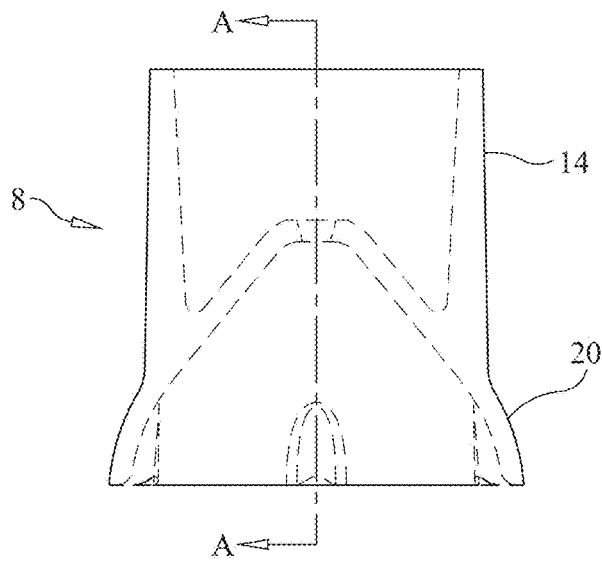
FIG. 32 is a side elevational view, shown in phantom, of the particle accumulating plug of the present invention shown in FIGS. 2 and 3.
Figure 33:
FIG. 33 is a cross-sectional view of the particle accumulating plug shown in phantom in FIG. 32, taken along line A-A of FIG. 32.
Figure 33:
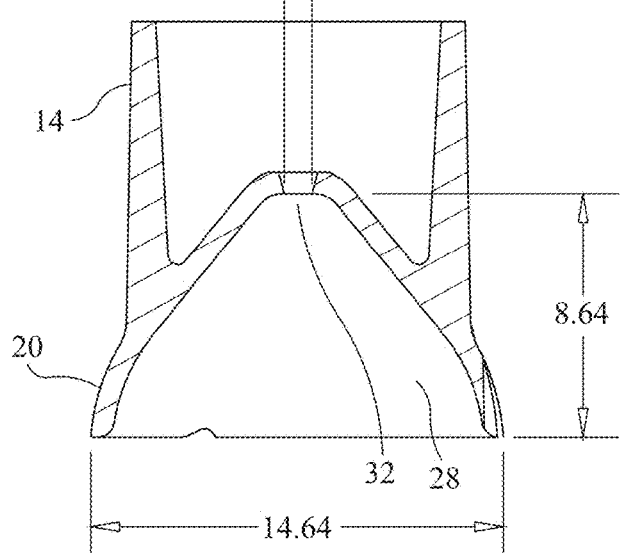
Figure 34:
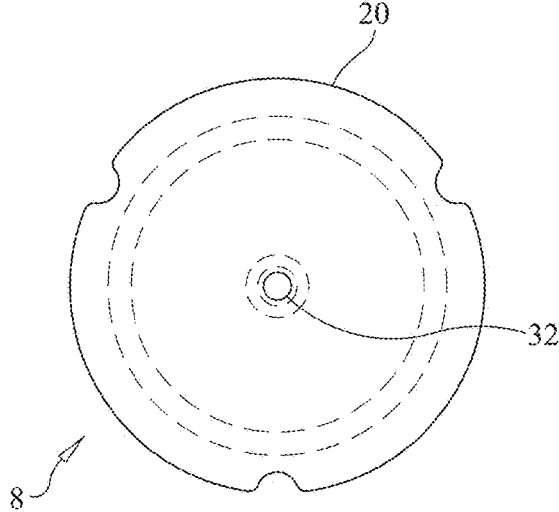
FIG. 34 is a transverse cross-sectional view of the particle accumulating plug of the present invention shown in FIG. 32.

A preferred form of the first embodiment of the particle accumulating plug 8 shown in FIGS. 2-7 of the drawings is further illustrated with preferred dimensions in FIGS. 32-34. As shown in FIG. 33, the overall interior axial length of the conically-shaped inner wall 26 measured within the inverted funnel 28 from the bottom edge of the skirt 22 to where the pipetting port 32 is formed in the inner wall 26 is preferably about 8.64 millimeters. The outer diameter of the plug 8 measured at the bottom edge of the skirt 22 is preferably about 14.64 millimeters, and the inner diameter of the bore of the pipetting port 32 is preferably about 1 millimeter, although the port diameter may vary according to the outer diameter of the pipette tip 34 received thereby and could be, for example, in the range of about 0.5 millimeters to about 2 millimeters.

The angle of the conically-shaped inner wall 26 of the plug 8, measured from the central axis of the plug 8, may vary depending upon the type of particles to be separated by the collection device 2 of the present invention, and as an example, could range from about 5 degrees to about 60 degrees or, more preferably, from about 9 degrees to about 50 degrees and, optimally, about 9.6 degrees or about 10 degrees, for separating parasite eggs and ova. Parasite eggs and ova, cells and other particles will have varying buoyancies and "stickiness" to the inner wall 26 of the plug 8, and the preferred angle of the conically-shaped inner wall 26 is selected at least in part based on such attributes of the particles to be separated. The general outer diameter of the plug 8 is chosen based on the inner diameter of the collection tube 12 into which the plug 8 is received, and the overall axial length of the plug 8 is driven by the plug diameter and the preferred angle or slope of the conically-shaped inner wall 26.

Figure 35:
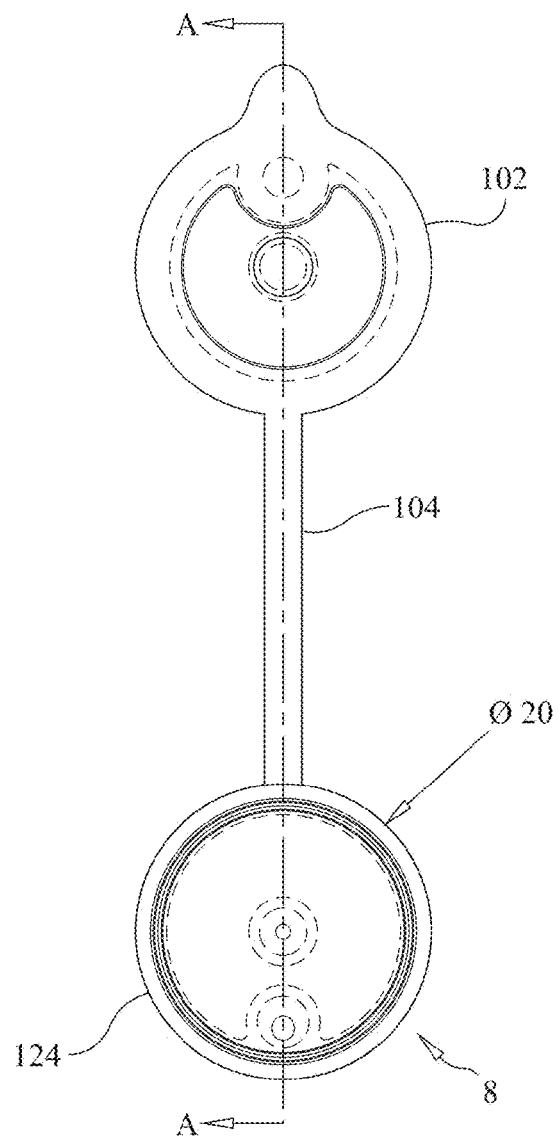
FIG. 35 is a top plan view of the particle accumulating plug and flip cap of the present invention shown in FIGS. 20-23.
Figure 36:
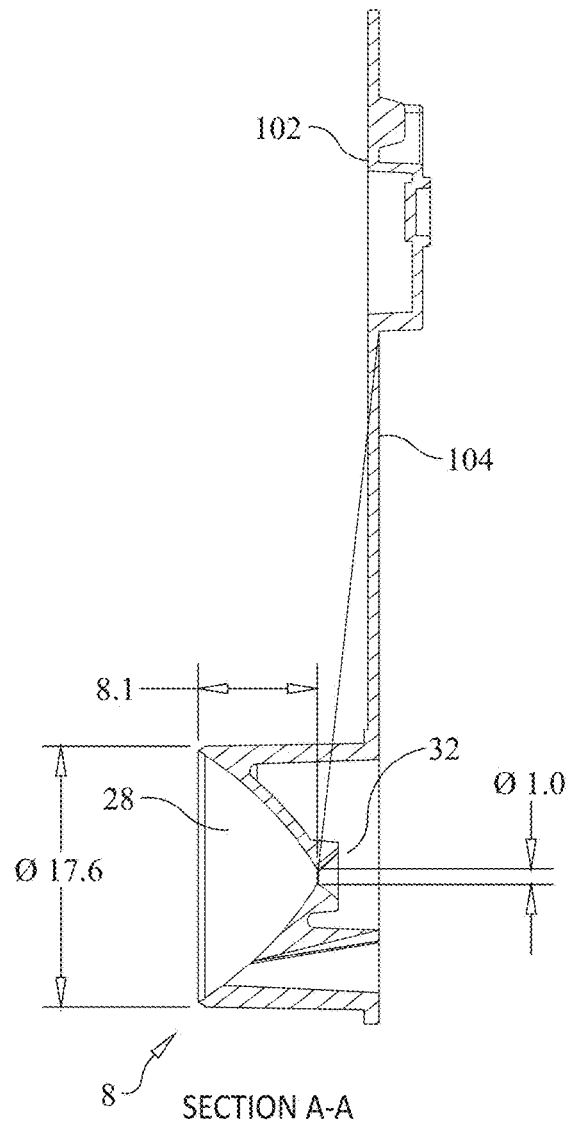
FIG. 36 is a cross-sectional view of the particle accumulating plug and flip cap of the present invention shown in FIG. 35, taken along line A-A of FIG. 35.
Figure 37:
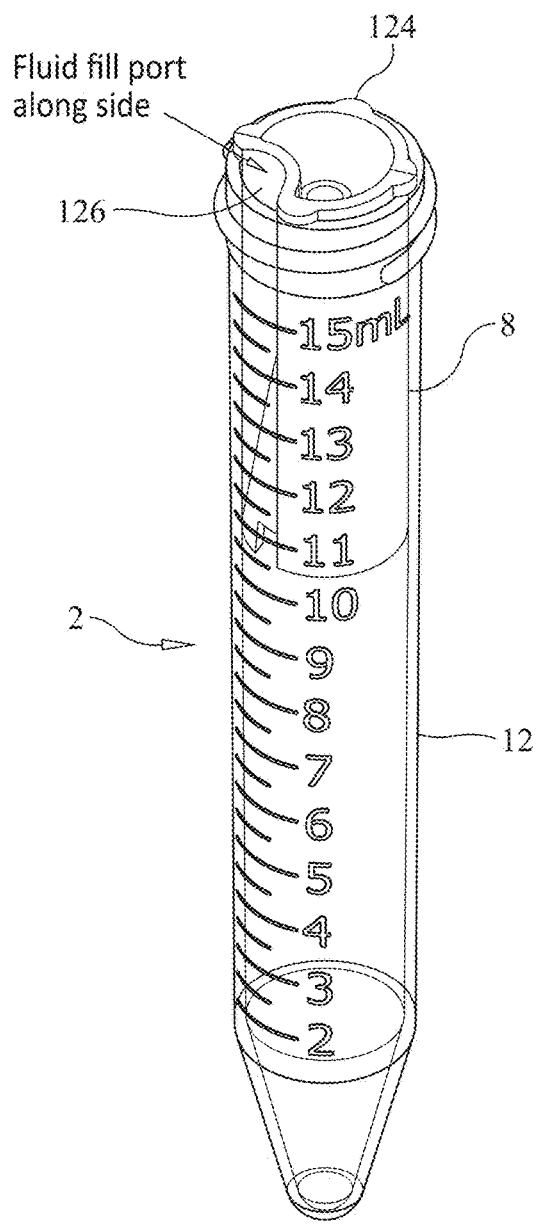
FIG. 37 is a perspective view of a third embodiment of a collection device constructed in accordance with the present invention and used in separating particles from a specimen.
Figure 38:
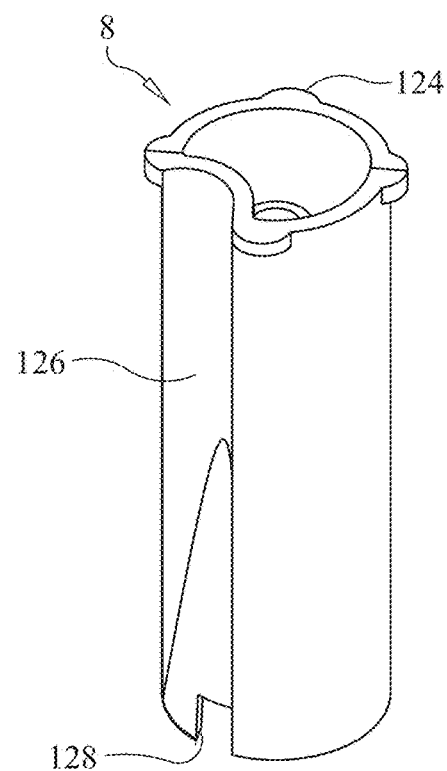
FIG. 38 is a perspective view of a particle accumulating plug formed in accordance with the present invention and used with the collection device of the present invention shown in FIG. 37.
Figure 39:
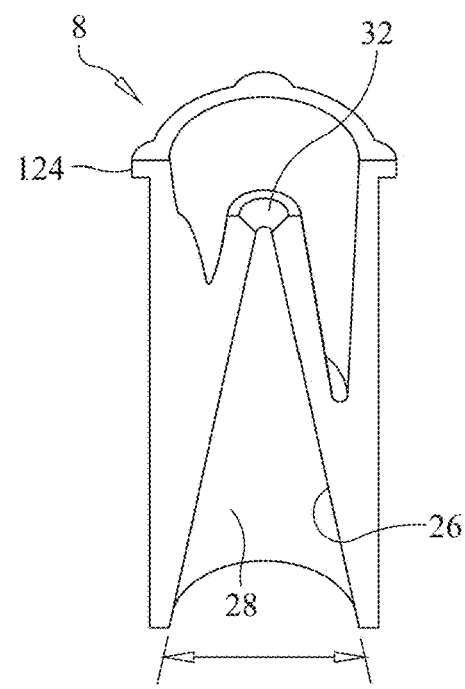
FIG. 39 is a partially cutaway, perspective view of the particle accumulating plug of the present invention shown in FIG. 38.
Figure 40:
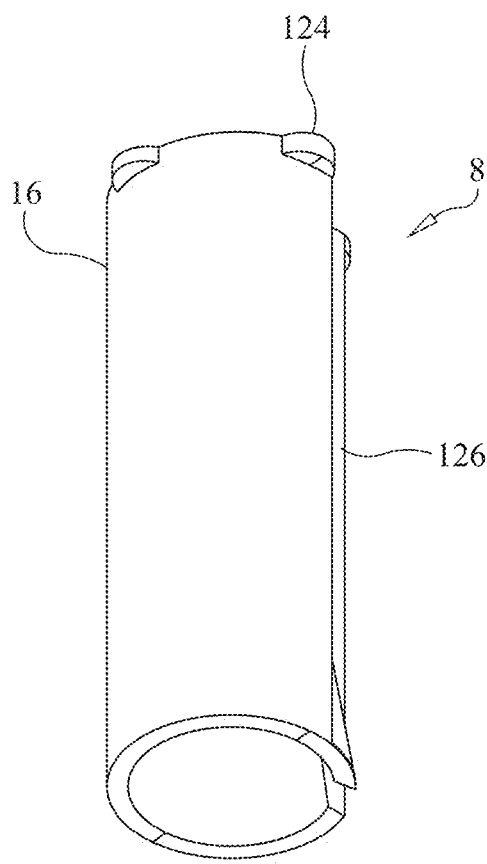
FIG. 40 is bottom perspective view of the particle accumulating plug of the present invention shown in FIG. 38.
Figure 41:
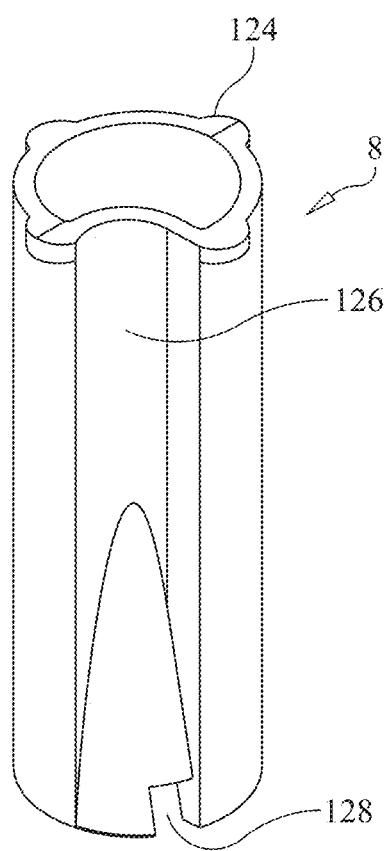
FIG. 41 is another perspective view of the particle accumulating plug of the present invention shown in FIGS. 38-40.
Figure 42:
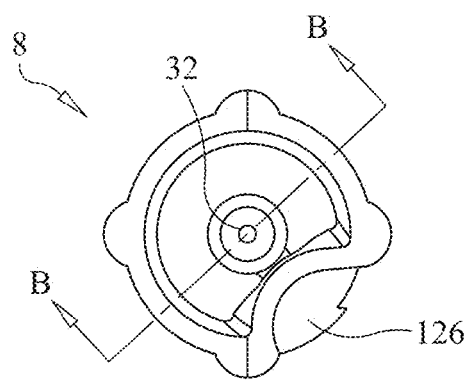
FIG. 42 is a top plan view of the particle accumulating plug of the present invention shown in FIGS. 38-41.
Figure 43:
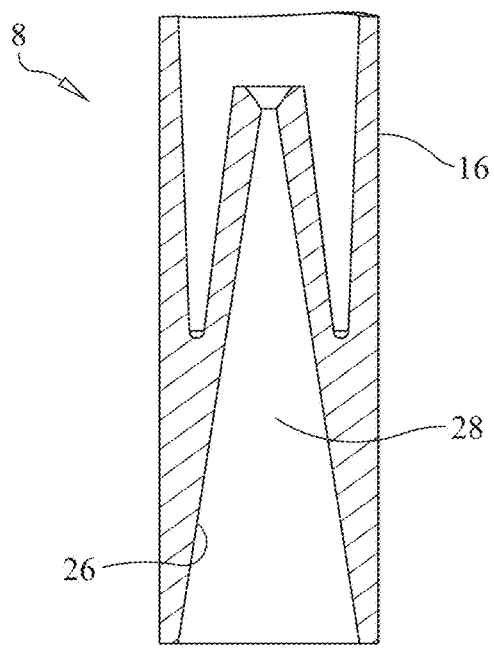
FIG. 43 is a cross-sectional view of the particle accumulating plug of the present invention shown in FIG. 42, taken along line B-B of FIG. 42.
Figure 44:
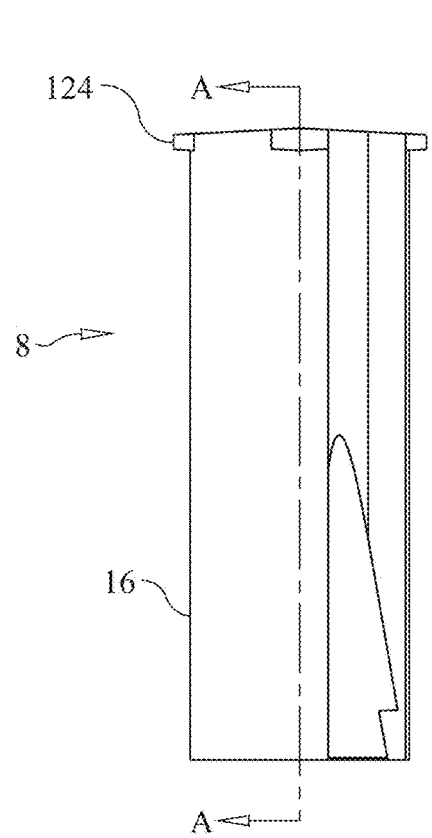
FIG. 44 is a side elevational view of the particle accumulating plug of the present invention shown in FIGS. 38-42.
Figure 45:
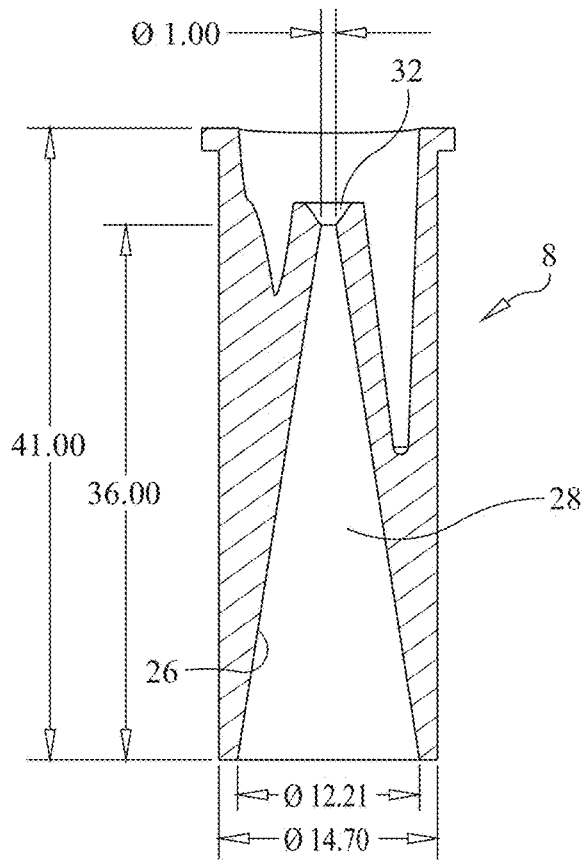
FIG. 45 is a cross-sectional view of the particle accumulating plug of the present invention shown in FIG. 44, taken along line A-A of FIG. 44.

Similarly, a preferred form of the second embodiment of the particle accumulating plug 8, and the removable flip cap 102 which the plug 8 forms part of, shown in FIGS. 8-29 of the drawings, are further illustrated with preferred dimensions in FIGS. 35 and 36. As shown in FIG. 36, the overall interior axial length of the conically-shaped inner wall 26 measured within the inverted funnel 28 from the bottom edge of the wall 26 to where the pipetting port 32 is formed in the inner wall 26 is preferably about 8.1 millimeters. The outer diameter of the plug 8 measured at the bottom edge of the conically-shaped inner wall 26 is preferably about 17.6 millimeters, and the inner diameter of the bore of the pipetting port 32 is preferably about 1 millimeter, although, again, the port diameter may vary according to the outer diameter of the pipette tip 34 received thereby and could be, for example, in a range of about 0.5 millimeters to about 2 millimeters. The angle of the conically-shaped inner wall 26 of the plug 8 of this second embodiment is preferably the same as described previously for the first embodiment of the plug 8 shown in FIGS. 2-7 and 32-34. The outer diameter of the lip or flange 124 is preferably about 20 millimeters which, again, depends on the inner and/or outer diameter of the second axial end 54 of the tube 50.

A third embodiment of a collection device 2 having a particle accumulating plug 8 formed in accordance with the present invention is shown in FIGS. 37-45 of the drawings. In this embodiment, the plug 8 is formed with an elongated tubular structure but includes the same or similar structural features of the plug 8 of the first embodiment shown in FIGS. 2-7 and 32-34 and the second embodiment shown in FIGS. 8-29, 35 and 36, including the conically-shaped inner wall 26 defining the funnel 28 in which the separated particles 6 accumulate. The collection device 2 and plug 8 of this third embodiment shown in FIGS. 37-45 also function in the same or similar manner in separating particles as described previously with respect to the collection devices 2 and plugs 8 of the first and second embodiments and, as such, the similar structural and functional features of the third embodiment of the collection device 2 and plug 8 that are in common with the collection devices 2 and plug 8 of the first and second embodiments will not be repeated here and are incorporated by reference herein.

Although the depictions of the plug 8 of this third embodiment shown in FIGS. 37-45 of the drawings are not drawn to scale, it should be noted that the plug 8 is elongated with a relatively steep angle provided to the conically-shaped inner wall 26 of about 9.6 degrees measured relative to the center longitudinal axis. More specifically, and in a preferred form, the conically-shaped inner wall 26 of the particle accumulating plug 8 of this third embodiment has an overall axial length measured within the inverted funnel 28 from the bottom edge of the inner wall 26 to where the pipetting port 32 is formed in the inner wall 26 is preferably about 36.00 millimeters. The outer diameter and inner diameter of the plug 8 measured at the bottom edge of the conically-shaped inner wall 26 are preferably 14.70 millimeters and 12.21 millimeters, respectively, and the inner diameter of the bore of the pipetting port 32 is preferably about 1.00 millimeter, although the port diameter may vary according to the outer diameter of the pipette tip 34 received thereby and could be, for example, in a range of about 0.5 millimeters to about 2 millimeters. The axial length of the plug measured from the bottom edge of the conically-shaped inner wall 26 to the bottom of the lip or flange 124, which rests on the edge of the open end 10 of the tube 12, 50 is preferably about 41.00 millimeters. In experiments performed using a collection device 2 and particle accumulating plug 8 of the present having the aforementioned dimensions, at least about 91 percent of parasite eggs have been recovered in the first pipette transfer event. This should be compared with the previously described conventional flotation method of separating parasite eggs at the surface or meniscus of the flotation solution, where tests reveal that only about two-thirds (i.e., 65.8 percent) of the eggs at the surface of the solution were able to be transferred to the microscope slide on the first coverslip contacting the meniscus.

In this third embodiment of the plug 8 of the collection device 2 shown in FIGS. 37-45, the fill port 94 for receiving flotation solution is formed as an elongated, generally U-shaped channel 126, concave in cross-section, extending axially along the longitudinal length of the plug 8 from the upper portion 92 of the plug 8 to the lower portion 90 thereof, the fill channel 126 being formed in the outer cylindrical sidewall 56 of the plug 8. Only one fill channel 126 is shown in the drawings, but it should be realized that two or more fill channels 126, spaced apart circumferentially from one another and formed in the outer cylindrical sidewall 56 of the plug 8, may be included. The fill channel 126 serves at least two preferred functions—the channel 126, which communicates with the interior bore 58 of the tube 12, 50, may be used to add flotation solution to the interior bore 58 of the tube 12, 50, just like with the fill port 94 of the second embodiment of the collection device 2 and plug 8 shown in FIGS. 8-29, 35 and 36, but also the fill channel 126 acts as an "overflow" reservoir to hold flotation solution therein, which can flow back into the interior bore 58 of the tube 12, 50 to replace flotation solution, carrying accumulated particles 6 (e.g., ova or eggs) withdrawn from the tube 12, 50 by the pipette 36 and aspirated into the pipette tip 34 received by the pipetting port 32 of the plug 8. The fill channel 126 may lead to a cutout or notch 128 formed in the conically-shaped inner wall 26 at the bottom edge thereof or in the outer sidewall 16 of the plug 8 at the lower portion thereof, which cutout or notch 128 is in fluid communication with each of the fill channel 126 and the interior bore 58 of the collection tube 12, 50 so that flotation solution may pass through the notch 128 between the fill channel 126 and the interior bore 58 of the tube 12, 50.

Furthermore, in this particular embodiment of the collection device 2 and plug 8 shown in FIGS. 37-45 of the drawings, the lip or flange 124 is preferably formed as discrete, radially extending segments (e.g., four, as shown in FIGS. 37, 38, 41 and 42) separated circumferentially from one another, each lip segment resting on the edge of the tube 12, 50 surrounding the tube's open end 10, rather than the lip or flange 124 forming a complete circle about the cylindrical outer sidewall 58 of the plug 8, such as shown in FIGS. 20-23, depicting a preferred form of the second embodiment of the collection device 2 and particle accumulating plug 8 of the present invention.

Although not shown in FIGS. 37-45, a cap having inner threads may be mounted on the open end portion 10 of the tube 12, 50 having mating threads formed on the exterior cylindrical sidewall 56 of the tube 12, 50 for closing the open end 10 of the tube 12, 50 of the collection device 2.

The collection device 2 and plug 8 of the present invention and the passive and centrifuge flotation methods of the present invention using the collection device 2 and plug 8 will now be further described.

A collection device 2 formed in accordance with one form of the present invention for separating particles 6 from a sample of matter 4 and concentrating the particles 6 therein for subsequent extraction and analysis preferably includes an elongated collection tube 12 for holding an emulsion 40 formed from mixing the sample of matter 4 with a flotation solution used in separating the particles 6 from the sample of matter 4, the particles 6 being suspended in the emulsion 40, the collection tube 12 having a sidewall, the sidewall including an inner surface 42, and defining a tube inner bore and a top opening 10 in communication with the tube inner bore; and a particle accumulating plug 8, the particle accumulating plug 8 being mounted in the tube inner bore of the collection tube 12 at the top opening 10 thereof, the particle accumulating plug 8 having an outer sidewall 16 defining a plug inner bore 18, and an inner wall 26 disposed within the plug inner bore 18, the inner wall 26 of the plug being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 12 are directed by the conically-shaped inner wall 26 to accumulate within the funnel 28 defined by the conically-shaped inner wall 26, providing a fluid thereat having a concentrated quantity of separated particles 6 for extraction therefrom by the fluid being aspirated into the tip 34 of the pipette 36 inserted into the pipetting port 32.

Preferably, at least a portion of the sidewall of the collection tube 12 is transparent so that the particle accumulating plug 8 within the tube inner bore is viewable through the transparent portion of the sidewall of the collection tube 12.

Moreover, at least a portion of the sidewall of the collection tube 12 is transparent so that the particle accumulating plug 8 within the tube inner bore is viewable through the transparent portion of the sidewall of the collection tube 12. Furthermore, at least a portion of the outer sidewall 16 of the particle accumulating plug 8 and at least a portion of the conically-shaped inner wall 26 of the particle accumulating plug 8 are transparent so that the level of the emulsion 40 within the tube inner bore of the collection tube 12 and within the funnel 28 defined by the conically-shaped inner wall 26 of the particle accumulating plug 8 is viewable through the transparent portion of the sidewall of the collection tube 12, the transparent portion of the outer sidewall 16 of the particle accumulating plug 8 and the transparent portion of the conically-shaped inner wall 26 of the particle accumulating plug 8.

The particle accumulating plug 8 preferably includes a screen 100, the screen 100 being disposed within the plug inner bore 18 below the conically-shaped inner wall 26 at a position opposite to the apex 30 of the funnel 28 defined by the inner wall 26 and where separated particles 6 enter the funnel 28.

Moreover, the screen 100 preferably has a multiplicity of pores formed through the thickness thereof, the screen 100 preferably being formed to define the pores with a general dimension of about 180 microns.

Preferably, the angle of the conically-shaped inner wall 26 of the particle accumulating plug 8 measured relative to a longitudinal central axis of the particle accumulating plug 8 is between about 5 degrees and about 60 degrees.

In another form of the collection device 2, the angle of the conically-shaped inner wall 26 of the particle accumulating plug 8 measured relative to a longitudinal central axis of the particle accumulating plug 8 is preferably between about 9 degrees and about 50 degrees.

In yet another form of the collection device 2, the angle of the conically-shaped inner wall 26 of the particle accumulating plug 8 measured relative to a longitudinal central axis of the particle accumulating plug 8 is preferably about 9.6 degrees.

The particle accumulating plug 8 preferably includes a fill port 94 formed through the thickness thereof and having a plug wall defining a fill bore 96, the fill bore 96 being in fluid communication with the fill port 94, the fill port 94 and fill bore 96 allowing a flotation solution to be added to the tube inner bore of the collection tube 12.

In yet another form, the outer sidewall 16 of the particle accumulating plug 8 preferably has a fill channel 126 formed therein, the fill channel 126 being in fluid communication with the top opening 10 and inner bore of the elongated collection tube 12, the fill channel 126 allowing a flotation solution to be added to the tube inner bore of the collection tube 12.

Furthermore, the outer sidewall 16 of the particle accumulating plug 8 preferably has formed through the thickness thereof a notch 128, the notch 128 being situated in alignment with and in fluid communication with the fill channel 126 to allow flotation solution within or added to the fill channel 126 to flow therethrough and into the tube inner bore of the collection tube 12.

In yet another form of the present invention, a collection device 2 for separating parasite ova, eggs or cells from a fecal specimen 4 and concentrating the parasite ova, eggs or cells therein for subsequent extraction and analysis preferably includes an elongated collection tube 12 for holding a fecal emulsion 40 formed from mixing the fecal specimen 4 with a flotation solution used in separating the parasite ova, eggs or cells from the fecal specimen 4, the parasite ova, eggs or cells being suspended in the emulsion 40, the collection tube 12 having a sidewall, the sidewall including an inner surface 42, and defining a tube inner bore and a top opening 10 in communication with the tube inner bore; and a particle accumulating plug 8, the particle accumulating plug 8 being mounted in the tube inner bore of the collection tube 12 at the top opening 10 thereof, the particle accumulating plug 8 having an outer sidewall 16 defining a plug inner bore 18, and an inner wall 26 disposed within the plug inner bore 18, the inner wall 26 of the plug being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The parasite ova, eggs or cells suspended in the fecal emulsion 40 that rise in the collection tube 12 are directed by the conically-shaped inner wall 26 to accumulate within the funnel 28 defined by the conically-shaped inner wall 26, providing a fluid thereat having a concentrated quantity of separated parasite ova, eggs or cells for extraction therefrom by the fluid being aspirated into the tip 34 of the pipette 36 inserted into the pipetting port 32.

Preferably, at least a portion of the sidewall of the collection tube 12 is transparent so that the particle accumulating plug 8 within the tube inner bore is viewable through the transparent portion of the sidewall of the collection tube 12.

Moreover, at least a portion of the sidewall of the collection tube 12 is preferably transparent so that the particle accumulating plug 8 within the tube inner bore is viewable through the transparent portion of the sidewall of the collection tube 12. Furthermore, at least a portion of the outer sidewall 16 of the particle accumulating plug 8 and at least a portion of the conically-shaped inner wall 26 of the particle accumulating plug 8 are preferably transparent so that the level of the fecal emulsion 40 within the tube inner bore of the collection tube 12 and within the funnel 28 defined by the conically-shaped inner wall 26 of the particle accumulating plug 8 is viewable through the transparent portion of the sidewall of the collection tube 12, the transparent portion of the outer sidewall 16 of the particle accumulating plug 8 and the transparent portion of the conically-shaped inner wall 26 of the particle accumulating plug 8.

The particle accumulating plug 8 may include a screen 100, the screen 100 being preferably disposed within the plug inner bore 18 below the conically-shaped inner wall 26 at a position opposite to the apex 30 of the funnel 28 defined by the inner wall 26 and where separated parasite ova, eggs or cells enter the funnel 28.

Furthermore, the screen 100 preferably has a multiplicity of pores formed through the thickness thereof, the screen 100 preferably being formed to define the pores with a general dimension of about 180 microns.

Preferably, the angle of the conically-shaped inner wall 26 of the particle accumulating plug 8 measured relative to a longitudinal central axis of the particle accumulating plug 8 is between about 5 degrees and about 60 degrees.

In another form of the collection device 2, the angle of the conically-shaped inner wall 26 of the particle accumulating plug 8 measured relative to a longitudinal central axis of the particle accumulating plug 8 is preferably between about 9 degrees and about 50 degrees.

In yet another form of the collection device 2, the angle of the conically-shaped inner wall 26 of the particle accumulating plug 8 measured relative to a longitudinal central axis of the particle accumulating plug 8 is preferably about 9.6 degrees.

The particle accumulating plug 8 may include a fill port 94 formed through the thickness thereof and having a plug wall defining a fill bore 96, the fill bore 96 being in fluid communication with the fill port 94, the fill port 94 and fill bore 96 allowing a flotation solution to be added to the tube inner bore of the collection tube 12.

In another form of the present invention, the outer sidewall 16 of the particle accumulating plug 8 preferably has a fill channel 126 formed therein, the fill channel 126 being in fluid communication with the top opening 10 and inner bore of the elongated collection tube 12, the fill channel 126 allowing a flotation solution to be added to the tube inner bore of the collection tube 12.

Furthermore, the outer sidewall 16 of the particle accumulating plug 8 preferably has formed through the thickness thereof a notch 128, the notch 128 being situated in alignment with and in fluid communication with the fill channel 126 to allow flotation solution within or added to the fill channel 126 to flow therethrough and into the tube inner bore of the collection tube 12.

In still another form of the present invention, a particle accumulating plug 8 for use in a collection device 2 for separating particles 6 from a sample of matter 4 and concentrating the particles 6 therein for subsequent extraction and analysis is disclosed, the collection device 2 including an elongated collection tube 12 for holding an emulsion 40 formed from mixing the sample of matter 4 with a flotation solution used in separating the particles 6 from the sample of matter 4, the particles 6 being suspended in the emulsion 40, the collection tube 12 having a sidewall, the sidewall including an inner surface 42, and defining a tube inner bore and a top opening 10 in communication with the tube inner bore, the particle accumulating plug 8 being mountable in the tube inner bore of the collection tube 12 at the top opening 10 thereof, the particle accumulating plug 8 preferably including an outer sidewall 16 defining a plug inner bore 18; and an inner wall 26 disposed within the plug inner bore 18, the inner wall 26 of the plug being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 12 are directed by the conically-shaped inner wall 26 to accumulate within the funnel 28 defined by the conically-shaped inner wall 26, providing a fluid thereat having a concentrated quantity of separated particles 6 for extraction therefrom by the fluid being aspirated into the tip 34 of the pipette 36 inserted into the pipetting port 32.

Preferably, the particle accumulating plug 8 includes a screen 100, the screen 100 being disposed within the plug inner bore 18 below the conically-shaped inner wall 26 at a position opposite to the apex 30 of the funnel 28 defined by the inner wall 26 and where separated particles 6 enter the funnel 28.

Moreover, the screen 100 preferably has a multiplicity of pores formed through the thickness thereof, the screen 100 preferably being formed to define the pores with a general dimension of about 180 microns.

The angle of the conically-shaped inner wall 26 of the particle accumulating plug 8 measured relative to a longitudinal central axis of the particle accumulating plug 8 is preferably between about 5 degrees and about 60 degrees.

In another form of the particle accumulating plug 8, the angle of the conically-shaped inner wall 26 of the particle accumulating plug 8 measured relative to a longitudinal central axis of the particle accumulating plug 8 is preferably between about 9 degrees and about 50 degrees.

In yet another form of the particle accumulating plug 8, the angle of the conically-shaped inner wall 26 of the particle accumulating plug 8 measured relative to a longitudinal central axis of the particle accumulating plug 8 is preferably about 9.6 degrees.

The particle accumulating plug 8 may include a fill port 94 formed through the thickness thereof and having a plug wall defining a fill bore 96, the fill bore 96 being in fluid communication with the fill port 94, the fill port 94 and fill bore 96 allowing a flotation solution to be added to the tube inner bore of the collection tube 12.

Furthermore, the outer sidewall 16 of the particle accumulating plug 8 may have a fill channel 126 formed therein, the fill channel 126 being in fluid communication with the top opening 10 and inner bore of the elongated collection tube 12, the fill channel 126 allowing a flotation solution to be added to the tube inner bore of the collection tube 12.

Moreover, the outer sidewall 16 of the particle accumulating plug 8 may have formed through the thickness thereof a notch 128, the notch 128 being situated in alignment with and in fluid communication with the fill channel 126 to allow flotation solution within or added to the fill channel 126 to flow therethrough and into the tube inner bore of the collection tube 12.

In still another form of the present invention, a particle accumulating plug 8 for use in a collection device 2 for separating particles 6 from a sample of matter 4 and concentrating the particles 6 therein for subsequent extraction and analysis is disclosed, the collection device 2 including an elongated collection tube 12 for holding an emulsion 40 formed from mixing the sample of matter 4 with a flotation solution used in separating the particles 6 from the sample of matter 4, the particles 6 being suspended in the emulsion 40, the collection tube 12 having a sidewall at least a portion of which is transparent, the sidewall including an inner surface 42, and defining a tube inner bore and a top opening 10 in communication with the tube inner bore, the particle accumulating plug 8 being mountable in the tube inner bore of the collection tube 12 at the top opening 10 thereof, the particle accumulating plug 8 being viewable through the transparent portion of the sidewall of the collection tube 12, the particle accumulating plug 8 preferably including an outer sidewall 16 defining a plug inner bore 18; and an inner wall 26 disposed within the plug inner bore 18, the inner wall 26 of the plug being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 12 are directed by the conically-shaped inner wall 26 to accumulate within the funnel 28 defined by the conically-shaped inner wall 26, providing a fluid thereat having a concentrated quantity of separated particles 6 for extraction therefrom by the fluid being aspirated into the tip 34 of the pipette 36 inserted into the pipetting port 32.

Preferably, at least a portion of the outer sidewall 16 of the particle accumulating plug 8 described above and at least a portion of the conically-shaped inner wall 26 of the particle accumulating plug 8 are transparent so that the level of the emulsion 40 within the tube inner bore of the collection tube 12 and within the funnel 28 defined by the conically-shaped inner wall 26 of the particle accumulating plug 8 is viewable through the transparent portion of the sidewall of the collection tube 12, the transparent portion of the outer sidewall 16 of the particle accumulating plug 8 and the transparent portion of the conically-shaped inner wall 26 of the particle accumulating plug 8 when the particle accumulating plug 8 is used with the collection device 2.

Moreover, the angle of the conically-shaped inner wall 26 of the particle accumulating plug 8 measured relative to a longitudinal central axis of the particle accumulating plug 8 is preferably between about 5 degrees and about 60 degrees.

In another form of the particle accumulating plug 8, the angle of the conically-shaped inner wall 26 of the particle accumulating plug 8 measured relative to a longitudinal central axis of the particle accumulating plug 8 is preferably between about 9 degrees and about 50 degrees.

In yet another form of the particle accumulating plug 8, the angle of the conically-shaped inner wall 26 of the particle accumulating plug 8 measured relative to a longitudinal central axis of the particle accumulating plug 8 is preferably about 9.6 degrees.

The particle accumulating plug 8 may include a fill port 94 formed through the thickness thereof and having a plug wall defining a fill bore 96, the fill bore 96 being in fluid communication with the fill port 94, the fill port 94 and fill bore 96 allowing a flotation solution to be added to the tube inner bore of the collection tube 12.

Preferably, the outer sidewall 16 of the particle accumulating plug 8 may have a fill channel 126 formed therein, the fill channel 126 being in fluid communication with the top opening 10 and inner bore of the elongated collection tube 12, the fill channel 126 allowing a flotation solution to be added to the tube inner bore of the collection tube 12.

Furthermore, the outer sidewall 16 of the particle accumulating plug 8 preferably has formed through the thickness thereof a notch 128, the notch 128 being situated in alignment with and in fluid communication with the fill channel 126 to allow flotation solution within or added to the fill channel 126 to flow therethrough and into the tube inner bore of the collection tube 12.

In one form of the present invention, a collection device 2 for separating particles 6 from a sample of matter 4 and concentrating the particles 6 therein for subsequent extraction and analysis includes an elongated collection tube 12 for holding an emulsion 40 formed from mixing the sample of matter 4 with a flotation solution 120 used in separating the particles 6 from the sample of matter 4, the particles 6 being suspended in the emulsion 40, the collection tube 12 having a sidewall 56, the sidewall 56 including an inner surface 42, and defining a tube inner bore 58 and a top opening 10 in communication with the tube inner bore 58; and a particle accumulating plug 8, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 12 are directed by the conically-shaped inner wall 26 to accumulate within the funnel 28 defined by the conically-shaped inner wall 26, providing a fluid thereat having a concentrated quantity of separated particles 6 for extraction therefrom by the fluid 48 being aspirated into the tip 34 of the pipette 36 inserted into the pipetting port 32.

Preferably, the outer sidewall 16 of the particle accumulating plug 8 includes a cylindrical upper portion 14 and a lower skirt portion 20 affixed to the cylindrical upper portion 14, the outer sidewall 16 at the lower skirt portion 20 of the plug 8 having a diameter which is greater than the diameter of the outer sidewall 16 at the cylindrical upper portion 14 of the plug 8, the outer sidewall 16 of the plug 8 at the lower skirt portion 20 thereof being radially resilient and slidably engaging the inner surface 42 of the sidewall 56 of the collection tube 12.

In another form of the collection device 2, the outer sidewall 16 of the particle accumulating plug 8 includes a cylindrical upper portion 14 and a lower skirt portion 20 affixed to the cylindrical upper portion 14, the outer sidewall 16 at the lower skirt portion 20 of the plug 8 having a diameter which is greater than the diameter of the outer sidewall 16 at the cylindrical upper portion 14 of the plug 8, the outer sidewall 16 of the particle accumulating plug 8 at the upper portion 14 thereof and the inner surface 42 of the sidewall 56 of the collection tube 12 defining a gap 44 therebetween, the outer sidewall 16 of the plug 8 at the lower skirt portion 20 thereof engaging the inner surface 42 of the sidewall 56 of the collection tube 12.

Furthermore, the outer sidewall 16 of the particle accumulating plug 8 at the lower skirt portion 20 thereof may include at least one cutout 24 formed through the thickness thereof, the at least one cutout 24 being provided to allow emulsion 40 present in the gap 44 between the cylindrical upper portion 14 of the plug outer sidewall 16 and the inner surface 42 of the sidewall 56 of the collection tube 12 to flow therethrough and into the tube inner bore 58 to replace fluid removed from the collection tube 12 by aspirating into the pipette tip 34 the fluid 48 containing the concentrated quantity of separated particles 6.

Preferably, at least a portion of the sidewall 56 of the collection tube 12 is transparent so that the relative position of the particle accumulating plug 8 within the tube inner bore 58 is viewable through the transparent portion of the sidewall 56 of the collection tube 12.

Moreover, at least a portion of the sidewall 56 of the collection tube 12 is preferably transparent so that the relative position of the particle accumulating plug 8 within the tube inner bore 58 is viewable through the transparent portion of the sidewall 56 of the collection tube 12. Furthermore, at least a portion of the outer sidewall 16 of the particle accumulating plug 8 and at least a portion of the conically-shaped inner wall 26 of the particle accumulating plug 8 are preferably transparent so that the level of the emulsion 40 within the tube inner bore 58 of the collection tube 12 and within the funnel 28 defined by the conically-shaped inner wall 26 of the particle accumulating plug 8 is viewable through the transparent portion of the sidewall 56 of the collection tube 12, the transparent portion of the outer sidewall 16 of the particle accumulating plug 8 and the transparent portion of the conically-shaped inner wall 26 of the particle accumulating plug 8.

The particle accumulating plug 8 may further include a screen 100 disposed within the plug inner bore 18 below the conically-shaped inner wall 26 at a position opposite to the apex 30 of the funnel 28 defined by the inner wall 26 and where separated particles 6 enter the funnel 28.

Furthermore, the screen 100 preferably has a multiplicity of pores formed through the thickness thereof, the screen 100 being preferably formed to define the pores with a general dimension of about 180 microns.

In accordance with another embodiment of the present invention, a collection device 2 for separating parasite ova, eggs or cells from a fecal specimen 4 and concentrating the parasite ova, eggs or cells therein for subsequent extraction and analysis includes an elongated collection tube 12 for holding a fecal emulsion 40 formed from mixing the fecal specimen 4 with a flotation solution 120 used in separating the parasite ova, eggs or cells from the fecal specimen 4, the parasite ova, eggs or cells being suspended in the emulsion 40, the collection tube 12 having a sidewall 56, the sidewall 56 including an inner surface 42, and defining a tube inner bore 58 and a top opening 10 in communication with the tube inner bore 58; and a particle accumulating plug 8, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The parasite ova, eggs or cells suspended in the fecal emulsion 40 that rise in the collection tube 12 are directed by the conically-shaped inner wall 26 to accumulate within the funnel 28 defined by the conically-shaped inner wall 26, providing a fluid thereat having a concentrated quantity of separated parasite ova, eggs or cells for extraction therefrom by the fluid 48 being aspirated into the tip 34 of the pipette 36 inserted into the pipetting port 32.

Preferably, the outer sidewall 16 of the particle accumulating plug 8 includes a cylindrical upper portion 14 and a lower skirt portion 20 affixed to the cylindrical upper portion 14, the outer sidewall 16 at the lower skirt portion 20 of the plug 8 having a diameter which is greater than the diameter of the outer sidewall 16 at the cylindrical upper portion 14 of the plug 8, the outer sidewall 16 of the plug 8 at the lower skirt portion 20 thereof being radially resilient and slidably engaging the inner surface 42 of the sidewall 56 of the collection tube 12.

Furthermore, the outer sidewall 16 of the particle accumulating plug 8 preferably includes a cylindrical upper portion 14 and a lower skirt portion 20 affixed to the cylindrical upper portion 14, the outer sidewall 16 at the lower skirt portion 20 of the plug 8 having a diameter which is greater than the diameter of the outer sidewall 16 at the cylindrical upper portion 14 of the plug 8, the outer sidewall 16 of the particle accumulating plug 8 at the upper portion 14 thereof and the inner surface 42 of the sidewall 56 of the collection tube 12 defining a gap 44 therebetween, the outer sidewall 16 of the plug 8 at the lower skirt portion 20 thereof engaging the inner surface 42 of the sidewall 56 of the collection tube 12.

Moreover, the outer sidewall 16 of the particle accumulating plug 8 at the lower skirt portion 20 thereof preferably includes at least one cutout 24 formed through the thickness thereof, the at least one cutout 24 being provided to allow fecal emulsion 40 present in the gap 44 between the cylindrical upper portion 14 of the plug 8 outer sidewall 16 and the inner surface 42 of the sidewall 56 of the collection tube 12 to flow therethrough and into the tube inner bore 58 to replace fluid removed from the collection tube 12 by aspirating into the pipette tip 34 the fluid 48 containing the concentrated quantity of separated parasite ova, eggs or cells.

At least a portion of the sidewall 56 of the collection tube 12 is preferably transparent so that the relative position of the particle accumulating plug 8 within the tube inner bore 58 is viewable through the transparent portion of the sidewall 56 of the collection tube 12.

Even more preferably, at least a portion of the sidewall 56 of the collection tube 12 is transparent so that the relative position of the particle accumulating plug 8 within the tube inner bore 58 is viewable through the transparent portion of the sidewall 56 of the collection tube 12. Also, at least a portion of the outer sidewall 16 of the particle accumulating plug 8 and at least a portion of the conically-shaped inner wall 26 of the particle accumulating plug 8 are transparent so that the level of the fecal emulsion 40 within the tube inner bore 58 of the collection tube 12 and within the funnel 28 defined by the conically-shaped inner wall 26 of the particle accumulating plug 8 is viewable through the transparent portion of the sidewall 56 of the collection tube 12, the transparent portion of the outer sidewall 16 of the particle accumulating plug 8 and the transparent portion of the conically-shaped inner wall 26 of the particle accumulating plug 8.

The particle accumulating plug 8 of the above-described embodiment may also include a screen 100 disposed within the plug inner bore 18 below the conically-shaped inner wall 26 at a position opposite to the apex 30 of the funnel 28 defined by the inner wall 26 and where separated parasite ova, eggs or cells enter the funnel 28. Preferably, the screen 100 has a multiplicity of pores formed through the thickness thereof, the screen 100 being preferably formed to define the pores with a general dimension of about 180 microns.

In yet another embodiment of the present invention, a particle accumulating plug 8 for use in a collection device 2 for separating particles 6 from a sample of matter 4 and concentrating the particles 6 therein for subsequent extraction and analysis, the collection device 2 including an elongated collection tube 12 for holding an emulsion 40 formed from mixing the sample of matter 4 with a flotation solution 120 used in separating the particles 6 from the sample of matter 4, the particles 6 being suspended in the emulsion 40, the collection tube 12 having a sidewall 56, the sidewall 56 including an inner surface 42, and defining a tube inner bore 58 and a top opening 10 in communication with the tube inner bore 58, the particle accumulating plug 8 being mountable in the tube inner bore 58 of the collection tube 12 through the top opening 10 thereof and axially movable within the bore 58 to occupy a desired position therein, the particle accumulating plug 8 including an outer sidewall 16 defining a plug inner bore 18 and an inner wall 26 disposed within the plug inner bore 18, the inner wall 26 of the plug 8 being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 12 are directed by the conically-shaped inner wall 26 to accumulate within the funnel 28 defined by the conically-shaped inner wall 26, providing a fluid thereat having a concentrated quantity of separated particles 6 for extraction therefrom by the fluid 48 being aspirated into the tip 34 of the pipette 36 inserted into the pipetting port 32.

Preferably, the outer sidewall 16 of the particle accumulating plug 8 includes a cylindrical upper portion 14 and a lower skirt portion 20 affixed to the cylindrical upper portion 14, the outer sidewall 16 at the lower skirt portion 20 of the plug 8 having a diameter which is greater than the diameter of the outer sidewall 16 at the cylindrical upper portion 14 of the plug 8, the outer sidewall 16 of the plug 8 at the lower skirt portion 20 thereof being radially resilient and slidably engaging the inner surface 42 of the sidewall 56 of the collection tube 12 when the particle accumulating plug 8 is received by the collection tube 12 of the collection device 2.

Moreover, the outer sidewall 16 of the particle accumulating plug 8 preferably includes a cylindrical upper portion 14 and a lower skirt portion 20 affixed to the cylindrical upper portion 14, the outer sidewall 16 at the lower skirt portion 20 of the plug 8 having a diameter which is greater than the diameter of the outer sidewall 16 at the cylindrical upper portion 14 of the plug 8, the outer sidewall 16 of the particle accumulating plug 8 at the upper portion 14 thereof and the inner surface 42 of the sidewall 56 of the collection tube 12 defining a gap 44 therebetween, the outer sidewall 16 of the plug 8 at the lower skirt portion 20 thereof engaging the inner surface 42 of the sidewall 56 of the collection tube 12 when the particle accumulating plug 8 is received by the collection tube 12 of the collection device 2.

Furthermore, the outer sidewall 16 of the particle accumulating plug 8 at the lower skirt portion 20 thereof preferably includes at least one cutout 24 formed through the thickness thereof, the at least one cutout 24 being provided to allow emulsion 40 present in the gap 44 between the cylindrical upper portion 14 of the plug 8 outer sidewall 16 and the inner surface 42 of the sidewall 56 of the collection tube 12 to flow therethrough and into the tube inner bore 58 to replace fluid removed from the collection tube 12 by aspirating into the pipette tip 34 the fluid 48 containing the concentrated quantity of separated particles 6 when the particle accumulating plug 8 is used with the collection device 2.

The particle accumulating plug 8 may further include a screen 100, the screen 100 being disposed within the plug inner bore 18 below the conically-shaped inner wall 26 at a position opposite to the apex 30 of the funnel 28 defined by the inner wall 26 and where separated particles 6 enter the funnel 28. Preferably, the screen 100 has a multiplicity of pores formed through the thickness thereof, the screen 100 preferably being formed to define the pores with a general dimension of about 180 microns.

In another form of the particle accumulating plug 8 for use in a collection device 2 for separating particles 6 from a sample of matter 4 and concentrating the particles 6 therein for subsequent extraction and analysis, the collection device 2 including an elongated collection tube 12 for holding an emulsion 40 formed from mixing the sample of matter 4 with a flotation solution 120 used in separating the particles 6 from the sample of matter 4, the particles 6 being suspended in the emulsion 40, the collection tube 12 having a sidewall 56 at least a portion of which is transparent, the sidewall 56 including an inner surface 42, and defining a tube inner bore 58 and a top opening 10 in communication with the tube inner bore 58, the particle accumulating plug 8 being mountable in the tube inner bore 58 of the collection tube 12 through the top opening 10 thereof and axially movable within the bore 58 to occupy a desired position therein, the particle accumulating plug 8 being viewable through the transparent sidewall 56 of the collection tube 12 so that the relative position of the particle accumulating plug 8 within tube inner bore 58 is viewable through the transparent portion of the sidewall 56 of the collection tube 12 when the particle accumulating plug 8 is received by the collection tube 12 of the collection device 2, the particle accumulating plug 8 including an outer sidewall 16 defining a plug inner bore 18 and an inner wall 26 disposed within the plug inner bore 18, the inner wall 26 of the plug 8 being conically shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 12 are directed by the conically-shaped inner wall 26 to accumulate within the funnel 28 defined by the conically-shaped inner wall 26, providing a fluid thereat having a concentrated quantity of separated particles 6 for extraction therefrom by the fluid 48 being aspirated into the tip 34 of the pipette 36 inserted into the pipetting port 32.

Preferably, at least a portion of the outer sidewall 16 of the particle accumulating plug 8 in the above-described embodiment and at least a portion of the conically-shaped inner wall 26 of the particle accumulating plug 8 are transparent so that the level of the emulsion 40 within the tube inner bore 58 of the collection tube 12 and within the funnel 28 defined by the conically-shaped inner wall 26 of the particle accumulating plug 8 is viewable through the transparent portion of the sidewall 56 of the collection tube 12, the transparent portion of the outer sidewall 16 of the particle accumulating plug 8 and the transparent portion of the conically-shaped inner wall 26 of the particle accumulating plug 8 when the particle accumulating plug 8 is used with the collection device 2.

In yet another embodiment of the present invention, a disposable, self-contained collection device 2 for separating particles 6 from a sample of matter 4 and concentrating the particles 6 therein for subsequent extraction and analysis includes an elongated collection tube 50 for holding the sample of matter 4 and a flotation solution 120 used in separating the particles 6 from the sample of matter 4, and mixing the sample of matter 4 with the flotation solution 120 to form an emulsion 40 in which the particles 6 are suspended, the collection tube 50 having a sidewall 56, the sidewall 56 including an inner surface, and defining a tube inner bore 58 and an open first axial end 52 and an opposite open second axial end 54, each of the open first and second axial ends 52, 54 being in communication with the tube inner bore 58; a collection scoop assembly 60 removably mounted on the first axial end 52 of the collection tube 50, the collection scoop assembly 60 having a handle 72 and a scoop 70 mounted on the handle 72, the collection scoop assembly 60 being removable from the first axial end 52 of the collection tube 50 for obtaining the sample of matter 4 and being replaceable on the first axial end 52 of the collection tube 50 such that the sample of matter 4 obtained by the collection assembly will reside within the tube inner bore 58 of the collection tube 50; and a particle accumulating plug 8, the particle accumulating plug 8 being mounted on the opposite second axial end 54 of the collection tube 50, the particle accumulating plug 8 having an outer sidewall 86 situated in close proximity to the inner surface of the sidewall 86 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The particles 6 suspended in the emulsion 40 that rise in the collection tube 50 are directed by the conically-shaped inner wall 26 to accumulate within the funnel 28 defined by the conically-shaped inner wall 26, providing a fluid thereat having a concentrated quantity of separated particles 6 for extraction therefrom by the fluid 48 being aspirated into the tip 34 of the pipette 36 inserted into the pipetting port 32.

The disposable, self-contained collection device 2 described above may further include a flip cap 102, the flip cap 102 being attached to the particle accumulating plug 8 to selectively cover and uncover the plug 8 and to ensure that a fluidtight seal on the second axial end 54 of the tube 50 is provided when the cap 102 is positioned to cover the plug 8.

The particle accumulating plug 8 further preferably includes a fill port 94 formed through the thickness thereof and a longitudinally extending interior plug wall 98 defining a fill bore 96, the fill bore 96 being in communication with the fill port 94, the fill port 94 and fill bore 96 allowing a flotation solution 120 to be added to the tube inner bore 58 of the collection tube 50.

Furthermore, the longitudinally extending interior plug wall 98 which defines the fill bore 96 preferably extends from the fill port 94 axially downwardly therefrom within the plug inner bore 88 to a depth therein near or below the conically-shaped inner wall 26 where separated particles 6 enter the funnel 28 defined by the conically-shaped inner wall 26 such that the addition of the flotation solution 120 through the fill port 94 and fill bore 96 of the particle accumulating plug 8 to the tube inner bore 58 of the collection tube 50 will substantially not disturb separated particles 6 accumulating in the funnel 28 defined by the conically-shaped inner wall 26 of the particle accumulating plug 8.

Moreover, the disposable, self-contained collection device 2 may further include a cap 102, the cap 102 being removably mounted on one of the particle accumulating plug 8 and the collection tube 50 at the second axial end 54 thereof defined by the tube sidewall 56 to selectively cover and uncover the one of the particle accumulating plug 8 and the collection tube 50.

Preferably, the cap 102 includes a main body 106, the main body 106 having structure which engages the pipetting port 32 of the particle accumulating plug 8 and forms a fluidtight seal therewith when the cap 102 is mounted on and covering the one of the particle accumulating plug 8 and the collection tube 50.

In yet another form, the disposable, self-contained collection device 2 further includes a cap 102, the cap 102 being removably mounted on one of the particle accumulating plug 8 and the collection tube 50 at the second axial end 54 thereof defined by the tube sidewall 56 to selectively cover and uncover the one of the particle accumulating plug 8 and the collection tube 50. The cap 102 includes a main body 106, the main body 106 having a first structure and a second structure which respectively engage the pipetting port 32 and the fill port 94 of the particle accumulating plug 8 and which form a fluidtight seal respectively therewith when the cap 102 is mounted on and covering the one of the particle accumulating plug 8 and the collection tube 50.

The disposable, self-contained collection device 2 further preferably includes a living hinge 104, the living hinge 104 having a first hinge end to which the flip cap 102 is attached and a second hinge end to which one of the particle accumulating plug 8 and the collection tube 50 is attached.

The particle accumulating plug 8 of this embodiment may further include a screen 100, the screen 100 being disposed within the plug inner bore 88 below the conically-shaped inner wall 26 at a position opposite to the apex 30 of the funnel 28 defined by the inner wall 26 and where separated particles 6 enter the funnel 28. Furthermore, the screen 100 has a multiplicity of pores formed through the thickness thereof, the screen 100 being preferably formed to define the pores with a general dimension of about 180 microns.

In another form of the disposable, self-contained collection device 2, the scoop 70 of the collection scoop assembly 60 includes a concave spoon portion 76 and a plurality of peripheral, spaced apart edge teeth 74 at least partially surrounding the concave spoon portion 76, the plurality of edge teeth 74 being provided to help retain the sample of matter 4 to the scoop 70 of the collection scoop assembly 60.

Preferably, the scoop 70 of the collection scoop assembly 60 includes a concave spoon portion 76, the concave spoon portion 76 having at least one cutout 78 formed through the thickness thereof, the at least one cutout 78 being provided to help retain the sample of matter 4 to the scoop 70 of the collection scoop assembly 60.

Furthermore, the handle 72 of the collection scoop assembly 60 may include a sidewall 84 having an outer surface, and a groove 82 formed in the outer surface of the handle sidewall 84. The handle 72 may further include an O-ring 80 seated in the groove 82, the O-ring 80 forming a fluidtight seal with the collection tube 50 when the collection scoop assembly 60 is mounted on the first axial end 52 defined by the sidewall 56 of the collection tube 50.

In accordance with the present invention, the longitudinally extending interior plug wall 98 is preferably generally conically-shaped to define the fill bore 96 with a funnel shape.

Also, preferably, at least a portion of the sidewall 56 of the collection tube 50 is transparent so that the level of the emulsion 40 within the tube inner bore 58 of the collection tube 50 is viewable through the transparent portion of the sidewall 56 of the collection tube 50.

More specifically, at least a portion of the outer sidewall 86 of the particle accumulating plug 8 and at least a portion of the conically-shaped inner wall 26 of the particle accumulating plug 8 are preferably transparent so that the level of the emulsion 40 within the tube inner bore 58 of the collection tube 50 and within the funnel 28 defined by the conically-shaped inner wall 26 of the particle accumulating plug 8 is viewable through the transparent portion of the sidewall 56 of the collection tube 50, the transparent portion of the outer sidewall 86 of the particle accumulating plug 8 and the transparent portion of the conically-shaped inner wall 26 of the particle accumulating plug 8.

In yet another form of the present invention, a disposable, self-contained collection device 2 for separating parasite ova, eggs or cells from a fecal specimen 4 and concentrating the parasite ova, eggs or cells therein for subsequent extraction and analysis includes an elongated collection tube 50 for holding the fecal specimen 4 and a flotation solution 120 used in separating the parasite ova, eggs or cells from the fecal specimen 4, and mixing the fecal specimen 4 with the flotation solution 120 to form a fecal emulsion 40 in which the parasite ova, eggs or cells are suspended, the collection tube 50 having a sidewall 56, the sidewall 56 including an inner surface, and defining a tube inner bore 58 and an open first axial end 52 and an opposite open second axial end 54, each of the open first and second axial ends 52, 54 being in communication with the tube inner bore 58; a collection scoop assembly 60 removably mounted on the first axial end 52 of the collection tube 50, the collection scoop assembly 60 having a handle 72 and a scoop 70 mounted on the handle 72, the collection scoop assembly 60 being removable from the first axial end 52 of the collection tube 50 for obtaining the fecal specimen 4 and being replaceable on the first axial end 52 of the collection tube 50 such that the fecal specimen 4 obtained by the collection assembly will reside within the tube inner bore 58 of the collection tube 50; and a particle accumulating plug 8, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36. The parasite ova, eggs or cells suspended in the fecal emulsion 40 that rise in the collection tube 50 are directed by the conically-shaped inner wall 26 to accumulate within the funnel 28 defined by the conically-shaped inner wall 26, providing a fluid thereat having a concentrated quantity of separated parasite ova, eggs or cells for extraction therefrom by the fluid 48 being aspirated into the tip 34 of the pipette 36 inserted into the pipetting port 32.

The disposable, self-contained collection device 2 described above may further include a flip cap 102, the flip cap 102 being attached to the particle accumulating plug 8 to selectively cover and uncover the plug 8 and to ensure that a fluidtight seal on the second axial end 54 of the tube 50 is provided when the cap 102 is positioned to cover the plug 8.

Preferably, the particle accumulating plug 8 of the above-described embodiment further includes a fill port 94 formed through the thickness thereof and a longitudinally extending interior plug wall 98 defining a fill bore 96, the fill bore 96 being in communication with the fill port 94, the fill port 94 and fill bore 96 allowing a flotation solution 120 to be added to the tube inner bore 58 of the collection tube 50.

More specifically, the longitudinally extending interior plug wall 98 which defines the fill bore 96 extends from the fill port 94 axially downwardly therefrom within the plug inner bore 88 to a depth therein near or below the conically-shaped inner wall 26 where separated parasite ova, eggs or cells enter the funnel 28 defined by the conically-shaped inner wall 26 such that the addition of the flotation solution 120 through the fill port 94 and fill bore 96 of the particle accumulating plug 8 to the tube inner bore 58 of the collection tube 50 will substantially not disturb separated parasite ova, eggs or cells accumulating in the funnel 28 defined by the conically-shaped inner wall 26 of the particle accumulating plug 8.

The disposable, self-contained collection device 2 described above preferably further includes a cap 102, the cap 102 being removably mounted on one of the particle accumulating plug 8 and the collection tube 50 at the second axial end 54 thereof defined by the tube sidewall 56 to selectively cover and uncover the one of the particle accumulating plug 8 and the collection tube 50.

Preferably, the cap 102 includes a main body 106, the main body 106 having structure which engages the pipetting port 32 of the particle accumulating plug 8 and forms a fluidtight seal therewith when the cap 102 is mounted on and covering the one of the particle accumulating plug 8 and the collection tube 50.

Even more specifically, the disposable, self-contained collection device 2 preferably further includes a cap 102, the cap 102 being removably mounted on one of the particle accumulating plug 8 and the collection tube 50 at the second axial end 54 thereof defined by the tube sidewall 56 to selectively cover and uncover the one of the particle accumulating plug 8 and the collection tube 50. The cap 102 includes a main body 106, the main body 106 having a first structure and a second structure which respectively engage the pipetting port 32 and the fill port 94 of the particle accumulating plug 8 and which form a fluidtight seal respectively therewith when the flip cap 102 is mounted on and covering the one of the particle accumulating plug 8 and the collection tube 50.

The disposable, self-contained collection device 2 described above preferably further includes a living hinge 104, the living hinge 104 having a first hinge end to which the flip cap 102 is attached and a second hinge end to which one of the particle accumulating plug 8 and the collection tube 50 is attached.

The particle accumulating plug 8 of the above-described collection device 2 may include a screen 100, the screen 100 being disposed within the plug inner bore 88 below the conically-shaped inner wall 26 at a position opposite to the apex 30 of the funnel 28 defined by the inner wall 26 and where separated parasite ova, eggs or cells enter the funnel 28. Preferably, the screen 100 has a multiplicity of pores formed through the thickness thereof, the screen 100 preferably being formed to define the pores with a general dimension of about 180 microns.

The scoop 70 of the collection scoop assembly 60 for separating ova, eggs and other particles from a fecal specimen 4 preferably includes a concave spoon portion 76 and a plurality of peripheral, spaced apart edge teeth 74 at least partially surrounding the concave spoon portion 76, the plurality of edge teeth 74 being provided to help retain the fecal specimen 4 to the scoop 70 of the collection scoop assembly 60.

Preferably, and in yet another version, the scoop 70 of the collection scoop assembly 60 includes a concave spoon portion 76, the concave spoon portion 76 having at least one cutout 78 formed through the thickness thereof, the at least one cutout 78 being provided to help retain the fecal specimen 4 to the scoop 70 of the collection scoop assembly 60.

Moreover, the handle 72 of the collection scoop assembly 60 preferably includes a sidewall 84 having an outer surface, and a groove 82 formed in the outer surface of the handle sidewall 84. The handle 72 may further include an O-ring 80 seated in the groove 82, the O-ring 80 forming a fluidtight seal with the collection tube 50 when the collection scoop assembly 60 is mounted on the first axial end 52 defined by the sidewall 56 of the collection tube 50.

Also, in the above-described embodiment of the collection device 2, the longitudinally extending interior plug wall 98 preferably is generally conically-shaped to define the fill bore 96 with a funnel shape.

Furthermore, at least a portion of the sidewall 56 of the collection tube 50 is preferably transparent so that the level of the fecal emulsion 40 within the tube inner bore 58 of the collection tube 50 is viewable through the transparent portion of the sidewall 56 of the collection tube 50.

Preferably, and even more specifically, at least a portion of the outer sidewall 86 of the particle accumulating plug 8 and at least a portion of the conically-shaped inner wall 26 of the particle accumulating plug 8 are transparent so that the level of the fecal emulsion 40 within the tube inner bore 58 of the collection tube 50 and within the funnel 28 defined by the conically-shaped inner wall 26 of the particle accumulating plug 8 is viewable through the transparent portion of the sidewall 56 of the collection tube 50, the transparent portion of the outer sidewall 86 of the particle accumulating plug 8 and the transparent portion of the conically-shaped inner wall 26 of the particle accumulating plug 8.

A passive flotation method for separating particles 6 from a sample of matter 4 in accordance with the present invention preferably includes the steps of mixing the sample of matter 4 with a flotation solution 120 having a predetermined specific gravity in a collection device 2 to form an emulsion 40 therein, the particles 6 being suspended in the emulsion 40, the collection device 2 including an elongated collection tube 12 for holding the emulsion 40 formed from mixing the sample of matter 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the emulsion 40 therein is substantially level with the pipetting port 32 of the particle accumulating plug 8; allowing the emulsion 40 within the collection tube 12 of the collection device 2 to rest for a predetermined period of time so that particles 6 in the emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated particles 6; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Another form of the passive flotation method of the present invention for separating particles 6 from a sample of matter 4 preferably includes the steps of mixing the sample of matter 4 with a flotation solution 120 having a predetermined specific gravity in a mixing cup to form an emulsion 40 therein, the particles 6 being suspended in the emulsion 40; pouring a volume of the emulsion 40 from the mixing cup into a collection device 2, the collection device 2 including an elongated collection tube 12 for holding the emulsion 40 formed from mixing the sample of matter 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the emulsion 40 therein is substantially level with the pipetting port 32 of the particle accumulating plug 8; allowing the emulsion 40 within the collection tube 12 of the collection device 2 to rest for a predetermined period of time so that particles 6 in the emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated particles 6; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Yet another passive flotation method in accordance with the present invention for separating parasite ova, eggs or cells from a fecal specimen 4 preferably includes the steps of mixing the fecal specimen 4 with a flotation solution 120 having a predetermined specific gravity in a collection device 2 to form a fecal emulsion 40 therein, the parasite ova, eggs or cells being suspended in the fecal emulsion 40, the collection device 2 including an elongated collection tube 12 for holding the fecal emulsion 40 formed from mixing the fecal specimen 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the fecal emulsion 40 therein is substantially level with the pipetting port 32 of the particle accumulating plug 8; allowing the fecal emulsion 40 within the collection tube 12 of the collection device 2 to rest for a predetermined period of time so that parasite ova, eggs or cells in the fecal emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated parasite ova, eggs or cells; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

Another form of the passive flotation method in accordance with the present invention for separating parasite ova, eggs or cells from a fecal specimen 4 preferably includes the steps of mixing the fecal specimen 4 with a flotation solution 120 having a predetermined specific gravity in a mixing cup to form a fecal emulsion 40 therein, the parasite ova, eggs or cells being suspended in the fecal emulsion 40; pouring a volume of the fecal emulsion 40 from the mixing cup into a collection device 2, the collection device 2 including an elongated collection tube 12 for holding the fecal emulsion 40 formed from mixing the fecal specimen 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the fecal emulsion 40 therein is substantially level with the pipetting port 32 of the particle accumulating plug 8; allowing the fecal emulsion 40 within the collection tube 12 of the collection device 2 to rest for a predetermined period of time so that parasite ova, eggs or cells in the fecal emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated parasite ova, eggs or cells; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

A centrifuge flotation method in accordance with the present invention for separating particles 6 from a sample of matter 4 preferably includes the steps of mixing the sample of matter 4 with a flotation solution 120 having a predetermined specific gravity in a collection device 2 to form an emulsion 40 therein, the particles 6 being suspended in the emulsion 40, the collection device 2 including an elongated collection tube 12 for holding the emulsion 40 formed from mixing the sample of matter 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the emulsion 40 therein is substantially level with the pipetting port 32 of the particle accumulating plug 8; centrifuging the emulsion 40 within the collection tube 12 of the collection device 2 for a predetermined period of time so that during or after centrifugation particles 6 in the emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated particles 6; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Another form of the centrifuge flotation method of the present invention for separating particles 6 from a sample of matter 4 preferably includes the steps of mixing the sample of matter 4 with a flotation solution 120 having a predetermined specific gravity in a mixing cup to form an emulsion 40 therein, the particles 6 being suspended in the emulsion 40; pouring a volume of the emulsion 40 from the mixing cup into a collection device 2, the collection device 2 including an elongated collection tube 12 for holding the emulsion 40 formed from mixing the sample of matter 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the emulsion 40 therein is substantially level with the pipetting port 32 of the particle accumulating plug 8; centrifuging the emulsion 40 within the collection tube 12 of the collection device 2 for a predetermined period of time so that during or after centrifugation particles 6 in the emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated particles 6; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Yet another centrifuge flotation method in accordance with the present invention for separating parasite ova, eggs or cells from a fecal specimen 4 preferably includes the steps of mixing the fecal specimen 4 with a flotation solution 120 having a predetermined specific gravity in a collection device 2 to form a fecal emulsion 40 therein, the parasite ova, eggs or cells being suspended in the fecal emulsion 40, the collection device 2 including an elongated collection tube 12 for holding the fecal emulsion 40 formed from mixing the fecal specimen 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 8; advancing the particle accumulating plug 8 axially into the tube inner bore 58 of the collection tube 12 until the surface of the fecal emulsion 40 therein is substantially level with the pipetting port 32 of the particle accumulating plug 8; centrifuging the fecal emulsion 40 within the collection tube 12 of the collection device 2 for a predetermined period of time so that during or after centrifugation parasite ova, eggs or cells in the fecal emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated parasite ova, eggs or cells; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

Another form of the centrifuge flotation method in accordance with the present invention for separating parasite ova, eggs or cells from a fecal specimen 4 preferably includes the steps of mixing the fecal specimen 4 with a flotation solution 120 having a predetermined specific gravity in a mixing cup to form a fecal emulsion 40 therein, the parasite ova, eggs or cells being suspended in the fecal emulsion 40; pouring a volume of the fecal emulsion 40 from the mixing cup into a collection device 2, the collection device 2 including an elongated collection tube 12 for holding the fecal emulsion 40 formed from mixing the fecal specimen 4 with the flotation solution 120 and a particle accumulating plug 8, the collection tube 12 having a sidewall 56 including an inner surface 42, and defining a tube inner bore 58 and a top opening 10 in communication with the tube inner bore 58, the particle accumulating plug 8 being mounted in the tube inner bore 58 of the collection tube 12 through the top opening 10 thereof and axially movable within the bore 58 to occupy a desired position therein, the particle accumulating plug 8 having an outer sidewall 16 defining a plug inner bore 18, and an inner wall 26 disposed within the plug inner bore 18, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; advancing the particle accumulating plug 8 axially into the tube inner bore 58 of the collection tube 12 until the surface of the fecal emulsion 40 therein is substantially level with the pipetting port 32 of the particle accumulating plug 8; centrifuging the fecal emulsion 40 within the collection tube 12 of the collection device 2 for a predetermined period of time so that during or after centrifugation parasite ova, eggs or cells in the fecal emulsion 40 having a specific gravity which is less than the specific gravity of the flotation solution 120 will rise in the collection tube 12 and accumulate within the funnel 28 defined by the conically-shaped inner wall 26 of the particle accumulating plug 8 to provide a fluid thereat containing a concentrated quantity of separated parasite ova, eggs or cells; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

Another form of the passive flotation method of the present invention for separating particles 6 from a sample of matter 4 preferably includes the steps of mixing the sample of matter 4 with a flotation solution 120 having a predetermined specific gravity in a disposable, self-contained collection device 2 to form an emulsion 40 therein, the particles 6 being suspended in the emulsion 40, the disposable, self-contained collection device 2 including an elongated collection tube 50 for holding the emulsion 40 formed from mixing the sample of matter 4 with the flotation solution 120, a collection scoop assembly 60 and a particle accumulating plug 8, the collection tube 50 having a sidewall 56, the sidewall 56 including an inner surface, and defining a tube inner bore 58 and an open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50 for obtaining the sample of matter 4 and being replaceable on the first axial end 52 of the collection tube 50 such that the sample of matter 4 obtained by the collection assembly will reside within the tube inner bore 58 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; allowing the emulsion 40 within the collection tube 50 of the collection device 2 to rest for a predetermined period of time so that particles 6 in the emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated particles 6; prior to, during or after the step of allowing the emulsion 40 to rest, adding additional flotation solution 120 to the tube inner bore 58 of the collection tube 50 until the surface of the emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Still another form of the passive flotation method of the present invention for separating particles 6 from a sample of matter 4 preferably includes the steps of removing a collection scoop assembly 60 from an open first axial end 52 of an elongated collection tube 50 of a disposable, self-contained collection device 2, the disposable, self-contained collection device 2 including the elongated collection tube 50 for holding an emulsion 40 formed from mixing a sample of matter 4 with a flotation solution 120, the collection scoop assembly 60 and a particle accumulating plug 8, the collection tube 50 having a sidewall 56, the sidewall 56 including an inner surface, and defining a tube inner bore 58 and the open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; obtaining the sample of matter 4 using the collection scoop assembly 60, the sample of matter 4 being disposed on the scoop 70 of the collection scoop assembly 60; replacing the collection scoop assembly 60 on the first axial end 52 of the collection tube 50 such that the sample of matter 4 obtained by the collection scoop assembly 60 will reside within the tube inner bore 58 of the collection tube 50; adding flotation solution 120 having a predetermined specific gravity to the tube inner bore 58 of the collection tube 50 containing therein the sample of matter 4 on the scoop 70 of the collection scoop assembly 60; mixing the sample of matter 4 with the flotation solution 120 to form an emulsion 40 within the tube inner bore 58 of the collection tube 50, the particles 6 being suspended in the emulsion 40; allowing the emulsion 40 within the collection tube 50 of the collection device 2 to rest for a predetermined period of time so that particles 6 in the emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated particles 6; prior to, during or after the step of allowing the emulsion 40 to rest, adding additional flotation solution 120 to the tube inner bore 58 of the collection tube 50 until the surface of the emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Yet another centrifuge flotation method in accordance with the present invention for separating particles 6 from a sample of matter 4 preferably includes the steps of mixing the sample of matter 4 with a flotation solution 120 having a predetermined specific gravity in a disposable, self-contained collection device 2 to form an emulsion 40 therein, the particles 6 being suspended in the emulsion 40, the disposable, self-contained collection device 2 including an elongated collection tube 50 for holding the emulsion 40 formed from mixing the sample of matter 4 with the flotation solution 120, a collection scoop assembly 60 and a particle accumulating plug 8, the collection tube 50 having a sidewall 56, the sidewall 56 including an inner surface, and defining a tube inner bore 58 and an open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50 for obtaining the sample of matter 4 and being replaceable on the first axial end 52 of the collection tube 50 such that the sample of matter 4 obtained by the collection assembly will reside within the tube inner bore 58 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; centrifuging the emulsion 40 within the collection tube 50 of the collection device 2 for a predetermined period of time so that during or after centrifugation particles 6 in the emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated particles 6; prior to or after the step of centrifuging the emulsion 40, adding additional flotation solution 120 to the tube inner bore 58 of the collection tube 50 until the surface of the emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Another form of the passive flotation method in accordance with the present invention for separating parasite ova, eggs or cells from a fecal specimen 4 preferably includes the steps of mixing the fecal specimen 4 with a flotation solution 120 having a predetermined specific gravity in a disposable, self-contained collection device 2 to form a fecal emulsion 40 therein, the parasite ova, eggs or cells being suspended in the fecal emulsion 40, the disposable, self-contained collection device 2 including an elongated collection tube 50 for holding the fecal emulsion 40 formed from mixing the fecal specimen 4 with the flotation solution 120, a collection scoop assembly 60 and a particle accumulating plug 8, the collection tube 50 having a sidewall 56, the sidewall 56 including an inner surface, and defining a tube inner bore 58 and an open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50 for obtaining the fecal specimen 4 and being replaceable on the first axial end 52 of the collection tube 50 such that the fecal specimen 4 obtained by the collection assembly will reside within the tube inner bore 58 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; allowing the fecal emulsion 40 within the collection tube 50 of the collection device 2 to rest for a predetermined period of time so that parasite ova, eggs or cells in the fecal emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated parasite ova, eggs or cells; prior to, during or after the step of allowing the fecal emulsion 40 to rest, adding additional flotation solution 120 to the tube inner bore 58 of the collection tube 50 until the surface of the fecal emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

Another form of the centrifuge flotation method of the present invention for separating particles 6 from a sample of matter 4 preferably includes the steps of removing a collection scoop assembly 60 from an open first axial end 52 of an elongated collection tube 50 of a disposable, self-contained collection device 2, the disposable, self-contained collection device 2 including the elongated collection tube 50 for holding an emulsion 40 formed from mixing a sample of matter 4 with a flotation solution 120, the collection scoop assembly 60 and a particle accumulating plug 8, the collection tube 50 having a sidewall 56, the sidewall 56 including an inner surface, and defining a tube inner bore 58 and the open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; obtaining the sample of matter 4 using the collection scoop assembly 60, the sample of matter 4 being disposed on the scoop 70 of the collection scoop assembly 60; replacing the collection scoop assembly 60 on the first axial end 52 of the collection tube 50 such that the sample of matter 4 obtained by the collection scoop assembly 60 will reside within the tube inner bore 58 of the collection tube 50; adding flotation solution 120 having a predetermined specific gravity to the tube inner bore 58 of the collection tube 50 containing therein the sample of matter 4 on the scoop 70 of the collection scoop assembly 60; mixing the sample of matter 4 with the flotation solution 120 to form an emulsion 40 within the tube inner bore 58 of the collection tube 50, the particles 6 being suspended in the emulsion 40; centrifuging the emulsion 40 within the collection tube 50 of the collection device 2 for a predetermined period of time so that during or after centrifugation particles 6 in the emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated particles 6; prior to or after the step of centrifuging the emulsion 40, adding additional flotation solution 120 to the tube inner bore 58 of the collection tube 50 until the surface of the emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated particles 6 for subsequent analysis.

Still another centrifuge flotation method in accordance with the present invention for separating parasite ova, eggs or cells from a fecal sample 4 preferably includes the steps of mixing the fecal sample 4 with a flotation solution 120 having a predetermined specific gravity in a disposable, self-contained collection device 2 to form a fecal emulsion 40 therein, the parasite ova, eggs or cells being suspended in the fecal emulsion 40, the disposable, self-contained collection device 2 including an elongated collection tube 50 for holding the fecal emulsion 40 formed from mixing the fecal sample 4 with the flotation solution 120, a collection scoop assembly 60 and a particle accumulating plug 8, the collection tube 50 having a sidewall 56, the sidewall 56 including an inner surface, and defining a tube inner bore 58 and an open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50 for obtaining the fecal sample 4 and being replaceable on the first axial end 52 of the collection tube 50 such that the fecal specimen 4 obtained by the collection assembly will reside within the tube inner bore 58 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; centrifuging the fecal emulsion 40 within the collection tube 50 of the collection device 2 for a predetermined period of time so that during or after centrifugation parasite ova, eggs or cells in the fecal emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated parasite ova, eggs or cells; prior to or after the step of centrifuging the fecal emulsion 40, adding additional flotation solution 120 to the tube inner bore 58 of the collection tube 50 until the surface of the fecal emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

A further form of the passive flotation method of the present invention for separating parasite ova, eggs or cells from a fecal specimen 4 preferably includes the steps of removing a collection scoop assembly 60 from an open first axial end 52 of an elongated collection tube 50 of a disposable, self-contained collection device 2, the disposable, self-contained collection device 2 including the elongated collection tube 50 for holding a fecal emulsion 40 formed from mixing a fecal specimen 4 with a flotation solution 120, the collection scoop assembly 60 and a particle accumulating plug 8, the collection tube 50 having a sidewall 56, the sidewall 56 including an inner surface, and defining a tube inner bore 58 and the open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; obtaining the fecal specimen 4 using the collection scoop assembly 60, the fecal specimen 4 being disposed on the scoop 70 of the collection scoop assembly 60; replacing the collection scoop assembly 60 on the first axial end 52 of the collection tube 50 such that the fecal specimen 4 obtained by the collection scoop assembly 60 will reside within the tube inner bore 58 of the collection tube 50; adding flotation solution 120 having a predetermined specific gravity to the tube inner bore 58 of the collection tube 50 containing therein the fecal specimen 4 on the scoop 70 of the collection scoop assembly 60; mixing the fecal specimen 4 with the flotation solution 120 to form a fecal emulsion 40 within the tube inner bore 58 of the collection tube 50, the parasite ova, eggs or cells being suspended in the fecal emulsion 40; allowing the fecal emulsion 40 within the collection tube 50 of the collection device 2 to rest for a predetermined period of time so that parasite ova, eggs or cells in the fecal emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated parasite ova, eggs or cells; prior to, during or after the step of allowing the fecal emulsion 40 to rest, adding additional flotation solution 120 to the tube inner bore 58 of the collection tube 50 until the surface of the fecal emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

Another form of the centrifuge flotation method of the present invention for separating parasite ova, eggs or cells from a fecal specimen 4 preferably includes the steps of removing a collection scoop assembly 60 from an open first axial end 52 of an elongated collection tube 50 of a disposable, self-contained collection device 2, the disposable, self-contained collection device 2 including the elongated collection tube 50 for holding a fecal emulsion 40 formed from mixing a fecal specimen 4 with a flotation solution 120, the collection scoop assembly 60 and a particle accumulating plug 8, the collection tube 50 having a sidewall 56, the sidewall 56 including an inner surface, and defining a tube inner bore 58 and the open first axial end 52 and an opposite open second axial end 54, each of the open first and second axial ends 52, 54 being in communication with the tube inner bore 58, the collection scoop assembly 60 being removably mounted on the first axial end 52 of the collection tube 50, the collection scoop assembly 60 having a handle 72 and a scoop 70 mounted on the handle 72, the collection scoop 70 being removable from the first axial end 52 of the collection tube 50, the particle accumulating plug 8 being mounted on the opposite second axial end 54 of the collection tube 50, the particle accumulating plug 8 having an outer sidewall 86 situated in close proximity to the inner surface of the sidewall 56 of the collection tube 50 and defining a plug inner bore 88, and an inner wall 26 disposed within the plug inner bore 88, the inner wall 26 of the plug 8 being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; obtaining the fecal specimen 4 using the collection scoop assembly 60, the fecal specimen 4 being disposed on the scoop 70 of the collection scoop assembly 60; replacing the collection scoop assembly 60 on the first axial end 52 of the collection tube 50 such that the fecal specimen 4 obtained by the collection scoop assembly 60 will reside within the tube inner bore 58 of the collection tube 50; adding flotation solution 120 having a predetermined specific gravity to the tube inner bore 58 of the collection tube 50 containing therein the fecal specimen 4 on the scoop 70 of the collection scoop assembly 60; mixing the fecal specimen 4 with the flotation solution 120 to form a fecal emulsion 40 within the tube inner bore 58 of the collection tube 50, the parasite ova, eggs or cells being suspended in the fecal emulsion 40; centrifuging the fecal emulsion 40 within the collection tube 50 of the collection device 2 for a predetermined period of time so that during or after centrifugation parasite ova, eggs or cells in the fecal emulsion 40 having a specific gravity which is less than the specific gravity of the flotation solution 120 will rise in the collection tube 50 and accumulate within the funnel 28 defined by the conically-shaped inner wall 26 of the particle accumulating plug 8 to provide a fluid thereat containing a concentrated quantity of separated parasite ova, eggs or cells; prior to or after the step of centrifuging the fecal emulsion 40, adding additional flotation solution 120 to the tube inner bore 58 of the collection tube 50 until the surface of the fecal emulsion 40 therein is substantially level with the pipetting port 32 of the particle accumulating plug 8; inserting the tip 34 of the pipette 36 into the pipetting port 32 of the particle accumulating plug 8; and aspirating into the tip 34 of the pipette 36 through the pipetting port 32 a predetermined volume of the fluid 48 containing a concentrated quantity of separated parasite ova, eggs or cells for subsequent analysis.

A passive flotation method for separating particles 6 from a sample of matter 4 formed in accordance with one form of the present invention preferably includes the steps of mixing the sample of matter 4 with a flotation solution having a predetermined specific gravity in a collection device 2 to form an emulsion 40 therein, the particles 6 being suspended in the emulsion 40, the collection device 2 including an elongated collection tube 12 for holding the emulsion 40 formed from mixing the sample of matter 4 with the flotation solution and a particle accumulating plug, the collection tube 12 having a sidewall including an inner surface 42, and defining a tube inner bore and a top opening 10 in communication with the tube inner bore, the particle accumulating plug being mounted in the tube inner bore of the collection tube 12 at the top opening 10 thereof, the particle accumulating plug having an outer sidewall 16 defining a plug inner bore 18, and an inner wall 26 disposed within the plug inner bore 18, the inner wall 26 of the plug being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; allowing the emulsion 40 within the collection tube 12 of the collection device 2 to rest for a predetermined period of time so that particles 6 in the emulsion 40 having a specific gravity which is less than the specific gravity of the flotation solution will rise in the collection tube 12 and accumulate within the funnel 28 defined by the conically-shaped inner wall 26 of the particle accumulating plug to provide a fluid thereat containing a concentrated quantity of separated particles 6; inserting the tip 34 of the pipette 36 into the pipetting port 32 of the particle accumulating plug; and aspirating into the tip 34 of the pipette 36 through the pipetting port 32 a predetermined volume of the fluid containing a concentrated quantity of separated particles 6 for subsequent analysis.

In yet another form, a passive flotation method in accordance with the present invention for separating particles 6 from a sample of matter 4 preferably includes the steps of mixing the sample of matter 4 with a flotation solution having a predetermined specific gravity in a mixing cup to form an emulsion 40 therein, the particles 6 being suspended in the emulsion 40; pouring a volume of the emulsion 40 from the mixing cup into a collection device 2, the collection device 2 including an elongated collection tube 12 for holding the emulsion 40 formed from mixing the sample of matter 4 with the flotation solution and a particle accumulating plug, the collection tube 12 having a sidewall including an inner surface 42, and defining a tube inner bore and a top opening 10 in communication with the tube inner bore, the particle accumulating plug being mounted in the tube inner bore of the collection tube 12 at the top opening 10 thereof, the particle accumulating plug having an outer sidewall 16 defining a plug inner bore 18, and an inner wall 26 disposed within the plug inner bore 18, the inner wall 26 of the plug being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; allowing the emulsion 40 within the collection tube 12 of the collection device 2 to rest for a predetermined period of time so that particles 6 in the emulsion 40 having a specific gravity which is less than the specific gravity of the flotation solution will rise in the collection tube 12 and accumulate within the funnel 28 defined by the conically-shaped inner wall 26 of the particle accumulating plug to provide a fluid thereat containing a concentrated quantity of separated particles 6; inserting the tip 34 of the pipette 36 into the pipetting port 32 of the particle accumulating plug; and aspirating into the tip 34 of the pipette 36 through the pipetting port 32 a predetermined volume of the fluid containing a concentrated quantity of separated particles 6 for subsequent analysis.

In yet another form of the present invention, a centrifuge flotation method for separating particles 6 from a sample of matter 4 preferably includes the steps of mixing the sample of matter 4 with a flotation solution having a predetermined specific gravity in a collection device 2 to form an emulsion 40 therein, the particles 6 being suspended in the emulsion 40, the collection device 2 including an elongated collection tube 12 for holding the emulsion 40 formed from mixing the sample of matter 4 with the flotation solution and a particle accumulating plug, the collection tube 12 having a sidewall including an inner surface 42, and defining a tube inner bore and a top opening 10 in communication with the tube inner bore, the particle accumulating plug being mounted in the tube inner bore of the collection tube 12 at the top opening 10 thereof, the particle accumulating plug having an outer sidewall 16 defining a plug inner bore 18, and an inner wall 26 disposed within the plug inner bore 18, the inner wall 26 of the plug being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; centrifuging the emulsion 40 within the collection tube 12 of the collection device 2 for a predetermined period of time so that during or after centrifugation particles 6 in the emulsion 40 having a specific gravity which is less than the specific gravity of the flotation solution will rise in the collection tube 12 and accumulate within the funnel 28 defined by the conically-shaped inner wall 26 of the particle accumulating plug to provide a fluid thereat containing a concentrated quantity of separated particles 6; inserting the tip 34 of the pipette 36 into the pipetting port 32 of the particle accumulating plug; and aspirating into the tip 34 of the pipette 36 through the pipetting port 32 a predetermined volume of the fluid containing a concentrated quantity of separated particles 6 for subsequent analysis.

Still another centrifuge flotation method in accordance with the present invention for separating particles 6 from a sample of matter 4 preferably includes the steps of mixing the sample of matter 4 with a flotation solution having a predetermined specific gravity in a mixing cup to form an emulsion 40 therein, the particles 6 being suspended in the emulsion 40; pouring a volume of the emulsion 40 from the mixing cup into a collection device 2, the collection device 2 including an elongated collection tube 12 for holding the emulsion 40 formed from mixing the sample of matter 4 with the flotation solution and a particle accumulating plug, the collection tube 12 having a sidewall including an inner surface 42, and defining a tube inner bore and a top opening 10 in communication with the tube inner bore, the particle accumulating plug being mounted in the tube inner bore of the collection tube 12 at the top opening 10 thereof, the particle accumulating plug having an outer sidewall 16 defining a plug inner bore 18, and an inner wall 26 disposed within the plug inner bore 18, the inner wall 26 of the plug being conically-shaped to define an inverted funnel 28 having an apex 30, the conically-shaped inner wall 26 converging to the apex 30 and having a pipetting port 32 formed through the thickness thereof at the apex 30, the pipetting port 32 being dimensioned to receive the tip 34 of a pipette 36; centrifuging the emulsion 40 within the collection tube 12 of the collection device 2 for a predetermined period of time so that during or after centrifugation particles 6 in the emulsion 40 having a specific gravity which is less than the specific gravity of the flotation solution will rise in the collection tube 12 and accumulate within the funnel 28 defined by the conically-shaped inner wall 26 of the particle accumulating plug to provide a fluid thereat containing a concentrated quantity of separated particles 6; inserting the tip 34 of the pipette 36 into the pipetting port 32 of the particle accumulating plug; and aspirating into the tip 34 of the pipette 36 through the pipetting port 32 a predetermined volume of the fluid containing a concentrated quantity of separated particles 6 for subsequent analysis.

As mentioned previously, it should be noted that use of the collection devices 2 of the present invention is not limited to the separation and collection of parasite ova, eggs or cells from a fecal specimen, but may be used in many different applications for separating and collecting particles from various types of matter, for example, in soil sample testing.

More specifically, it is envisioned that the collection device 2 and particle accumulating plug 8 thereof may be used to separate a variety of different forms of particles in a passive or centrifuge flotation method, including but not limited to such particles as microparticles, beads, wafers, microbeads, magnetic particles or beads, barcoded beads and barcoded magnetic beads, and particles made from a variety of materials, including but not limited to latex, polystyrene, polymers, silica, nickel or combinations thereof. For example, magnetic barcoded beads (with or without biomolecules immobilized thereon) that are suspended in a suitable liquid may be separated from the liquid using the collection devices 2, particle accumulating plugs 8 and methods of the present invention disclosed herein.

Furthermore, particles of varying sizes and dimensions may be separated using the collection devices 2, particle accumulating plugs 8 and methods disclosed herein. As a non-limiting example only, it is envisioned that particles having a size or other dimension in a range of about 10 microns to about 500 microns, or having smaller or larger dimensions than those within the aforementioned range, could be separated using the collection devices 2, particle accumulating plugs 8 and methods of the present invention disclosed herein.

As mentioned previously, the preferred flotation solutions for separating parasite eggs and ova are zinc sulfate, magnesium sulfate and sodium chloride. Another flotation solution is sodium nitrate. However, for separating other types of particles, different flotation solutions from those mentioned above may be used, including but not limited to those solutions made from salts, polymers, polysaccharides, sugars and others dissolved in a suitable solvent, to constitute a flotation solution with a specific gravity greater than that of the particles to be separated. The flotation solution could in some instances be pure water.

In another form of the present invention, the particle accumulating plug 8 of the collection device 2 may be separate piece that is received by the tube 12, 50, or may be integrally formed with the tube 12, 50, for example, where the plug 8 or portions thereof and the cylindrical sidewall 56 of the tube 12, 50 form a single integrated part.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A collection device for separating particles from a sample of matter and concentrating the particles therein for subsequent extraction and analysis, which comprises:
    an elongated collection tube for holding an emulsion formed from mixing the sample of matter with a flotation solution used in separating the particles from the sample of matter, the particles being suspended in the emulsion, the collection tube having a sidewall, the sidewall including an inner surface, and defining a tube inner bore and a top opening in communication with the tube inner bore; and
    a particle accumulating plug, the particle accumulating plug being mounted in the tube inner bore of the collection tube at the top opening thereof, the particle accumulating plug having an outer sidewall defining a plug inner bore, and an inner wall disposed within the plug inner bore, the inner wall of the plug being conically shaped to define an inverted funnel having an apex, the conically-shaped inner wall converging to the apex and having a pipetting port formed through the thickness thereof at the apex, the pipetting port being dimensioned to receive the tip of a pipette;
    wherein particles suspended in the emulsion that rise in the collection tube are directed by the conically-shaped inner wall to accumulate within the funnel defined by the conically-shaped inner wall, providing a fluid threat having a concentrated quantity of separated particles for extraction therefrom by the fluid being aspirated into the tip of the pipette inserted into the pipetting port.

2. A collection device as defined by claim 1, wherein at least a portion of the sidewall of the collection tube is transparent so that the particle accumulating plug within the tube inner bore is viewable through the transparent portion of the sidewall of the collection tube.

3. A collection device as defined by claim 1, wherein at least a portion of the sidewall of the collection tube is transparent so that the particle accumulating plug within the tube inner bore is viewable through the transparent portion of the sidewall of the collection tube; and
    wherein at least a portion of the outer sidewall of the particle accumulating plug and at least a portion of the conically-shaped inner wall of the particle accumulating plug are transparent so that the level of the emulsion within the tube inner bore of the collection tube and within the funnel defined by the conically-shaped inner wall of the particle accumulating plug is viewable through the transparent portion of the sidewall of the collection tube, the transparent portion of the outer sidewall of the particle accumulating plug and the transparent portion of the conically-shaped inner wall of the particle accumulating plug.

4. A collection device as defined by claim 1, wherein the particle accumulating plug includes a screen, the screen being disposed within the plug inner bore below the conically-shaped inner wall at a position opposite to the apex of the funnel defined by the inner wall and where separated particles enter the funnel.

5. A collection device as defined by claim 4, wherein the screen has a multiplicity of pores formed through the thickness thereof, the screen being formed to define the pores with a general dimension of about 180 microns.

6. A collection device as defined by claim 1, wherein the angle of the conically-shaped inner wall of the particle accumulating plug measured relative to a longitudinal central axis of the particle accumulating plug is between about 5 degrees and about 60 degrees.

7. A collection device as defined by claim 1, wherein the angle of the conically-shaped inner wall of the particle accumulating plug measured relative to a longitudinal central axis of the particle accumulating plug is between about 9 degrees and about 50 degrees.

8. A collection device as defined by claim 1, wherein the angle of the conically-shaped inner wall of the particle accumulating plug measured relative to a longitudinal central axis of the particle accumulating plug is about 9.6 degrees.

9. A collection device as defined by claim 1, wherein the particle accumulating plug includes a fill port formed through the thickness thereof and having a plug wall defining a fill bore, the fill bore being in fluid communication with the fill port, the fill port and fill bore allowing a flotation solution to be added to the tube inner bore of the collection tube.

10. A collection device as defined by claim 1, wherein the outer sidewall of the particle accumulating plug has a fill channel formed therein, the fill channel being in fluid communication with the top opening and inner bore of the elongated collection tube, the fill channel allowing a flotation solution to be added to the tube inner bore of the collection tube.

11. A collection device as defined by claim 10, wherein the outer sidewall of the particle accumulating plug has formed through the thickness thereof a notch, the notch being situated in alignment with and in fluid communication with the fill channel to allow flotation solution within or added to the fill channel to flow therethrough and into the tube inner bore of the collection tube.

12. A collection device for separating parasite ova, eggs or cells from a fecal specimen and concentrating the parasite ova, eggs or cells therein for subsequent extraction and analysis, which comprises:
an elongated collection tube for holding a fecal emulsion formed from mixing the fecal specimen with a flotation solution used in separating the parasite ova, eggs or cells from the fecal specimen, the parasite ova, eggs or cells being suspended in the emulsion, the collection tube having a sidewall, the sidewall including an inner surface, and defining a tube inner bore and a top opening in communication with the tube inner bore; and
a particle accumulating plug, the particle accumulating plug being mounted in the tube inner bore of the collection tube at the top opening thereof, the particle accumulating plug having an outer sidewall defining a plug inner bore, and an inner wall disposed within the plug inner bore, the inner wall of the plug being conically shaped to define an inverted funnel having an apex, the conically-shaped inner wall converging to the apex and having a pipetting port formed through the thickness thereof at the apex, the pipetting port being dimensioned to receive the tip of a pipette;
wherein parasite ova, eggs or cells suspended in the fecal emulsion that rise in the collection tube are directed by the conically-shaped inner wall to accumulate within the funnel defined by the conically-shaped inner wall, providing a fluid thereat having a concentrated quantity of separated parasite ova, eggs or cells for extraction therefrom by the fluid being aspirated into the tip of the pipette inserted into the pipetting port.

13. A collection device as defined by claim 12, wherein at least a portion of the sidewall of the collection tube is transparent so that the particle accumulating plug within the tube inner bore is viewable through the transparent portion of the sidewall of the collection tube.

14. A collection device as defined by claim 12, wherein at least a portion of the sidewall of the collection tube is transparent so that the particle accumulating plug within the tube inner bore is viewable through the transparent portion of the sidewall of the collection tube; and
wherein at least a portion of the outer sidewall of the particle accumulating plug and at least a portion of the conically-shaped inner wall of the particle accumulating plug are transparent so that the level of the fecal emulsion within the tube inner bore of the collection tube and within the funnel defined by the conically-shaped inner wall of the particle accumulating plug is viewable through the transparent portion of the sidewall of the collection tube, the transparent portion of the outer sidewall of the particle accumulating plug and the transparent portion of the conically-shaped inner wall of the particle accumulating plug.

15. A collection device as defined by claim 12, wherein the particle accumulating plug includes a screen, the screen being disposed within the plug inner bore below the conically-shaped inner wall at a position opposite to the apex of the funnel defined by the inner wall and where separated parasite ova, eggs or cells enter the funnel.

16. A collection device as defined by claim 15, wherein the screen has a multiplicity of pores formed through the thickness thereof, the screen being formed to define the pores with a general dimension of about 180 microns.

17. A collection device as defined by claim 12, wherein the angle of the conically-shaped inner wall of the particle accumulating plug measured relative to a longitudinal central axis of the particle accumulating plug is between about 5 degrees and about 60 degrees.

18. A collection device as defined by claim 12, wherein the angle of the conically-shaped inner wall of the particle accumulating plug measured relative to a longitudinal central axis of the particle accumulating plug is between about 9 degrees and about 50 degrees.

19. A collection device as defined by claim 12, wherein the angle of the conically-shaped inner wall of the particle accumulating plug measured relative to a longitudinal central axis of the particle accumulating plug is about 9.6 degrees.

20. A collection device as defined by claim 12, wherein the particle accumulating plug includes a fill port formed through the thickness thereof and having a plug wall defining a fill bore, the fill bore being in fluid communication with the fill port, the fill port and fill bore allowing a flotation solution to be added to the tube inner bore of the collection tube.

21. A collection device as defined by claim 12, wherein the outer sidewall of the particle accumulating plug has a fill channel formed therein, the fill channel being in fluid communication with the top opening and inner bore of the elongated collection tube, the fill channel allowing a flotation solution to be added to the tube inner bore of the collection tube.

22. A collection device as defined by claim 21, wherein the outer sidewall of the particle accumulating plug has formed through the thickness thereof a notch, the notch being situated in alignment with and in fluid communication with the fill channel to allow flotation solution within or added to the fill channel to flow therethrough and into the tube inner bore of the collection tube.

23. A particle accumulating plug for use in a collection device for separating particles from a sample of matter and concentrating the particles therein for subsequent extraction and analysis, the collection device including an elongated collection tube for holding an emulsion formed from mixing the sample of matter with a flotation solution used in separating the particles from the sample of matter, the particles being suspended in the emulsion, the collection tube having a sidewall, the sidewall including an inner surface, and defining a tube inner bore and a top opening in communication with the tube inner bore, the particle accumulating plug being mountable in the tube inner bore of the collection tube at the top opening thereof, the particle accumulating plug comprising:
an outer sidewall defining a plug inner bore; and
an inner wall disposed within the plug inner bore, the inner wall of the plug being conically shaped to define an inverted funnel having an apex, the conically-shaped inner wall converging to the apex and having a pipetting port formed through the thickness thereof at the apex, the pipetting port being dimensioned to receive the tip of a pipette;

wherein particles suspended in the emulsion that rise in the collection tube are directed by the conically-shaped inner wall to accumulate within the funnel defined by the conically-shaped inner wall, providing a fluid threat having a concentrated quantity of separated particles for extraction therefrom by the fluid being aspirated into the tip of the pipette inserted into the pipetting port.

24. A particle accumulating plug as defined by claim 23, wherein the particle accumulating plug includes a screen, the screen being disposed within the plug inner bore below the conically-shaped inner wall at a position opposite to the apex of the funnel defined by the inner wall and where separated particles enter the funnel.

25. A particle accumulating plug as defined by claim 24, wherein the screen has a multiplicity of pores formed through the thickness thereof, the screen being formed to define the pores with a general dimension of about 180 microns.

26. A particle accumulating plug as defined by claim 23, wherein the angle of the conically-shaped inner wall of the particle accumulating plug measured relative to a longitudinal central axis of the particle accumulating plug is between about 5 degrees and about 60 degrees.

27. A particle accumulating plug as defined by claim 23, wherein the angle of the conically-shaped inner wall of the particle accumulating plug measured relative to a longitudinal central axis of the particle accumulating plug is between about 9 degrees and about 50 degrees.

28. A particle accumulating plug as defined by claim 23, wherein the angle of the conically-shaped inner wall of the particle accumulating plug measured relative to a longitudinal central axis of the particle accumulating plug is about 9.6 degrees.

29. A particle accumulating plug as defined by claim 23, wherein the particle accumulating plug includes a fill port formed through the thickness thereof and having a plug wall defining a fill bore, the fill bore being in fluid communication with the fill port, the fill port and fill bore allowing a flotation solution to be added to the tube inner bore of the collection tube.

30. A particle accumulating plug as defined by claim 23, wherein the outer sidewall of the particle accumulating plug has a fill channel formed therein, the fill channel being in fluid communication with the top opening and inner bore of the elongated collection tube, the fill channel allowing a flotation solution to be added to the tube inner bore of the collection tube.

31. A particle accumulating plug as defined by claim 30, wherein the outer sidewall of the particle accumulating plug has formed through the thickness thereof a notch, the notch being situated in alignment with and in fluid communication with the fill channel to allow flotation solution within or added to the fill channel to flow therethrough and into the tube inner bore of the collection tube.

32. A particle accumulating plug for use in a collection device for separating particles from a sample of matter and concentrating the particles therein for subsequent extraction and analysis, the collection device including an elongated collection tube for holding an emulsion formed from mixing the sample of matter with a flotation solution used in separating the particles from the sample of matter, the particles being suspended in the emulsion, the collection tube having a sidewall at least a portion of which is transparent, the sidewall including an inner surface, and defining a tube inner bore and a top opening in communication with the tube inner bore, the particle accumulating plug being mountable in the tube inner bore of the collection tube at the top opening thereof, the particle accumulating plug being viewable through the transparent portion of the sidewall of the collection tube, the particle accumulating plug comprising:

an outer sidewall defining a plug inner bore; and an inner wall disposed within the plug inner bore, the inner wall of the plug being conically shaped to define an inverted funnel having an apex, the conically-shaped inner wall converging to the apex and having a pipetting port formed through the thickness thereof at the apex, the pipetting port being dimensioned to receive the tip of a pipette;

wherein particles suspended in the emulsion that rise in the collection tube are directed by the conically-shaped inner wall to accumulate within the funnel defined by the conically-shaped inner wall, providing a fluid threat having a concentrated quantity of separated particles for extraction therefrom by the fluid being aspirated into the tip of the pipette inserted into the pipetting port.

33. A particle accumulating plug for use with a collection device as defined by claim 32, wherein at least a portion of the outer sidewall of the particle accumulating plug and at least a portion of the conically-shaped inner wall of the particle accumulating plug are transparent so that the level of the emulsion within the tube inner bore of the collection tube and within the funnel defined by the conically-shaped inner wall of the particle accumulating plug is viewable through the transparent portion of the sidewall of the collection tube, the transparent portion of the outer sidewall of the particle accumulating plug and the transparent portion of the conically-shaped inner wall of the particle accumulating plug when the particle accumulating plug is used with the collection device.

34. A particle accumulating plug as defined by claim 32, wherein the angle of the conically-shaped inner wall of the particle accumulating plug measured relative to a longitudinal central axis of the particle accumulating plug is between about 5 degrees and about 60 degrees.

35. A particle accumulating plug as defined by claim 32, wherein the angle of the conically-shaped inner wall of the particle accumulating plug measured relative to a longitudinal central axis of the particle accumulating plug is between about 9 degrees and about 50 degrees.

36. A particle accumulating plug as defined by claim 32, wherein the angle of the conically-shaped inner wall of the particle accumulating plug measured relative to a longitudinal central axis of the particle accumulating plug is about 9.6 degrees.

37. A particle accumulating plug as defined by claim 32, wherein the particle accumulating plug includes a fill port formed through the thickness thereof and having a plug wall defining a fill bore, the fill bore being in fluid communication with the fill port, the fill port and fill bore allowing a flotation solution to be added to the tube inner bore of the collection tube.

38. A particle accumulating plug as defined by claim 32, wherein the outer sidewall of the particle accumulating plug has a fill channel formed therein, the fill channel being in fluid communication with the top opening and inner bore of the elongated collection tube, the fill channel allowing a flotation solution to be added to the tube inner bore of the collection tube.

39. A particle accumulating plug as defined by claim 38, wherein the outer sidewall of the particle accumulating plug has formed through the thickness thereof a notch, the notch being situated in alignment with and in fluid communication with the fill channel to allow flotation solution within or added to the fill channel to flow therethrough and into the tube inner bore of the collection tube.

* * * * *